(12) United States Patent
Gao et al.

(10) Patent No.: US 8,946,389 B2
(45) Date of Patent: Feb. 3, 2015

(54) COMPOSITIONS AND METHODS FOR MULTIPLEX BIOMARKER PROFILING

(75) Inventors: Xiaohu Gao, Seattle, WA (US); Pavel Zrazhevskiy, Seattle, WA (US)

(73) Assignee: University of Washington, Seattle, WA (US)

(*) Notice: Subject to any disclaimer, the term of this patent is extended or adjusted under 35 U.S.C. 154(b) by 226 days.

(21) Appl. No.: 13/455,674

(22) Filed: Apr. 25, 2012

(65) Prior Publication Data

US 2015/0004598 A1 Jan. 1, 2015

Related U.S. Application Data

(60) Provisional application No. 61/478,618, filed on Apr. 25, 2011, provisional application No. 61/478,626, filed on Apr. 25, 2011.

(51) Int. Cl.
*G01N 33/53* (2006.01)
*G01N 33/58* (2006.01)

(52) U.S. Cl.
CPC ............ *G01N 33/588* (2013.01); *G01N 33/587* (2013.01)
USPC ........................ 530/387.1; 435/6.11; 435/7.1

(58) Field of Classification Search
CPC .............. G01N 27/3276; G01N 27/42; G01N 27/3278; G01N 27/745; G01N 33/48721; G01N 33/587; G01N 33/588
See application file for complete search history.

(56) References Cited

U.S. PATENT DOCUMENTS 7,186,814 B2 * 3/2007 Garimella et al. ........... 536/23.1
2006/0014172 A1 * 1/2006 Muller et al. ...................... 435/6

FOREIGN PATENT DOCUMENTS

WO 2010/115089 10/2010

OTHER PUBLICATIONS

Bailey et al., Journal of the American Chemical Society, 129(7):1959-67 (2007). "DNA-encoded antibody libraries: a unified platform for multiplexed cell sorting and detection of genes and proteins."
Cady et al., Molecular and Cellular Probes, 21(2):116-24 (2007). "Optimized linkage and quenching strategies for quantum dot molecular beacons."
Chan et al., Nucleic Acids Res, 33(18):e161 (2005). "Method for multiplex cellular detection of mRNAs using quantum dot fluorescent in situ hybridization."
Chen et al., J. Mol. Biol., 293: 865-881(1999). "Selection and analysis of an optimized anti-VEGF antibody: crystal structure of an affinity-matured Fab in complex with antigen."
Christensen N.K. & Winther L., Chapter 15 in IHC Staining Methods, 5th Edition, pp. 103-108 (2009). "Immunohistochemical staining methods."
Goldman et al., Anal Chem, 74:841-847 (2002). "Conjugation of luminescent quantum dots with antibodies using an engineered adaptor protein to provide new reagents for fluoroimmunoassays."
Goldman et al., J Am Chem Soc, 124:6378-6382 (2002). "Avidin: a natural bridge for quantum dot-antibody conjugates."
Gueroui et al., Physical Review Letters, 93(16):166108 (2004). "Single-molecule measurements of gold-quenched quantum dots."
Guo et al., PNAS, 108(9): 3493-3498 (2011). "Multispectral labeling of antibodies with polyfluorophores on a DNA backbone and application in cellular imaging."
Han, K.-C., Ahn, D.-R. & Yang E.G., Bioconjugate Chem., 21(12): 2190-2196 (2010). "An approach to multiplexing an immunosorbent assay with antibody-oligonucleotide conjugates."
Hendrickson et al., Nucleic Acids Research, 23(3): 522-529 (1995). "High sensitivity multianalyte immunoassay using covalent DNA-labeled antibodies and polymerase chain reaction."
Jaiswal et al., Nat Biotechnol, 21:47-51 (2003). "Long-term multiple color imaging of live cells using quantum dot bioconjugates."
Jin et al., Molecular BioSystems, 6: 2325-2331 (2010). "Antibody-ProteinA conjugated quantum dots for multiplexed imaging of surface receptors in living cells."
Kang et al., Small, 5:2519-2522 (2009). "Multiplex imaging of single tumor cells using quantum-dot-conjugated aptamers."
Lim et al., Analytical Chemistry, 82(3):886-91 (2010). "Specific nucleic acid detection using photophysical properties of quantum dot probes."
Lim et al., Biomaterials, 30:1197-1204 (2009). "Simultaneous intracellular delivery of targeting antibodies and functional nanoparticles with engineered protein G system."
Lind et al., Journal of Immunological Methods, 304(1-2):107-16 (2005). "Development and evaluation of three real-time time immune-PCR assemblages for quantification of PSA."
Matsuno et al., J Histochem Cytochem, 53(7):833-8 (2005). "Three-dimensional imaging of the intracellular localization of growth hormone and prolactin and their mRNA using nanocrystal (Quantum dot) and confocal laser scanning microscopy techniques."
Nash D.R., Crabbé P.A. & Heremans J.F., Immunology, 16:785-790 (1969). "Sequential immunofluorescent staining: a simple and useful technique."
Niemeyer C.M, Angew. Chem. Int. Ed., 49:1200-1216 (2010). "Semisynthetic DNA-protein conjugates for biosensing and nanofabrication."

(Continued)

*Primary Examiner* — James Martinell
(74) *Attorney, Agent, or Firm* — Mark J. FitzGerald; Nixon Peabody LLP

(57) ABSTRACT

Provided herein are compositions and methods for identifying or quantitating one or more analytes in sample. The composition can comprise an affinity molecule reversibly conjugated to a label moiety via a double-stranded nucleic acid linker or via an adaptor molecule. The affinity molecule and the label moiety can be linked to different strands of the double-stranded nucleic acid linker. Compositions can be used in any biological assays for detection, identification and/or quantification of target molecules or analytes, including multiplex staining for molecular profiling of individual cells or cellular populations. For example, the compositions can be adapted for use in immunofluorescence, fluorescence in situ hybridization, immunohistochemistry, western blot, and the like.

26 Claims, 24 Drawing Sheets

(56) References Cited

OTHER PUBLICATIONS

Schubert et al., Nature Biotechnology, doi:10.1038/nbt1250 (published online Oct. 1, 2006). "Analyzing proteom topology and function by automated multidimensional fluorescence microscopy."

Smith et al., Expert Rev. Mol. Diagn, 6(2): 231-244 (2006). "Multicolor quantum dots for molecular diagnostics of cancer."

Tholouli et al., Biochemical and Biophysical Research Communications, 348(2):628-36 (2006). "Imaging of multiple mRNA targets using quantum dot based in situ hybridization and spectral deconvolution in clinical biopsies."

Xing et al., Nat Protoc, 2:1152-1165 (2007). "Bioconjugated quantum dots for multiplexed and quantitative immunochemistry."

Xing Y. & Rao J., Cancer Biomarkers, 4: 307-319 (2008). "Quantum dot bioconjugates for in vitro diagnostics & in vivo imaging."

Zhang Q. & Guao, L.-H., Bioconjugate Chem., 18: 1668-1672 (2007). "Multiple labeling of antibodies with dye/DNA conjugate for sensitivity improvement in fluorescence immunoassay."

Zrazhevskiy et al., Chemical Society Reviews, 39:4326-4354 (2010). "Designing multifunctional quantum dots for bioimaging, detection, and drug delivery."

Alivisatos, A.P., Perspectives on the physical chemistry of semiconductor nanocrystals. Journal of Physical Chemistry, 1996. 100(31): p. 13226-13239.

Alivisatos A.P., Semiconductor clusters, nanocrystals, and quantum dots. Science, 1996. 271(5251): p. 933-937.

Bruchez, M. et al., Science, 281(5385):p. 2013-6 (1998). "Semiconductor nanocrystals as fluorescent biological labels."

Chan, W.C., et al., Luminescent quantum dots for multiplexed biological detection and imaging. Curr Opin Biotechnol, 2002. 13(1): p. 40-6.

Chen, C., et al., Quantum-dot-based immunofluorescent imaging of HER2 and ER provides new insights into breast cancer heterogeneity. Nanotechnology, 2010. 21(9): p. 095101.

Englert, C.R., G.V. Baibakov, and M.R. Emmert-Buck, Layered expression scanning: rapid molecular profiling of tumor samples. Cancer Research, 2000. 60(6): p. 1526-30.

Fountaine, T.J., et al., Multispectral imaging of clinically relevant cellular targets in tonsil and lymphoid tissue using semiconductor quantum dots. Modern Pathology, 2006. 19(9): p. 1181-91.

Furuya, T., et al., A novel technology allowing immunohistochemical staining of a tissue section with 50 different antibodies in a single experiment. Journal of Histochemistry and Cytochemistry, 2004. 52(2): p. 205-10.

Gao, X. and S. Nie, Molecular profiling of single cells and tissue specimens with quantum dots. Trends Biotechnol, 2003. 21(9): p. 371-3).

Ghazani, A.A., et al., High throughput quantification of protein expression of cancer antigens in tissue microarray using quantum dot nanocrystals. Nano Letters, 2006. 6(12): p. 2881-6.

Glass, G., J.A. Papin, and J.W. Mandell, SIMPLE: a sequential immunoperoxidase labeling and erasing method. Journal of Histochemistry and Cytochemistry, 2009. 57(10): p. 899-905.

Huang, D.H., et al., Comparison and Optimization of Multiplexed Quantum Dot-Based Immunohistofluorescence. Nano Research, 2010. 3(1): p. 61-68.

Liu, A.Y., M.P. Roudier, and L.D. True, Heterogeneity in primary and metastatic prostate cancer as defined by cell surface CD profile. American Journal of Pathology, 2004. 165(5): p. 1543-1556.

Liu, J., et al., Molecular mapping of tumor heterogeneity on clinical tissue specimens with multiplexed quantum dots. ACS Nano, 2010. 4(5): p. 2755-65.

Liu, J., et al., Multiplexed detection and characterization of rare tumor cells in Hodgkin's lymphoma with multicolor quantum dots. Analytical Chemistry, 2010. 82(14): p. 6237-43.

Pirici, D., et al., Antibody elution method for multiple immunohistochemistry on primary antibodies raised in the same species and of the same subtype. Journal of Histochemistry and Cytochemistry, 2009. 57(6): p. 567-75.

Schwamborn, K. and R.M. Caprioli, Molecular imaging by mass spectrometry—looking beyond classical histology. Nature Reviews. Cancer, 2010. 10(9): p. 639-46.

Shi, C., et al., Quantum dots-based multiplexed immunohistochemistry of protein expression in human prostate cancer cells. European Journal of Histochemistry, 2008. 52(2): p. 127-34.

Sweeney, E., et al., Quantitative multiplexed quantum dot immunohistochemistry. Biochemical and Biophysical Research Communications, 2008. 374(2): p. 181-6.

Toth, Z.E. and Mezey, E., Simultaneous visualization of multiple antigens with tyramide signal amplification using antibodies from the same species. Journal of Histochemistry and Cytochemistry, 2007. 55(6): p. 545-54.

True, L.D. and Gao, X., Quantum dots for molecular pathology: their time has arrived. J Mol Diagn, 2007. 9(1): p. 7-11).

Wahlby, C., et al., Sequential immunofluorescence staining and image analysis for detection of large numbers of antigens in individual cell nuclei. Cytometry, 2002. 47(1): p. 32-41.

Wollscheid, B., et al., Mass-spectrometric identification and relative quantification of N-linked cell surface glycoproteins. Nature Biotechnology, 2009. 27(4): p. 378-86.

Wu, X., et al., Immunofluorescent labeling of cancer marker Her2 and other cellular targets with semiconductor quantum dots. Nat Biotechnol, 2003. 21(1): p. 41-6.

Yezhelyev, M.V., et al., In situ molecular profiling of breast cancer biomarkers with multicolor quantum dots. Advanced Materials, 2007. 19(20): p. 3146-3151.

Zrazhevskiy, P. and Gao, X., Multifunctional Quantum Dots for Personalized Medicine. Nano Today, 2009. 4(5): p. 414-428.

Zrazhevskiy, P. and Gao, X., Quantum dots for cancer molecular imaging. Minerva Biotecnologica, 2009. 21(1): p. 37-52).

\* cited by examiner

COMPOSITIONS AND METHODS FOR MULTIPLEX BIOMARKER PROFILING

CROSS-REFERENCE TO RELATED APPLICATIONS

This application claims benefit under 35 U.S.C. §119(e) of the U.S. Provisional Application No. 61/478,618, filed Apr. 25, 2011 and U.S. Provisional Application No. 61/478,626, filed Apr. 25, 2011, the content of both of which is incorporated herein by reference in its entirety

GOVERNMENT SUPPORT

This invention was made with government support under grant no. W81XWH-07-1-0117 awarded by the Department of Defense, no. 5R01CA131797 and no. 1R01CA140295 awarded by the National Institutes of Health, and no. 0645080 awarded by the National Science Foundation. The government has certain rights in the invention.

TECHNICAL FIELD

The present disclosure relates generally to compositions and methods for visualization and staining of analytes in a sample.

BACKGROUND

Comprehensive and accurate molecular profiling on a single-cell level is highly sought after within the fields of cell biology, pathology, and clinical diagnostics, especially for untangling the complex interactions underlying cancer, neurological disorders, and immune system disorders. A key challenge is presented by the complexity and heterogeneity of these diseases (Liu, A. Y., M. P. Roudier, and L. D. True, *Heterogeneity in primary and metastatic prostate cancer as defined by cell surface CD profile*. American Journal of Pathology, 2004. 165(5): p. 1543-1556 and True, L. D. and X. Gao, *Quantum dots for molecular pathology: their time has arrived*. J Mol Diagn, 2007. 9(1): p. 7-11), which is hard to assess using conventional biomedical techniques that suffer from a limitation in the number of biomarkers that can be analyzed simultaneously, provide limited single-cell information, and often utilize qualitative rather than quantitative analysis. See for example, Englert, C. R., G. V. Baibakov, and M. R. Emmert-Buck, *Layered expression scanning: rapid molecular profiling of tumor samples*. Cancer Research, 2000. 60(6): p. 1526-30; Furuya, T., et al., *A novel technology allowing immunohistochemical staining of a tissue section with 50 different antibodies in a single experiment*. Journal of Histochemistry and Cytochemistry, 2004. 52(2): p. 205-10; Glass, G., J. A. Papin, and J. W. Mandell, *SIMPLE: a sequential immunoperoxidase labeling and erasing method*. Journal of Histochemistry and Cytochemistry, 2009. 57(10): p. 899-905; Pirici, D., et al., *Antibody elution method for multiple immunohistochemistry on primary antibodies raised in the same species and of the same subtype*. Journal of Histochemistry and Cytochemistry, 2009. 57(6): p. 567-75; Schwamborn, K. and R. M. Caprioli, *Molecular imaging by mass spectrometry—looking beyond classical histology*. Nature Reviews. Cancer, 2010. 10(9): p. 639-46; Toth, Z. E. and E. Mezey, *Simultaneous visualization of multiple antigens with tyramide signal amplification using antibodies from the same species*. Journal of Histochemistry and Cytochemistry, 2007. 55(6): p. 545-54; Wahlby, C., et al., *Sequential immunofluorescence staining and image analysis for detection of large numbers of antigens in individual cell nuclei*. Cytometry, 2002. 47(1): p. 32-41; and Wollscheid, B., et al., *Mass-spectrometric identification and relative quantification of N-linked cell surface glycoproteins*. Nature Biotechnology, 2009. 27(4): p. 378-86. Consequently, fundamental understanding of pathological processes as well as clinical diagnostics are limited by the lack of knowledge about the predictive biomarkers that would unambiguously discriminate between disease and normal function, distinguish different disease types, and provide information about possible progression of the pathological process.

Advances in nanotechnology have enabled the design of nanoparticle-based tools for improved molecular characterization of physiological and pathological processes. In particular, semiconductor fluorescent nanoparticles (quantum dots, or QDs) have emerged as a new platform for high-throughput quantitative characterization of multiple biomarkers in cells and clinical tissue specimens (Zrazhevskiy, P. and X. Gao, *Multifunctional Quantum Dots for Personalized Medicine*. Nano Today, 2009. 4(5): p. 414-428 and Zrazhevskiy, P. and X. Gao, *Quantum dots for cancer molecular imaging*. Minerva Biotecnologica, 2009. 21(1): p. 37-52). Having size of only 2 to 10 nm in diameter, QDs possess unique photo-physical properties drastically different from those of single atoms or bulk materials. Size-tunable and spectrally narrow light emission, simultaneous excitation of multiple colors, improved brightness, resistance to photobleaching, and large Stokes shift enable simultaneous parallel detection and reliable quantification of up to 10 spectrally distinct QD probes Alivisatos, A. P., *Perspectives on the physical chemistry of semiconductor nanocrystals*. Journal of Physical Chemistry, 1996. 100(31): p. 13226-13239; Alivisatos, A. P., *Semiconductor clusters, nanocrystals, and quantum dots*. Science, 1996. 271(5251): p. 933-937; Bruchez, M., Jr., et al., *Semiconductor nanocrystals as fluorescent biological labels*. Science, 1998. 281(5385): p. 2013-6; Chan, W. C., et al., *Luminescent quantum dots for multiplexed biological detection and imaging*. Curr Opin Biotechnol, 2002. 13(1): p. 40-6; and Gao, X. and S, Nie, *Molecular profiling of single cells and tissue specimens with quantum dots*. Trends Biotechnol, 2003. 21(9): p. 371-3). However, utilization of such multiplexing capability has been hampered by the inability to uniquely match each QD probe with the corresponding biomarker, thus yielding simultaneous detection of only a modest number of biomarkers. See for example, Chen, C., et al., *Quantum-dot-based immunofluorescent imaging of HER2 and ER provides new insights into breast cancer heterogeneity*. Nanotechnology, 2010. 21(9): p. 095101; Fountaine, T. J., et al., *Multispectral imaging of clinically relevant cellular targets in tonsil and lymphoid tissue using semiconductor quantum dots*. Modern Pathology, 2006. 19(9): p. 1181-91; Ghazani, A. A., et al., *High throughput quantification of protein expression of cancer antigens in tissue microarray using quantum dot nanocrystals*. Nano Letters, 2006. 6(12): p. 2881-6; Huang, D. H., et al., *Comparison and Optimization of Multiplexed Quantum Dot-Based Immunohistofluorescence*. Nano Research, 2010. 3(1): p. 61-68; Liu, J., et al., *Multiplexed detection and characterization of rare tumor cells in Hodgkin's lymphoma with multicolor quantum dots*. Analytical Chemistry, 2010. 82(14): p. 6237-43; Liu, J., et al., *Molecular mapping of tumor heterogeneity on clinical tissue specimens with multiplexed quantum dots*. ACS Nano, 2010. 4(5): p. 2755-65; Shi, C., et al., *Quantum dots-based multiplexed immunohistochemistry of protein expression in human prostate cancer cells*. European Journal of Histochemistry, 2008. 52(2): p. 127-34; Sweeney, E., et al., *Quantitative multiplexed quantum dot immunohistochemistry*. Biochemical and Biophysical Research Communications, 2008. 374(2): p. 181-6; Wu, X., et al., *Immunofluorescent labeling of cancer marker Her2 and other cellular targets with semiconductor quantum dots*. Nat Biotechnol, 2003. 21(1): p. 41-6; and Yezhelyev, M. V., et al., *In situ molecular profiling of breast cancer biomarkers with multicolorquantum dots*. Advanced Materials, 2007. 19(20): p. 3146-3151.

Accordingly, there is need in the art for compositions and methods for multiplex detection, identification or quantitation of analytes in sample. This disclosure provides such compositions and methods.

SUMMARY

Multiplexed staining requires unique assignment of biomarkers to corresponding detectable label probes (e.g., QD probes or other fluorescent propbes). This can be achieved either via direct QD-affinity molecule (e.g., antibody (Ab)) conjugation (covalent or non-covalent) or encoding of each Ab with a different unique encoding molecule (such as DNA or other nucleic acid) that can be identified by complementary QD-nucleic acid probe. Each strategy, suited for either 1-step or 2-step staining modalities, features its own important benefits. For example, 1-step staining with QD-Ab conjugates provides quick direct labeling of biomarkers in a stoichiometric manner.

In contrast, while multiplexed staining can become available through further optimization of direct biomarker labeling with QD-antibody probes, a two-step staining modality, where biomarker recognition with primary antibody (1'Ab) and labeling with fluorescent probes (FL probes) are done in separate steps, provides several important benefits: (i) staining conditions can be optimized for Ab and FL probe separately; (ii) FL probe size can be kept significantly smaller, as FL-Ab complex does not need to be pre-assembled prior to staining; (iii) signal amplification capability can be incorporated within the second step; and (iv) de-staining/re-staining can be performed by cycling the FL labeling step, without the need for biomarker recognition on each cycle.

Accordingly, provided herein are compositions and methods for multiplex biomarker profiling. In one aspect, provided herein is a composition comprising an affinity molecule reversibly conjugated to a label moiety. The affinity molecule can be linked to the label moiety via a linker comprising first and second strands of nucleic acid that specifically hybridize to each other. The first nucleic acid strand can be linked to the affinity molecule and the second nucleic acid strand can be linked to the nanoparticle. This allows the affinity molecule to be conjugated to the label moiety under conditions that permit hybridization between the first and second nucleic acid strands, but is not conjugated to the nanoparticle under conditions that do not permit such hybridization.

In another aspect provided herein is a composition comprising an affinity molecule reversibly conjugated to a luminescent nanoparticle, in which the nanoparticle is covalently linked to an adaptor molecule and the adaptor molecule is non-covalently linked to the affinity molecule. The affinity molecule and the adaptor molecule can be present in a 1:1 ratio. In some embodiments of this aspect, the luminescent nanoparticle is a colloidal water-soluble nanoparticle comprising a stable non-fouling coating such that non-specific binding of the nanoparticle to a cell or a tissue sample is reduced relative to a nanoparticle lacking a non-fouling coating.

In still another aspect, provided herein is a composition comprising a plurality of different affinity molecules, wherein: (i) each member of the plurality binds a different target, wherein each different affinity molecule is conjugated via different hybridized first and second nucleic acid strands to a different label moiety, wherein detectable properties of the different label moieties are distinguishable; or (ii) each member of the plurality binding a different target, wherein each different affinity molecule is conjugated to a different first single strand nucleic acid molecule that is specifically hybridized to a second single strand nucleic acid molecule, wherein the second single strand nucleic acid molecule is conjugated to a label moiety, such that each different affinity molecule is conjugated via different hybridized first and second nucleic acid strands to a different label moiety, wherein detectable properties of the different label moieties are distinguishable.

In yet another aspect, provided herein is a composition comprising a plurality of different affinity molecules, each member of the plurality binding a different target. Each different affinity molecule can be reversibly conjugated to a luminescent nanoparticle, in which the nanoparticle is covalently linked to an adaptor molecule and the adaptor molecule is non-covalently linked to the affinity molecule. The affinity molecule and the adaptor molecule can be present in a 1:1 ratio. The luminescent nanoparticle can be a colloidal water-soluble nanoparticle comprising a stable non-fouling coating such that non-specific binding of the nanoparticle to a cell or a tissue sample is reduced relative to a nanoparticle lacking a non-fouling coating. Further, emission spectra of the different luminescent nanoparticles can be distinguishable.

In yet still another aspect, described herein are solid supports bearing a plurality of different affinity molecules. Depending upon the particular embodiment, the solid support can comprise a plurality of different affinity molecules bearing, for example, nucleic acid molecules, adaptor molecules and/or label moieties in any of the various combinations or arrangements as described herein. Such solid supports can comprise samples, e.g., biological samples to be tested for the presence and/or amounts of any of a plurality of analytes. A non-limiting example of a sample on a solid support is a tissue or cell sample, e.g., a tissue section, on a slide or coverslip. Additional non-limiting examples of solid supports include, for example, a plate, dish, well, membrane, grating, bead or particle (including, but not limited to an agarose or latex bead or particle, a magnetic particle, etc.).

To fully utilize extensive multiplexing potential of fluorescent tags for molecular profiling of cells and tissue specimens and exploit the benefits of 2-step staining modality, the inventors have also developed a novel hybrid IF/FISH 2-step staining procedure featuring unique assignment of each biomarker to a corresponding fluorescent probe. This method is exemplified herein using antibody affinity molecule and quantum dot fluorescent nanoparticles, but can be generalized to other affinity molecule labels as known in the and described herein. Immunofluorescence (IF) has been widely utilized for labeling of protein biomarkers in cells and tissue specimens; however, utilization of primary antibodies (1'Ab) for biomarker recognition and fluorophore-labeled secondary antibodies (2'Ab-FL) for subsequent staining hampered multiplexing capability of this technique due to limited availability of unique 1'Ab/2'Ab pairs. At the same time, fluorescence in situ hybridization (FISH) has been optimized for multiplexed detection of DNA and mRNA, but it cannot be used for analysis of cell phenotype. In the novel hybrid IF/FISH method described herein, during the first step, biomarkers are detected by specific FAb carrying unique DNA tags, thus converting antigenicity information into DNA sequence code. During the second step, multiplexed FISH with QD- DNA or DNA-FL probes is performed, thus overcoming limitations imposed by the choice of 1'Ab/2'Ab pairs. Furthermore, multiplexing capability can be significantly expanded by using the sequential staining/imaging method described herein. Notably, hybrid IF/FISH method is equally amenable for QD-based probes as well as conventional FISH DNA-probes labeled with organic fluorophores, making this technique widely applicable to a large number of studies with different aims and parameters.

Accordingly, provided herein is also a method of analyzing a sample for a plurality of analytes. In some embodiments, the method comprises: (a) contacting the sample with a plurality of different affinity molecules under conditions that permit specific analyte binding by the different affinity molecules, wherein each different affinity molecule specifically binds a different member of the plurality of analytes, and wherein each different affinity molecule is conjugated to a different first single strand nucleic acid, such that members of the plurality of different affinity molecules become bound to members of the plurality of analytes present in the sample; (b) contacting the sample, under conditions that permit specific nucleic acid hybridization, with a first set of different second single strand nucleic acid molecules, each conjugated to a different label moiety, wherein each different second single strand nucleic acid molecule specifically hybridizes to a different first single strand nucleic acid molecule conjugated to a member of the plurality of different affinity molecules, such that at least a subset of the plurality of different affinity molecules bound to members of the plurality of analytes in the sample becomes specifically associated with a plurality of different label moieties, wherein detectable properties of the different label moieties are distinguishable; and (c) detecting signal from label moieties associated with affinity molecules bound to the sample, thereby detecting the presence or amount of at least a subset of the plurality of analytes. In some further embodiments of this, the method further comprises the steps of: (d) quenching the signal from the label moieties conjugated to the first set of second single strand nucleic acid molecules; (e) contacting the sample, under conditions that permit specific nucleic acid hybridization, with a second set of different second single strand nucleic acid molecules, each conjugated to a different label, wherein each different second single strand nucleic acid molecule specifically hybridizes to a different first single strand nucleic acid molecule conjugated to a member of the plurality of different affinity molecules, such that a different subset of the plurality of different affinity molecules bound to members of the plurality of analytes in the sample becomes specifically associated with a different plurality of different label moieties relative to those detected in step (c); (f) detecting signal from label moieties associated with affinity molecules bound to the sample, thereby detecting the presence or amount of the different subset of the plurality of analytes; and (g) optionally repeating steps (d)-(f) with a further set of second single strand nucleic acid molecules.

In some other embodiments, the method comprises: (a) contacting the sample with a first plurality of different affinity molecules under conditions that permit specific analyte binding by the different affinity molecules, wherein each different affinity molecule specifically binds a different member of the plurality of analytes, wherein each different affinity molecule is conjugated to a different first single strand nucleic acid molecule that is specifically hybridized to a second single strand nucleic acid molecule, wherein the second single strand nucleic acid molecule is conjugated to a label moiety, such that each different affinity molecule is conjugated via different hybridized first and second nucleic acid strands to a different label moiety and members of the plurality of different affinity molecules become bound to members of the plurality of analytes present in the sample, wherein detectable properties of the label moieties are distinguishable; and (b) detecting signal from label moieties associated with first plurality of affinity molecules bound to the sample, thereby detecting the presence or amount of the plurality of analytes. In some further embodiments of this, the method further comprises: (c) quenching the signal from the label molecules conjugated to the first set of second single strand nucleic acid molecules; (d) contacting the sample with a second plurality of different affinity molecules under conditions that permit specific analyte binding by the different affinity molecules; є detecting signal from label moieties associated with second plurality of affinity molecules bound to the sample, thereby detecting the presence or amount of at least a subset of the plurality of analytes; and (f) optionally repeating steps (c)-(e) with a further second set of the affinity molecules.

In yet some other embodiments, the method comprises: (a) contacting the sample with a first plurality of different affinity molecules under conditions that permit specific analyte binding by the different affinity molecules, wherein each different affinity molecule specifically binds a different member of the plurality of analytes and members of the plurality of different affinity molecules become bound to members of the plurality of analytes present in the sample, wherein each different affinity molecule is reversibly conjugated to a different luminescent nanoparticle, in which the nanoparticle is covalently linked to an adaptor molecule and the adaptor molecule is non-covalently linked to the affinity molecule, the affinity molecule and the adaptor molecule are present in a 1:1 ratio, and wherein the luminescent nanoparticle is a colloidal water-soluble nanoparticle comprising a stable non-fouling coating such that non-specific binding of the nanoparticle to a cell or a tissue sample is reduced relative to a nanoparticle lacking a non-fouling coating, and detectable properties of the luminescent nanoparticles are distinguishable; and (b) detecting signal from luminescent nanoparticles associated with the first plurality of affinity molecules bound to the sample, thereby detecting the presence or amount of the plurality of analytes. In some further embodiments of this, the method further comprises: c) quenching the signal from the luminescent nanoparticles conjugated to the first set of different second single strand nucleic acid molecules; (d) contacting the sample with a second set of the plurality of different affinity molecules under conditions that permit specific analyte binding by the different affinity molecules; (e) detecting signal from luminescent molecules associated with the second set of affinity molecules bound to the sample, thereby detecting the presence or amount of at least a subset of the plurality of analytes; and (f) optionally repeating steps (c)-(e) with a further second set of the affinity molecules.

BRIEF DESCRIPTION OF THE DRAWINGS

FIG. 12A, bright nuclear AR staining is achieved with Ab/SpA-DNA and QD-DNA probes. FIG. 12B, signal drop of up to 60-80% could be achieved. Further improvement of de-staining procedure can be achieved by quenching or removing residual non-specifically bound QD probes

FIG. 14A, universal QD/SpA platform that can be used for 1-step purification-free assembly of functional QD-Ab probes via capture of free antibodies from solution by SpA. Once bound, Ab cannot be exchanged with other QD/SpA probes, thus enabling mixing of multicolor probes within a single cocktail (FIG. 14B) for a 1-step parallel multiplexed staining (FIG. 14C). In this procedure, each QD-Ab probe specifically labels corresponding biomarker without showing interference or cross-talk with other probes. FIG. 14D, spectral imaging can be used for unmixing the individual QD peaks, quantitative analysis of biomarker expression, and depiction of relative biomarker distribution within the specimen. FIG. 14E, brief washing with low-pH buffer yields complete specimen de-staining, thus enabling another cycle of parallel multiplexed staining. FIG. 14F, sequential repetition of N-biomarker parallel staining for M cycles enables labeling of N×M biomarkers. With utilization of QD probes featuring narrow emission profiles, molecular profiling for over 100 biomarkers can be achieved.

FIGS. 18A and 18B, at high analyte concentration (100 nM) fast saturation of surface binding sites was observed, thus leading to analyte capture via weak binding in addition to strong interactions. As a result, quick initial dissociation of analyte accounting to nearly 5% loss was detected (likely due to breaking of weak interactions) followed by very slow dissociation kinetics. FIG. 18C, at low analyte concentration (10 nM) only slow dissociation was observed. Overall retention of 97% bound analyte after 1 hour of washing confirmed sufficient stability of SpA-Ab bond within the time-frame of staining experiment.

FIG. 21A, characteristic nuclear staining was obtained with QD545/SpA probes pre-assembled with anit-AR antibody. FIG. 21B, brief incubation with pH2 Glycine-HCl/0.1% casein buffer achieved complete specimen de-staining, leaving no detectable QD fluorescence signal. FIG. 21C, re-staining of cells with anti-AR QD545/SpA-Ab probe during the second cycle yielded nearly complete restoration of fluorescence signal, indicating that all biomarkers were vacated during de-staining procedure. FIG. 21D, another re-staining with non-functionalized QD545/SpA probes produced only background staining, confirming that no vacant 1' antibodies were left on the specimen and, thus, ensuring no cross-talk between staining cycles. Same sub-population of cells was imaged after each step using consistent imaging parameters to aid in direct comparison of staining intensity and distribution. Scale bar, 50 μm.

FIG. 23A, AR staining with Alexa Fluor568-labeled QD/SpA-Ab probes showed characteristic nuclear staining pattern with both Wide UV (QD channel, left) and Rhodamine LP (Alexa Fluor568 channel, right) filter cubes. FIG. 23B, after de-staining with pH2 Glycine-HCl/0.1% casein buffer QD signal was completely eliminated due to probe elution and quenching, while Alexa Fluor568 staining highlighted diffuse distribution of residual non-specifically bound QD/SpA probes. FIG. 23C, cross-linking of QD/SpA-Ab probes to biomarkers did not affect staining pattern or intensity. However, following de-staining (FIG. 23D) cross-linked probes could not be eluted, as indicated by retained Alexa Fluor568 signal, assigning removal of QD signal solely to low-pH-mediated quenching. Scale bar, 50 μm.

FIG. 25A, high-magnification microscopy of AR staining after 1 and 10 degradation cycles revealed only a minor loss of signal intensity with preserved nuclear biomarker localization. To aid in signal intensity comparison, spectral imaging and unmixing (right panels) was used to extract QD signal and remove background autofluorescence present in true-color images (left panels). Scale bar, 50 u.m. FIG. 25B, quantitative analysis of AR staining intensity showed no more than 10% signal loss due to cyclic low-pH treatment. Some variability in AR staining between different cells was observed, which could be assigned to natural variability in biomarker expression. FIG. 25C, qualitative comparison of unmixed low-magnification images of cells exposed to different number of degradation cycles correlates well with quantitative analysis in (FIG. 25B) and shows good preservation of biomarker antigenicity for at least 10 staining cycles. Scale bar, 250 μm.

DESCRIPTION OF EXEMPLARY EMBODIMENTS

Figure 1:
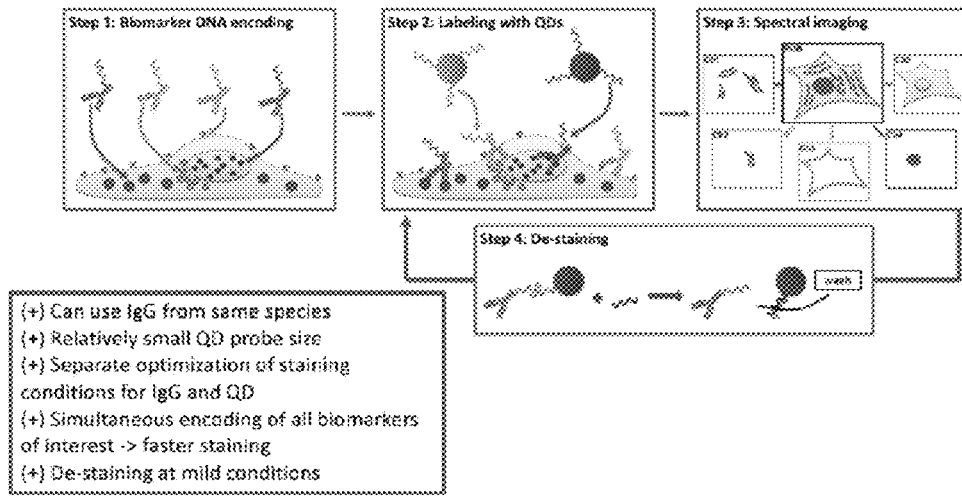
FIG. 1 is a schematic representation of an embodiment of the hybrid IF/FISH procedure for multiplexed 2-step cell staining. In the first step, biomarkers of interest are simultaneously encoded by unique DNA tags via labeling with 1'Ab-DNA conjugates. On the second step a subset of biomarkers is labeled with complementary QD-DNA probes. Subsequently, spectral imaging is used to unmix and quantify staining produced by individual QD probes. Finally, incubation with a longer oligonucleotide leads to DNA bond displacement and QD-DNA probe dissociation, thus achieving specimen de-staining for the next staining cycle. Notably, de-staining does not remove the first layer of Ab-DNA tags, thus eliminating the need for biomarker re-detection on each staining cycle.

In-depth understanding of the nature of cell physiology and ability to diagnose and control the progression of pathological processes heavily rely on untangling the complexity of intracellular molecular mechanisms and pathways. Therefore, comprehensive molecular profiling of individual cells within the context of their natural tissue or cell culture microenvironment is required. In principle, this goal can be achieved with immunofluorescence staining and imaging by tagging each biomarker with a unique fluorescent probe and detecting its localization with high sensitivity at sub-cellular resolution. Yet, neither widely used conventional techniques nor more advanced nanoparticle-based methods have been able to address this task up to date. High multiplexing potential of fluorescent probes is significantly restrained by the inability to uniquely match probes with corresponding biomarkers. This issue is especially relevant for quantum dot probes—while simultaneous spectral imaging of up to 10 different probes is possible, only a few can be used concurrently for staining with existing methods. To fully utilize multiplexing potential of label moieties or fluorescent labels, exemplified herein by quantum dots fluorescent nanoparticles (QDs), it is necessary to design new staining methods featuring unique assignment of each biomarker to a corresponding QD probe. The Hybrid IF/FISH procedure described here achieves this objective by encoding each biomarker with a unique nucleic acid (e.g. DNA) tag, thus converting IF into a highly multiplexable FISH-like staining method. Furthermore, multiplexing capability of this method can be expanded by performing several staining cycles in a sequential manner with no interference between different cycles. The method is directly applicable for a wide range of molecular profiling studies. Utilization of the compositions and methods described herein can benefit both biomedical research and clinical diagnostics by providing a tool for addressing phenotypic heterogeneity within large cell populations, opening access to studying low-abundance events often masked or completely erased by batch processing, and elucidating biomarker signatures of diseases critical for accurate diagnostics and targeted therapy.

Accordingly, described herein are compositions and methods for detecting and/or quantitating biomarkers in a biological sample, e.g., a cellular biological sample, whether comprising isolated cells or cells in a tissue sample. The compositions and methods described herein are well suited to assay the presence or level of a plurality of biomarkers simultaneously. In one aspect, compositions and methods are described in which affinity moieties specific for a plurality of target biomarkers are coupled, either directly or indirectly, to label moieties such that each biomarker is paired with a corresponding label moiety via a corresponding affinity molecule. The biomarker/label moiety pairing for this aspect and others described herein is reversible as that term is defined herein.

As noted, the reversible coupling between affinity molecule and label moiety can be indirect or direct. Both the indirect and direct approaches are described in more detail herein below, and each has properties beneficial in certain applications described herein.

One approach to indirect coupling takes advantage of the information-carrying capacity of nucleic acid sequences to uniquely encode the coupling of affinity molecule to label moiety. In this approach, the affinity molecule and label moiety are each coupled to a separate complementary strand of nucleic acid, such that hybridization of the separate, complementary strands reversibly couples, links or conjugates the affinity molecule to the label moiety. This approach has the advantage that the exacting specificity of nucleic acid hybridization permits a large number of different affinity molecules to be coded with different nucleic acids, each specific for only one corresponding complementary sequence joined to a respective different label moiety. When applied to a sample simultaneously, the affinity molecules specifically bind their respective biomarker targets present on the sample, and the hybridization of the complementary nucleic acid sequences links the different label moieties to the different affinity molecules in a way that permits multiplex detection. The coupling is reversible by any approach that separates hybridized strands of nucleic acid, e.g., displacement by competing complementary sequence, heating, changes in salt concentration, etc. as described elsewhere herein.

One approach to direct coupling of affinity molecule and label moiety takes advantage of the strong, specific, non-covalent binding of the constant domains of antibody affinity molecules by certain polypeptides. As but one example (others are provided herein below), the S. aureus Protein A (SpA) polypeptide tightly binds immunoglobulin molecules via determinants on their constant domains. In this aspect, an antibody can be reversibly coupled to a label moiety by coupling the label moiety to SpA, and then mixing the label-SpA complexes with the antibody to effect linkage of the antibody and label moiety through the SpA.

Various aspects and embodiments employing either the indirect or direct coupling of affinity molecule and label moiety are described in further detail herein below that each permit multiplex detection and/or quantitation of biomarker molecules in a cellular sample. The various components and considerations necessary for these biomarker detection compositions and methods are described in the sections that follow.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the terms "comprising" or "comprises" means "including" or "includes" and are used in reference to compositions, methods, and respective component(s)

thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, the term "linker" means an organic moiety that connects two parts of a compound. Linkers typically comprise a direct bond or an atom such as oxygen or sulfur, a unit such as $NR^1$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

As used herein, the term "nucleic acid linker" refers to a nucleic acid that connects two parts of a compound, e.g., an affinity molecule to a label moiety. A nucleic acid linker can be single-stranded, fully double-stranded, or partially double-stranded. A nucleic acid linker can be any length. For example, a nucleic acid linker can be from 1 nucleotide to about 100 nucleotides in length. When the nucleic acid linker is double-stranded, the linker can comprise a double stranded region of about 6 to about 100 consecutive base pairs. However, the duplex region can be interrupted by one or more single-stranded regions in one or both of the strands of the duplex. Further, a double-stranded nucleic acid linker can comprise a single-stranded overhang on one or both ends of the double-stranded region. Moreover, a nucleic acid linker can comprise one or more nucleic acid modifications described herein. A nucleic acid linker can be attached to a compound by a non-nucleic acid linker.

As used herein, the term "non-nucleic acid linker" refers to any linker that is not a nucleic acid linker.

Compositions

In one aspect, provided herein is a composition comprising an affinity molecule reversibly conjugated to a label moiety. As used herein, the term "reversibly conjugated" means that the two parts are conjugated by non-covalent bonding only. Generally such non-covalent bonding comprises one or more of hydrogen bonding, Van der Waals forces, electrostatic forces, hydrophobic forces, and the like. As such, reversible conjugation does not require breaking of a covalent bond to remove or separate the affinity molecule from the label moiety.

The affinity molecule and the label moiety can be present in any ratio in the composition. For example, the affinity molecule and the label moiety can be in a ratio from about 1:1 to about 1:100, from about 1:1 to about 1:50, from about 1:1 to about 1:25, from about 1:1 to about 1:20, or from about 1:1 to about 1:15 (affinity molecule:label moiety). In some embodiments, the affinity molecule and the label moiety can be in a ratio of about 1:1, 1:2, 1:3, 1:4, 1:5, 1:6, 1:7, 1:8, 1:9, or 1:10. Generally, when the composition is to be used for quantitative labeling or detection of a target molecule in a sample, the affinity molecule and the label moiety are in a 1:1 ratio. On the other hand, when the composition is to be used for qualitative labeling or detection of a target molecule in a sample, a higher number of label moieties per affinity molecule can be used to provide signal amplification.

The affinity molecule can be conjugated with more than one first nucleic acid strands. For example, the affinity molecule can be conjugated with one, two, three, four, five, six, seven, eight, nine, ten or more first nucleic acid strands. When the affinity molecule is conjugated with two or more first nucleic acid strands, the first nucleic acid stands can all be the same, all different, or some same and some different. In some embodiments, the affinity molecule is conjugated with one first nucleic acid strand, i.e., the affinity molecule and the conjugated first nucleic acid strand have a 1:1 ratio. Generally, when the composition is to be used for quantitative labeling or detection of a target molecule in a sample, the affinity molecule and the first nucleic acid strand are in a substantially 1:1 ratio. On the other hand, when the composition is to be used for qualitative labeling or detection of a target molecule in a sample, affinity molecule can be conjugated with two or more first nucleic acid strands to provide signal amplification.

The label moiety can also be conjugated with more than one second nucleic acid strand. For example, the label moiety can be conjugated with one, two, three, four, five, six, seven, eight, nine, ten or more second nucleic acid strands. When the label moiety is conjugated with two or more second nucleic acid strands, the second nucleic acid stands can all be the same, all different, or some same and some different. In some embodiments, the label moiety is conjugated with one second nucleic acid strand, i.e., the label moiety and the conjugated second nucleic acid strand have a substantially 1:1 ratio.

In some embodiments, the affinity molecule is conjugated to the label moiety via a nucleic acid linker. In some embodiments, the nucleic acid linker comprises first and second strands of nucleic acid (i.e., a nucleic acid linker) that specifically hybridize to each other. The affinity molecule and the label moiety can be attached to different nucleic acid strands. For example, the affinity molecule can be bound to a first strand of the nucleic acid linker and the label moiety can be attached to the second strand of the nucleic acid linker. Thus, the affinity molecule can be conjugated to a label moiety molecule under conditions that permit hybridization between the first and second nucleic acid strands. However, the affinity molecule is not conjugated to the lab molecule under conditions that do not permit such hybridization. As described in more detail below, the affinity molecule or the label moiety can be linked to the respective nucleic acid strand covalently or non-covalently.

As used herein, the term "specifically hybridize" refers to the ability of a nucleic acid molecule to hybridize, under moderately or highly stringent conditions, to a desired nucleic acid molecule, without substantial hybridization under the same conditions with nucleic acid molecules that are not the desired nucleic acid molecule. Those skilled in the art can readily determine whether the first nucleic acid strand hybridizes to the second nucleic acid strand under stringent conditions by performing a hybridization assay in the presence of other nucleic acid molecules, such as total cellular nucleic acid molecules, and detecting the presence or absence of hybridization to the other nucleic acid molecules. The terms "hybridize" and "hybridization" refer to the formation of complexes between nucleotide sequences which are sufficiently complementary to form complexes via Watson-Crick base pairing.

As used herein the term "stringent conditions" refers to conditions under which a nucleic acid strand will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes between complementary nucleic acid strands, e.g., between DNA probes and complementary targets in a sample or between a PCR primer and a nucleic acid molecule to be amplified with a substantial lack of duplexes formed between non-complementary nucleic acid strands.

Suitable stringent hybridization buffers and conditions are well known to those of skill in the art and are described, for example, in Sambrook et al., *Molecular Cloning: A Laboratory Manual*, Cold Spring Harbor Laboratory, New York (1992) and in Ausubel et al., *Current Protocols in Molecular Biology*, John Wiley and Sons, Baltimore, Md. (1998).

In some embodiments, non-stringent conditions can be used. Without wishing to be bound by a theory, due to DNA linker design (each pair is significantly different than others with no more than 4 bp hetero-dimer), non-stringent conditions can also be used for specifically binding a nucleic acid strands with its complementary binding partner. Non-stringent conditions can include standard biological buffers, such as PBS or TBS, with physiological ionic strength and pH. The term "physiological ionic strength" is well known to those skilled in the art. It is generally equivalent to about 137 mM NaCl, 3 mM KCl and about 10 mM phosphate. Physiological pH is about 7.4.

In some embodiments, the affinity molecule is conjugated to the label moiety via an adaptor molecule, in which the label moiety is covalently linked to the adaptor molecule via a non-nucleic acid linker and the adaptor molecule is non-covalently linked to the affinity molecule. The non-covalent binding between the affinity molecule and the adaptor molecule can be disrupted and the label moiety disassociated from the affinity molecule. Thus, the affinity molecule can be conjugated to the label moiety molecule under conditions that permit non-covalent binding between the affinity molecule and the adaptor molecule, but is not conjugated to the label moiety under conditions that do not permit such non-covalent binding.

When the conjugation is via an adaptor molecule, the adaptor molecule and the affinity molecule can be present in any ratio in the composition. For example, the adaptor molecule and the affinity molecule can be in a ratio from about 1:1 to about 1:100, from about 1:1 to about 1:50, from about 1:1 to about 1:25, from about 1:1 to about 1:20, or from about 1:1 to about 1:15 (affinity molecule:adaptor molecule). In some embodiments, the adaptor molecule and the affinity molecule can be in a ratio about 1:1, 1:2, 1:3, 1:4, 1:5, 1:6, 1:7, 1:8, 1:9, or 1:10. In some embodiments, it can be useful to limit the adaptor molecule to affinity molecule ratio in order to increase the stability of the complex. High stability of the complex can be advantageous to avoid cross-talk and/or rearrangement between different affinity molecules bound to adaptor molecules. For example, *Staphylococcus* protein A (SpA) has four immunoglobulin binding sites, but the stability of immunoglobulin to SpA binding is greater when there are two, or even one immunoglobulin per SpA molecule, as opposed to four immunoglobulin molecules per SpA. Thus, in some embodiments, an adaptor molecule to affinity molecule ratio of 1:1 or not more than 1:2 can be useful. Put slightly differently, it can be useful to have an adaptor molecule to affinity molecule ratio of 1:2 or less. It is noted that when preparing pre-assembled affinity molecule:adaptor molecule conjugates, one can actually include a ratio of less than one affinity molecule per adaptor molecule in order to limit the number of affinity molecules conjugated per adaptor molecule.

The inventors have discovered that binding of no more than 1 affinity molecule to an adaptor molecule forms a stable bond that shows slow dissociation kinetics. In some embodiments, the stable bond shows very little or no dissociation within 2-4 hours. For example, less than 5%, less than 10%, less than 15%, less than 20%, less than 25%, less than 30%, less than 35%, less than 40%, less than 45%, or less than 50% of the affinity molecule—adaptor molecule complex is dissociated in 12 hours, 10 hours, 9 hours, 8 hours, 8 hours, 6 hours, 5 hours, 4 hours, 3 hours, 2 hours or 1 hour. In other words, at least 50%, at least 55%, at least 60%, at least 65%, at least 70%, at least 75%, at least 80%, at least 85%, at least 90% or atleast 95% of the affinity molecule—adaptor molecule is still in the form of a complex after 12 hours, 10 hours, 9 hours, 8 hours, 8 hours, 6 hours, 5 hours, 4 hours, 3 hours, 2 hours or 1 hour.

Nucleic Acid

As used herein, the term "nucleic acid" refers to a polymer or oligomer of nucleotide or nucleoside monomers consisting of naturally occurring bases, sugars and inter-sugar linkages. The term "nucleic acid" also includes polymers or oligomers comprising non-naturally occurring monomers, or portions thereof, which function similarly. At a minimum, a nucleic acid useful in the compositions and methods described herein for coupling an affinity molecule and label moiety is capable of sequence specific hydrogen-bonded hybridization between complementary nucleic acid strands. A nucleic acid can be DNA, RNA or chimeric, i.e., comprising both deoxy- and ribo-nucleotides.

The affinity molecule can be conjugated to the first strand of the nucleic acid linker at any position in the first nucleic acid strand. For example, the affinity molecule can be conjugated to the 3' or 5' end of the first nucleic acid strand. Similarly, the label moiety can be conjugated at any position in the second nucleic acid strand. For example, the label moiety can be conjugated to the 3' or 5' end of the second nucleic acid strand. Generally, the affinity molecule and the label moiety are conjugated to the nucleic acid strand at positions such that hybridizing the two strands does not interfere with functioning of the affinity molecule or the label moiety. Accordingly, in some embodiments, the affinity molecule is conjugated to the 3' terminus of the first nucleic acid strand and the label moiety is conjugated to the 3' terminus of the second nucleic acid strand. In other embodiments, the affinity molecule is conjugated to the 5' terminus of the first nucleic acid strand and the label moiety is conjugated to the 5' terminus of the second nucleic acid strand. One or both strands of the double-stranded nucleic acid can comprise a modification. When both strands comprise a modification, such a modification can be the same or different.

As indicated above, the affinity molecule or the label moiety can be linked to the respective nucleic acid strand covalently or non-covalently. Accordingly, in some embodiments, the affinity molecule and the first strand of the nucleic acid linker are covalently linked together using a non-nucleic acid linker. For example, the affinity molecule and the first stand of the nucleic acid linker can be covalently linked together via a linker selected from the group consisting of a bond, succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond (from S-HyNic/S-4FB reaction), zero-length peptide bond (between —COOH and —NH2 directly on affinity molecule and nucleic acid), two peptide bonds on a spacer (from cross-linking of two —NH2 groups), triazole bond (from "click" reaction), a phosphodiester linkage, a phsophothioate linkage, and any combination thereof.

Alternatively, the affinity molecule and the first stand of the nucleic acid linker can be non-covalently linked together via an adaptor molecule, in which the adaptor molecule binds non-covalently with the affinity molecule and the first strand of the nucleic acid is conjugated (covalently or non-covalently) with the adaptor molecule. For example, the first strand of the nucleic acid can be covalently linked to the adaptor molecule by a linker selected from the group consisting of a bond, succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond (from S-HyNic/S-4FB reaction), zero-length peptide bond (between —COOH and —NH2 directly on affinity molecule and nucleic acid), two peptide bonds on a spacer (from cross-linking of two —NH2 groups), triazole bond (from "click" reaction), a phosphodiester linkage, a phsophothioate linkage, and any combination thereof.

The label moiety and the second strand of the nucleic acid linker can be covalently linked together via a linker selected from the group consisting of a bond, succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond (from S-HyNic/S-4FB reaction), zero-length peptide bond (between —COOH and —NH$_2$ directly on affinity molecule and nucleic acid), two peptide bonds on a spacer (from cross-linking of two —NH2 groups), triazole bond (from "click" reaction), a phosphodiester linkage, a phsophothioate linkage, and any combination thereof.

Alternatively, the label moiety and the second strand of the nucleic acid linker can be non-covalently linked together via a coupling pair in which the label moiety can be linked to one member of the coupling pair and the second stand of the nucleic acid can be linked to other member of the coupling pair. For the label moiety can be linked to either streptavidin or biotin and the affinity molecule can be bound to the other, e.g., if the label moiety is bound to streptavidin then the affinity molecule is linked to biotin and vice versa.

The nucleic acid strand conjugated with the label moiety can comprise additional molecules conjugated to it. In some embodiments, the nucleic acid strand conjugated with the label moiety does not comprise any additional molecule which can quench a detectable signal from the label moiety. For example, the nucleic acid strand conjugated with the label moiety does not comprise any additional molecule that can act as a fluorophore acceptor.

Each nucleic acid strand can be independently from about 6 to about 50 nucleotides in length or more. What should be considered is the length necessary to provide specific pairing with a complementary nucleic acid strand that is stable under the conditions employed for label binding and detection. Generally, the more different affinity molecules included, the higher temperature or lower the salt concentration, the longer the sequence will need to be to provide specificity and stability sufficient for a given assay. For example, each strand can be independently about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, at least one nucleic acid strand is about 11 nucleotides in length. In some embodiments, at least one nucleic acid strand is about 21 nucleotides in length.

The first and second strands of the nucleic acid linker can hybridize over at least part of their length to form a double-stranded region that is stable under moderately or highly stringent conditions. For example, the first and second strand of the nucleic acid can hybridize to form a double-stranded region that is stable at low temperatures but is unstable at high temperatures, i.e., the double-stranded region has a high melting temperature (Tm). For example, the first and second strand of the nucleic acid can hybridize to form a double-stranded region having a Tm of 30° C. or higher (e.g., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C. or higher). One of skill in the art is well aware of computational and experimental methods for determining the melting temperature of double stranded nucleic acids.

The first and second strand of the nucleic acid can hybridize to form a double-stranded region of about 6 to about 30 consecutive base-pairs. However, the double-stranded region can be interrupted by one or more (e.g., one two, three or more) single-stranded nucleotides in one or both of the strands. This can be useful in dissociating the label moiety from the affinity molecule, if needed. When both strands comprise single-stranded nucleotide(s) in the double-stranded region, they can be opposite to each other (i.e., forms a mismatch) or not next to each other (i.e., forms a bulge, loop, or hairpin).

In some embodiments, the first and second strand of the nucleic acid can hybridize to form a double-stranded region of about 10-18 base-pairs. In some embodiments, the first and second strand of the nucleic acid can hybridize to form a double-stranded region of about 12-16 base-pairs. In some embodiments, the first and second strand of the nucleic acid can hybridize to form a double-stranded region of about 11 base-pairs. The double-stranded nucleic acid linker can also comprise a single stranded overhang of about 1 to about 25 nucleotides, (e.g., 1, 2, 3, 4, 5, 6, 7, 8, 9, 10, 11, 12, 13, 14, 15, 16, 17, 18, 19, 20, 21, 22, 23, 24 or 25). As used herein, the term "overhang" refers to a double-stranded structure where at least one end of one strand is longer than the corresponding end of the other strand forming the double-stranded structure. The single-stranded overhang can be located at the 3' or the 5' end of either strand. The double-stranded nucleic acid can also have a blunt end, i.e., no single-stranded over hang. A single-stranded overhang can be used to facilitate or dissociating the label moiety from the affinity molecule via strand-displacement with a longer complementary sequence that that hybridized to join the affinity molecule and label moiety. Strand-displacement is discussed in more detail below.

As stated above, the term "nucleic acid" also includes polymers or oligomers comprising non-naturally occurring monomers, or portions thereof, which function similarly. Accordingly, in some embodiments, the nucleic acid comprises at least one modification. Typical nucleic acid modifications can include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the sugar, e.g., at the 2' position of the sugar; (iii) wholesale replacement of the phosphate moiety with "dephospho" linkers; (iv) modification or replacement of a naturally occurring base with a non-natural base; (v) replacement or modification of the ribose-phosphate backbone, e.g. peptide nucleic acid (PNA); (vi) modification of the 3' end or 5' end of the nucleic acid, e.g., removal, modification or replacement of a terminal phosphate group or conjugation of a moiety, e.g., conjugation of a ligand, to either the 3' or 5' end of nucleic acid; and (vii) modification of the sugar, e.g., six membered rings.

In some embodiments, the nucleic acid is not modified relative to naturally-occurring nucleic acid molecules.

The terms replacement, modification, alteration, and the like, as used in this context, do not imply any process limitation, e.g., modification does not mean that one must start with a reference or naturally occurring nucleic acid and modify it to produce a modified nucleic acid but rather "modified" simply indicates a difference from a naturally occurring molecule.

In some embodiments, the modification is selected from the group consisting of nucleobase modifications, sugar modification, inter-sugar(or inter-nucleoside) linkage modifications, backbone modifications (or sugar-phosphodiester replacement), and any combinations thereof. Exemplary sugar modifications at the sugar moiety include but are not limited to, modifying the 2' position of the sugar, such as 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—$CH_2$-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'—$NH_2$, and 2-SH; arabinose sugar; threose sugar; and acyclic sugar (e.g., glycol nucleic acids).

Exemplary inter-sugar linkage and backbone modifications include, but are not limited to, replacing one or both of the non-bridging phosphate oxygen atoms in the intersugar linkage can be replaced by the following: S, Se, $BR_3$ (R is hydrogen, alkyl, aryl), C (i.e. an alkyl group, an aryl group, etc. . . . ), H, $NR_2$; replacing one or both of bridging oxygen, (i.e. oxygen that links the phosphate to the nucleoside), with nitrogen (bridged phosphoroamidates), sulfur (bridged phosphorothioates) or carbon (bridged methylenephosphonates); replacing the phosphate group with amides (for example amide-3 (3'-$CH_2$—C(=O)—N(H)-5') and amide-4 (3'-$CH_2$—N(H)—C(=O)-5')), hydroxylamino, siloxane (dialkylsiloxxane), carboxamide, carbonate, carboxymethyl, carbamate, carboxylate ester, thioether, ethylene oxide linker, sulfide,sulfonate, sulfonamide, sulfonate ester, thioformacetal (3'-S—$CH_2$—O-5'), formacetal (3'-O—$CH_2$—O-5'), oxime, methyleneimino, methykenecarbonylamino, methylenemethylimino (MMI, 3'-$CH_2$—N($CH_3$)—O-5'), methylenehydrazo, methylenedimethylhydrazo, methyleneoxymethylimino, ethers (C3'-O—C5'), thioethers (C3'-S—C5'), thioacetamido (C3'-N(H)—C(=O)—$CH_2$—S—C5'), C3'-O—P(O)—O—SS—C5', C3'-$CH_2$—NH—NH—C5', 3'—NHP(O)($OCH_3$)—O-5' and 3'—NHP(O)($OCH_3$)—O-5'; and replacing the phosphate linker and sugar by nuclease resistant nucleoside or nucleotide surrogates, such as morpholino, cyclobutyl, pyrrolidine, peptide nucleic acid (PNA), aminoethylglycyl PNA (aegPNA), and backnone-extended pyrrolidine PNA (bepPNA) nucleoside surrogates.

While one or both strands of the nucleic acid linker can comprise ribonucleotides, in some embodiments it is preferred that a strand is not comprised of all ribonucleotides. For example, a strand can comprise one, two, three, four, five, six, seven, eight, nine, ten, or more ribonucleotides as long as there is at least one (e.g., one, two, three, four, five, six, seven, eight, nine, ten, or more) 2'-deoxynucleotides in the strand. If more than one ribonucleotide is present, they can be present consecutively, i.e., next to each other, or non-consecutively.

Label Moiety

As used herein, the term "label moiety" refers to any molecule that has a detectable property or is capable of producing a detectable signal. The term "detectable property" means a physical or chemical property of a molecule that is capable of independent detection or monitoring by an analytical technique after being conjugated with an affinity molecule, i.e., the property is capable of being detected in the presence of a sample under analysis. The property can be light emission after excitation, quenching of a known emission sites, electron spin, radio activity (electron emission, positron emission, alpha particle emission, etc.), nuclear spin, color, absorbance, near IR absorbance, UV absorbance, far UV absorbance, etc. Suitable label moieties include fluorescent molecules, luminescent molecules and nanoparticles, radioisotopes, chromophores, nucleotide chromophores, enzymes, substrates, chemiluminescent moieties, magnetic microbeads, magnetic nanoparticles, plasmonic nanoparticles, upconverting nanoparticles, bioluminescent moieties, nanoparticles comprising fluorescent molecules, nanoparticles comprising fluorophores, and the like. Means of detecting such labels are well known to those of skill in the art. For example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label. As such, a label moiety is any moiety detectable by spectroscopic, photochemical, biochemical, immunochemical, electrical, optical or chemical means. Any method known in the art for detecting the particular label moiety can be used for detection.

The term "analytical technique" means an analytical chemical or physical approach or instrument for detecting and/or monitoring the property. Such instruments can be based on spectroscopic analytical methods such as UV and visible light spectrometry, far IR, IR and near IR spectrometry, X-ray spectrometry, electron spin resonance spectrometry, nuclear magnetic resonance (NMR) spectrometry, etc.

In some embodiments, the label moiety is a luminescent nanoparticle. As used herein, the term "luminescent nanoparticle" refers to luminescent materials that generate light upon the combination of holes and electrons. Luminescent nanoparticles are generally nanocrystals such as quantum dots, nanorods, nanobipods, nanotripods, nanomultipods or nanowires.

Luminescent nanoparticles can be made from compound semiconductors which include Group II, Group III, group IV, Group V, or Group VI materials. For example, Luminescent nanoparticles can be made from compound semiconductors which include Group II-VI, II-IV and III-V materials. Exemplary luminescent nanoparticles include, but are not limited to cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and the like.

The luminescent nanoparticles can be core type or core-shell type. In a core-shell nanoparticle, the core and shell are made from different materials. Both core and shell can be made from compound semiconductors. In some embodiments, the luminescent nanoparticle comprises a core; and a shell forms a colloidal particle. Without wishing to be bound by a theory, colloidal properties can come from surface coating. Inorganic shell only confines electrons/holes to the core for improved fluorescent properties. In some embodiments, the luminescent nanoparticle core comprises CdSe and the shell comprises ZnS.

The shape of the luminescent nanoparticle is not limited and can be in the shape of a sphere, a rod, a wire, a pyramid, a cube, or other geometric or non-geometric shapes. Additionally, the particle size of the luminescent nanoparticle is typically from about 1 nm to about 1000 nm. For example, the luminescent nanoparticle can be from about 1 nm to about 100 nm, or from about 1 nm to about 50 nm in size. In some embodiments, the luminescent nanoparticle is from about 2 nm to about 25 nm in size. In some embodiments, the luminescent nanoparticle can be about 10 nm in size.

In some embodiments, hydrodynamic size of the luminescent nanoparticle in aqueous buffer can range from about 5 nm to about 30 nm. As used herein, "hydrodynamic size" refers to the apparent size of a molecule based on the diffusion of the molecule through an aqueous solution. The diffusion or motion of the molecule through solution can be processed to derive an apparent size of the molecule, where the size is given by the "Stokes radius" or "hydrodynamic radius" of the molecule. The "hydrodynamic size" of a molecule depends on both mass and shape (conformation), such that two molecules having the same mass may have differing hydrodynamic sizes based on the overall conformation. Hydrodynamic size can be measured, for example, by size exclusion chromatography.

The color of the light emitted by the luminescent nanoparticle depends on a number of factors that include the size and shape of the luminescent nanoparticle. As is in known in the art, luminescent nanoparticles having the same composition but having different diameters absorb and emit radiation at different wave lengths. For example, a luminescent nanoparticle with a larger particle size emits light with a lower energy as compared to a luminescent nanoparticle made of the same material but with a smaller particle size. Thus, the small luminescent nanoparticles absorb and emit in the blue portion of the spectrum, whereas the medium and large quantum dots absorb and emit in the green and red portions of the visible spectrum, respectively. It is to be noted that unlike organic fluorophores, QDs can absorb all light with energy higher than the band-gap (i.e. wavelengths lower than emission wavelength): larger QDs absorb blue light very efficiently.

Alternatively, or in addition, the luminescent nanoparticles can be essentially the same size but made from different materials. For example, UV-absorbing luminescent nanoparticles can be made from zinc selenide, whereas visible and IR luminescent nanoparticles can be made from cadmium selenide and lead selenide, respectively. Nanoparticles having different size and/or composition can be used in each of the nanoparticle layers.

Emission spectra of different luminescent nanoparticles are distinguishable. For example, emission spectra of a first luminescent nanoparticle can have a peak emission wavelength that differs by least 5 nm, at least 10 nm, at least 15 nm, at least 20 nm, at least 25 nm, at least 30 nm, at least 35 nm, at least 40 nm, at least 45 nm, or at least 50 nm from the peak emission wavelength of a second nanoparticle.

The luminescent nanoparticles are typically hydrophobic in nature. Accordingly, luminescent nanoparticles can be coated with a polymer to provide desirable properties to the luminescent nanoparticles. For example, coating the luminescent nanoparticle can aid in allowing the luminescent nanoparticle to exist in an aqueous medium while retaining its optical properties. A coating can also provide functional groups for conjugating the nanoparticle with a molecule, such as a nucleic acid or an adaptor molecule. The luminescent nanoparticles can be coated with an amphiphilic polymer or lipids. Surface can be made positively charged, negatively charged, neutral, or zwitterionic.

In some embodiments, the luminescent nanoparticle comprises a polyethylene glycol (PEG) coating layer. As used herein, the term "polyethylene glycol" refers to a polymer containing ethylene glycol monomer units of formula —O—CH$_2$—CH$_2$—. Polyethylene glycols can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400.

Polyethylene glycols can have a free hydroxyl group at each end of the polymer molecule, or can have one or more hydroxyl groups etherified with a lower alkyl, e.g., a methyl group. Also suitable are derivatives of polyethylene glycols having esterifiable carboxyl groups.

In some embodiments, the polyethylene glycol is functionalized with amine groups. Such amine groups can be used for conjugating the luminescent nanoparticle with a molecule, such as a nucleic acid or an adaptor molecule.

Suitable polyethylene glycols include, but are not limited to the CARBOWAX™ and CARBOWAX™ Sentry series (available from Dow), the LIPDXOL™ series (available from Brenntag), the LUTROL™ series (available from BASF), and the PLURIOL™ series (available from BASF).

Further, as used herein, the term "polyethylene glycol" is synonymous with the terms "polyethylene oxide" (PEO). These terms are used interchangeably, regardless of molecular weight, chain length, viscosity, branching structures if any, and the like. The terms "oligo ethylene glycol" and "oligo ethylene oxide" are also used for shorter versions of polyethylene glycol.

In some embodiments, the luminescent nanoparticle has a substantially neutral charge. The inventors have discovered that luminescent nanoparticles having a substantially neutral charge have reduced non-specific binding to a cell or tissue sample.

In some embodiments, the luminescent nanoparticle has a substantially non-fouling surface. The inventors have discovered that luminescent nanoparticles having a substantially non-fouling surface have reduced non-specific binding to a sample. As used herein, the term "non-fouling surface" is defined as a surface that does not substantially adsorb to or attract sample or substrate molecules non-specifically under the conditions for a given assay. Generally, a non-fouling surface will attract or absorb non-specifically less than 5% as much as a corresponding surface not treated to be non-fouling, e.g., less than 4%, less than 3%, less than 2%, less than 1% or even less relative to a non-treated corresponding surface. Non-fouling properties can be achieved, for example, by shielding the surface with a layer of non-fouling polymer (such as polyethylene glycol) or by utilizing zwitterionic surface coatings (i.e. coatings with alternating positive and negative charges, which yield highly hydrated, but neutrally charged surfaces).

In some embodiments, the luminescent nanoparticle is a colloidal water-soluble nanoparticle with a stable non-fouling coating such that non-specific binding of the luminescent nanoparticle to a sample (e.g., cell or tissue sample) is reduced or eliminated) relative to a nanoparticle lacking such coating. A nanoparticle lacking a stable-non-fouling coating usually has a highly charged surface, a surface with exposed hydrophobic areas, and/or a poorly stable coating.

In some embodiments, the label moiety can be a magnetic nanoparticle, a plasmonic nanoparticle, or an upconverting nanoparticle. As used herein, the term "plasmonic nanoparticle" refers to a nanoparticle that has very strong absorption (and scattering) spectrum that is tunable by changing the shape, the composition or the medium around their surfaces. It will be appreciated that the term includes all plasmonic nanoparticles of various shapes and surface surrounding which gives them surface plasmon absorption and scattering spectrum in the visible-near infra-red region of the spectrum. As used herein, an "upconverting nanoparticle" means a nanoparticle which is a combination of an absorber which is excited by infrared (IR) light and an emitter ion in a crystal lattice, which converts IR light into visible radiation.

In some embodiments, the label moiety is a fluorophore or fluorescent molecule or dye. A wide variety of fluorescent molecules are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+ Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); DIDS; Dihydrorhodamine 123 (DHR); DiO (DiOC18(3)); DiR; DiR (DiIC18(7)); Dopamine; DsRed; DTAF; DY-630—NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP(S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin EBG; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent molecules are available and can be used.

In some embodiments, the label moiety is a nanoparticle comprising a fluorophore or fluorescent molecule.

Other exemplary label moieties include radiolabels (e.g., $^3$H, 125I, $^{35}$S, $^{14}$C, or $^{32}$P), enzymes (e.g., galactosidases, glucorimidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such label moieties include U.S. Pat. Nos. 3,817,837, 3,850,752, 3,939,350, 3,996,345, 4,277,437, 4,275,149, and 4,366,241, content of each of which is incorporated herein by reference in its entirety.

In some embodiments, the label moiety is not a gold nanoparticle.

Affinity Molecule

As used herein, the term "affinity molecule" refers to any molecule that is capable of specifically interacting or binding with another molecule, i.e. a target molecule. Generally, the nature of interaction or binding between the affinity molecule and the target molecule is non-covalent, such as one or more of hydrogen bonding, Van der Waals forces, electrostatic forces, hydrophobic forces, and the like. However, interaction or binding can also be covalent.

As used herein, the term "specifically binding" and "specific binding" means that an affinity molecule binds to the target molecule with greater affinity than it binds to other molecules under the same conditions. Specific binding is generally indicated by a dissociation constant of 1 μM or lower, e.g., 500 nM or lower, 400 nM or lower, 300 nM or lower, 250 nM or lower, 200 nM or lower, 150 nM or lower, 100 nM or lower, 50 nM or lower, 40 nM or lower, 30 nM or lower, 20 nM or lower, 10 nM or lower, or 1 nM or lower.

An affinity molecule can be a naturally-occurring, recombinant or synthetic molecule. However, an affinity molecule need not comprise an entire naturally occurring molecule but can consist of only a portion, fragment or subunit of a naturally or non-naturally occurring molecule. Exemplary affinity molecules include, but are not limited to, ligand receptors, ligands for a receptor, one member of a coupling pair, nucleic acids (e.g., aptamers), peptides, proteins, peptidomimetics, antibodies, portion of an antibody, antibody-like molecules, antigens, and the like.

In some embodiments, the affinity molecule is an antibody or a portion thereof. In some embodiments, the affinity molecule is an antigen binding fragment of an antibody. As used herein, the term "antibody" or "antibodies" refers to an intact immunoglobulin or to a monoclonal or polyclonal antigen-binding portion with the Fc (crystallizable fragment) region or FcRn binding fragment of the Fc region. The term "antibodies" also includes "antibody-like molecules", such as portions of the antibodies, e.g., antigen-binding portions. Antigen-binding poritons can be produced by recombinant DNA techniques or by enzymatic or chemical cleavage of intact antibodies. "Antigen-binding portions" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding portions specific for various antigens are available commercially from vendors such as R&D Systems, BD Biosciences, e-Biosciences and Miltenyi, or can be raised against these cell-surface markers by methods known to those skilled in the art.

In some embodiments, the affinity molecule is not protein A, streptavidin, avidin, or biotin.

An affinity molecule can be generated by any method known in the art. For example, antibodies can be found in an antiserum, prepared from a hybridoma tissue culture supernatant or ascites fluid, or can be derived from a recombinant expression system, as is well known in the art. Fragments, portions or subunits of e.g., an antibody, receptor or other species, can be generated by chemical, enzymatic or other means, yielding for example, well-known (e.g., Fab, Fab') or novel molecules. The present invention also contemplates that affinity molecules can include recombinant, chimeric and hybrid molecules, such as humanized and primatized antibodies, and other non-naturally occurring antibody forms. Those skilled in the art will recognize that the non-limiting examples given above describing various forms of antibodies can also be extended to other affinity molecules such that recombinant, chimeric, hybrid, truncated etc., forms of non-antibody molecules can be used in the compositions and methods of the present invention.

In some embodiments, the affinity molecule and the label moiety can be reversibly conjugated to each other by an at least partially double-stranded nucleic acid comprising a first strand and a second strand. The first and second strand of the nucleic acid can specifically hybridize to each other. Without limitations, the affinity molecule and/or the label moiety can be linked to the nucleic acids strands covalently or non-covalently.

In some embodiments, the affinity molecule can be covalently linked to a strand of the double-stranded nucleic acid via a linker. When the affinity molecule is covalently linked to the nucleic acid via a linker, the linker can be a bond or bifunctional molecule. In some embodiments, the affinity molecule is covalently linked to a strand of the double-stranded oligonucleotide via a linker selected from the group consisting of a bond, succinimidyl-4-(N-maleimidomethyl) cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB, also referred to as SFB herein) linker, and any combination thereof.

Methods of linking a nucleic acid covalently or non-covalently with another molecule are well known in the art and available to an ordinarily skilled artisan. For example, DNA conjugated antibodies prepared with a variety of covalent and non-covalent procedures have been described for bio-analytical methods (Bailey, R. C., et al., *DNA-encoded antibody libraries: a unified platform for multiplexed cell sorting and detection of genes and proteins*. Journal of the American Chemical Society, 2007. 129(7): p. 1959-67 and Lind, K. and M. Kubista, *Development and evaluation of three real-time immuno-PCR assemblages for quantification of PSA*. Journal of Immunological Methods, 2005. 304(1-2): p. 107-16).

Figure 2:
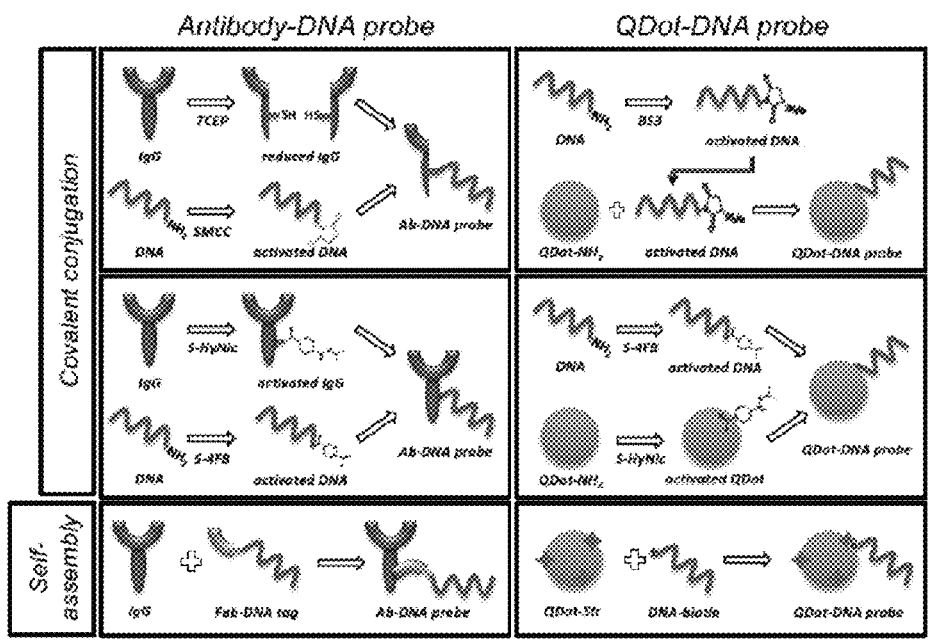
FIG. 2 shows exemplary strategies for conjugation of Ab with quantum dots via DNA mediated linkage including covalent conjugation with reduced IgG, amine cross-linking using whole antibodies, and non-covalent self-assembly with protein A (SpA). Each of these approaches can be used to conjugate nucleic acid, e.g., DNA oligonucleotides to antibody. It is important to recognize the limitations inherent in each approach. For example, covalent conjugation with reduced IgG can be used, but might lead to loss of Ab affinity. Amine cross-linking can be used using whole antibodies, but there may be little control over the final bioconjugate structure. Non-covalent self-assembly with SpA-DNA can provide a route for labeling of intact antibodies, but the bioconjugate may possess only short-term stability.

In a non-limiting example, an amine-functionalized nucleic acid can be covalently linked to an affinity molecule comprising a free sulfhydryl group. As shown in FIG. 2A, one such covalent conjugation approach involves reduction of IgG followed by maleimide mediated reaction between pre-activated oligonucleotide and a sulfhydryl group in the Fc region of an antibody. One benefit of this approach is the controlled stoichiometry and structure of antibody-nucleic acid bioconjugate. As reaction is limited to 1-2 sites on the Fc region, the preparation of antibodies with intact Fab antigen recognition region and a single nucleic acid is readily achievable. This can be important for minimizing potential off-target binding of antibody-nucleic acid bioconjugates.

Alternatively, amine cross-linking can be used for covalently linking a nucleic acid to an affinity molecule comprising an amine group. FIG. 2B illustrate covalent linking of a nucleic acid with an antibody using amine cross-linking.

While, covalent linking can produce stable and functional affinity molecule-nucleic acid conjugates, complexity, high cost, and low yield can hamper preparation of different affinity molecule-nucleic acid conjugates. Accordingly, in some embodiments, the affinity molecule can be non-covalently linked to the nucleic acid via an adaptor molecule to which the nucleic acid is linked, covalently or non-covalently. An adaptor molecule can be covalently linked to the nucleic acid using a linker.

Adaptor Molecule

As used herein, the term "adaptor molecule" means any molecule that is capable of specifically binding with an affinity molecule. Generally, an appropriate adaptor molecule does not inhibit or reduce binding of the affinity molecule to its target, i.e., binding of the affinity molecule to its target is reduced very little, if at all, when said affinity molecule is bound by an adaptor molecule. In one sense, an adaptor molecule can be an affinity molecule as that term is used herein. Exemplary adaptor molecules include, but are not limited to protein A, protein G, antibody, portion of an antibody, antigen, receptor ligand, receptor, ligand binding fragment of a receptor, one member of a coupling pair, an aptamer, and the like. In some embodiments, when the affinity molecule is an antibody or antibody derivative, the adaptor molecule is protein A, streptavidin, avidin, biotin, an antibody, or a portion of an antibody.

In some embodiments, the adaptor molecule is not protein A, streptavidin, avidin, biotin, an antibody, or a portion of an antibody.

Compositions Comprising a Plurality of Labeled Molecules

Provided herein is also a composition comprising an affinity molecule covalently conjugated with a single-stranded nucleic acid. Further, a composition comprising a plurality of different such affinity molecules is also provided herein. Each member of the plurality is conjugated with a single-stranded nucleic acid which is different for each member of the plurality.

Further provided herein is a composition comprising an affinity molecule non-covalently conjugated with an adaptor molecule, wherein the adaptor molecule is conjugated (covalently or non-covalently) with a single-stranded nucleic acid. A composition comprising a plurality of different such affinity molecules is also provided herein. Each member of the plurality is conjugated with a single-stranded nucleic acid which is different for each member of the plurality.

A composition comprising a label moiety covalently conjugated with a single-stranded nucleic acid is also provided herein. Further, a composition comprising a plurality of different such label moieties is also provided herein. Each member of the plurality is conjugated with a single-stranded nucleic acid which is different for each member of the plurality. In some embodiments, the composition comprising plurality of nucleic acid conjugated affinity molecules is a dried composition. Further, at least one detectable property of the label moiety on each member of the plurality is different or distinguishable from at least one detectable property of a label moiety on the other members of the plurality. For example, the label moiety on one member can have a peak emission wavelength that differs by least 5 nm, at least 10 nm, at least 15 nm, at least 20 nm, at least 25 nm, at least 30 nm, at least 35 nm, at least 40 nm, at least 45 nm, or at least 50 nm from the peak emission wavelength of the label moiety on another member.

Also provided herein is composition comprising a label moiety non-covalently conjugated with an adaptor molecule via a double-stranded nucleic acid. A composition comprising a plurality of different such label moieties is also provided. Each member of the plurality is conjugated with an adaptor molecule via a double-stranded nucleic acid that is different for each member of the plurality such that a nucleic acid strand of the double-stranded nucleic acid of a first member of the plurality does not specifically bind or hybridize with either nucleic strand of a second member of the plurality.

Further provided herein is composition comprising an adaptor molecule conjugated with a single-stranded nucleic acid. A composition comprising a plurality of different such adaptor molecules is also provided herein. Each member of the plurality is conjugated with a single-stranded nucleic acid which is different for each member of the plurality Provided herein is also a composition comprising a plurality of different affinity molecules, wherein each member of the plurality is capable of binding a different target. Each member of the plurality comprising an affinity molecule reversibly conjugated to a label moiety. At least one detectable property of the label moiety on each member is different or distinguishable from at least one detectable property of a label moiety on the other members. For example, the label moiety on one member can have a peak emission wavelength that differs by least 5 nm, at least 10 nm, at least 15 nm, at least 20 nm, at least 25 nm, at least 30 nm, at least 35 nm, at least 40 nm, at least 45 nm, or at least 50 nm from the peak emission wavelength of the label moiety on another member. Further, the inventors have discovered that no detectable re-arrangement takes place between different members of the composition. In other words, there is no detectable re-arrangement of a label moiety from one affinity molecule to a different affinity molecule in the composition.

In some embodiments, the affinity molecule on a member of the plurality is conjugated to the label moiety via hybridized first and second nucleic acid strands. The first and second nucleic acid strands of each member specifically hybridize with each other, i.e., the first and second strands of one member do not specifically hybridize with a first or a second strand of a different member under moderately or highly stringent conditions. The affinity molecule is conjugated, covalently or non-covalently, with the first nucleic acid strand and the label moiety is conjugated, covalently or non-covalently, with the second nucleic acid stand.

In some embodiments, the affinity molecule in a composition comprising a plurality of affinity molecules can be conjugated via an adaptor molecule to the label molecule, wherein the label molecule is conjugated (covalently or non-covalently) with the adaptor molecule and the adaptor molecule is non-covalently bound with the affinity molecule.

As used herein, the term "plurality" means "two or more", unless expressly specified otherwise. For example, a plurality can comprise 2, 3, 4, 5, 6, 7, 8, 9, 10, 11, 12, 13, 14, 15, 16, 17, 18, 19, 20, 21, 22, 23, 24, 25 or more different members.

Further, a composition comprising a plurality of different molecules can be in any form, e.g., liquid or solid. Accordingly, in some embodiments, the composition comprising a plurality of different molecules is a dried composition, e.g., a powder.

Labeled Cell or Tissue Sample

Provided herein is also a composition comprising a cell or a tissue sample and a plurality of different affinity molecules, each member of the plurality comprising an affinity molecule conjugated to a first single-strand nucleic acid and wherein each member of the plurality is bound to a different analyte or biomarker in the cell or tissue sample. The first single-strand nucleic acid is different from the first single-strand nucleic acid conjugated to each other member of the plurality. As used herein, the term "different nucleic acid strand" means that the nucleotide sequence of one strand is different from another strand, i.e., two different strands have less than 80% (e.g., less than 70%, less than 60%, less than 50%, less than 40%, less than 30%, less than 20%, or less than 10%) sequence homology or complementarity. Further, the first nucleic acid strands from different members of the plurality can be of different lengths. Moreover, different first nucleic acid strands will specifically hybridize to different second strands.

In some embodiments, the composition further comprises a plurality of second single strand nucleic acid molecules, wherein each member of the plurality of second single-strand nucleic acids is conjugated to a different label moiety, and wherein each different second single strand nucleic acid molecule specifically hybridizes to a different first single strand nucleic acid molecule conjugated to a member of the plurality of different affinity molecules. In this composition, at least a subset of the plurality of different affinity molecules bound to the analytes in the cell or tissue sample is specifically associated with a plurality of different label moieties, wherein detectable properties of the different label moieties are distinguishable. In this manner, each different biomarker recognized by a different affinity molecule can be specifically and reversibly conjugated to a distinguishable label moiety.

Method

The compositions described herein can be used in biological assays for detection, identification and/or quantification of target molecules or analytes, including multiplex staining for molecular profiling of individual cells or cellular populations. For example, the compositions can be adapted for use in immunofluorescence, immunohistochemistry, western blot, and the like. Accordingly, disclosed herein is also a method for staining one or more analytes in a sample for identification or quantitation.

Generally, the methods comprise contacting a plurality of analytes in a sample with a first plurality of affinity molecules, wherein each affinity molecule of the plurality binds to a different analyte if present. The affinity molecules can be pre-conjugated with label moieties before contacting or binding to the analytes or the affinity molecules can be conjugated to label moieties after affinity molecules are bound with the analytes. Conjugated label moieties provide detectable signal for identification or quantitation of bound analyte. At least one detectable signal from each label moiety is different from at least one detectable signal of other label moieties. In other words, in the subject method of this embodiment, each different analyte is bound to a different label moiety such that each different analyte has detectable signal that is different from at least one detectable signal associated with other analytes.

Signal from the conjugated label moieties can be detected using any method known in the art for detecting the particular label moiety to provide identification or quantitation of at least a subset of the plurality of analytes in the sample. The number of analytes identified or quantitated can range from 1 to 100's. For example, 1, 2, 3, 4, 5, 6, 7, 8, 9, 10, 11, 12, 13, 14, 15, 16, 17, 18, 19, 20, 21, 22, 23, 24, 25 or more different analytes can be identified or quantitated at the same time.

After detecting the signal from the conjugated label moieties, the signal can be erased and a different plurality of analytes can be detected using a second plurality of affinity molecules, wherein each affinity molecule of the plurality binds to a different analyte. Again an affinity molecule in the second plurality can be pre-conjugated with a label moiety before binding to the analyte or the affinity molecule can be conjugated to a label molecule after binding of the analyte. Signal from the second set of conjugated label moieties can be detected to provide identification or quantitation of a second plurality of analytes in the sample.

The erasing and relabeling steps can be cycled or repeated as many times as needed to detect the desired number of different analytes in the sample. For example, erasing and relabeling steps can repeated 1, 2, 3, 4, 5, 6, 7, 8, 9, 10, 11, 12, 13, 14, 15, 16, 17, 18, 19, 20, 21, 22, 23, 24, 25 or more times. Additionally, number of analytes identified or quantitated in each cycle can range from 1 to 100's. For example, 1, 2, 3, 4, 5, 6, 7, 8, 9, 10, 11, 12, 13, 14, 15, 16, 17, 18, 19, 20, 21, 22, 23, 24, 25 or more different analytes can be identified or quantitated in each cycle. Thus, the method provides multiplexing capabilities to identified or quantitate from 1 to 100's of analytes in a sample.

If the affinity molecule is not pre-conjugated with the label moiety, nucleic acid conjugated affinity molecules for binding all the different desired analytes can be added to the sample in one contacting step. Then, for detection, a subset of the analyte-bound affinity molecules can be specifically conjugated with different label moieties via complementary nucleic acid conjugated label moieties, and signal from the conjugated label moieties can be detected to provide identification or quantitation of a subset of the analytes. The signal can be quenched or erased and a different subset of the bound affinity molecules detected by specific binding of a new set of distinguishable label moieties bearing different nucleic acid strands that hybridize to nucleic acids on a different subset of affinity molecule bound to the sample, to identify or quantitate a different subset of analytes. This process can be repeated as many times as needed.

In some embodiments, when the affinity molecule is not pre-conjugated to the label moiety before contacting with the analyte, the method comprises, in order:

(a) contacting the sample with a plurality of different affinity molecules under conditions that permit specific analyte binding by the different affinity molecules, wherein each different affinity molecule specifically binds a different member of the plurality of analytes, and wherein each different affinity molecule is conjugated to a different first single strand nucleic acid, such that members of the plurality of different affinity molecules become bound to members of the plurality of analytes present in the sample;

(b) contacting the sample, under conditions that permit specific nucleic acid hybridization, with a first set of different second single strand nucleic acid molecules, each conjugated to a different label moiety, wherein each different second single strand nucleic acid molecule specifically hybridizes to a different first single strand nucleic acid molecule conjugated to a member of the plurality of different affinity molecules, such that at least a subset of the plurality of different affinity molecules bound to members of the plurality of analytes in the sample becomes specifically associated with a plurality of different label moieties, wherein detectable properties of the different label moieties are distinguishable; and (c) detecting signal from label moieties associated with affinity molecules bound to the sample, thereby detecting the presence or amount of at least a subset of the plurality of analytes.

In some embodiments, the method further comprises the steps of:

(d) erasing the signal from the label moieties conjugated to the first set of second single strand nucleic acid molecules;

(e) contacting the sample, under conditions that permit specific nucleic acid hybridization, with a second set of different second single strand nucleic acid molecules, each conjugated to a different label, wherein each different second single strand nucleic acid molecule specifically hybridizes to a different first single strand nucleic acid molecule conjugated to a member of the plurality of different affinity molecules, such that a different subset of the plurality of different affinity molecules bound to members of the plurality of analytes in the sample becomes specifically associated with a different plurality of different label moieties relative to those detected in step (c);

(f) detecting signal from label moieties associated with affinity molecules bound to the sample, thereby detecting the presence or amount of the different subset of the plurality of analytes; and (g) optionally repeating steps (d)-(f) with a further set of second single strand nucleic acid molecules.

In some embodiments, when the affinity molecule is reversibly conjugated with the label moiety before contacting the sample, the method comprises, in order:

(a) contacting the sample with a first plurality of different affinity molecules under conditions that permit specific analyte binding by the different affinity molecules, wherein each different affinity molecule specifically binds a different member of the plurality of analytes, wherein each different affinity molecule is conjugated to a different first single strand nucleic acid molecule that is specifically hybridized to a second single strand nucleic acid molecule, wherein the second single strand nucleic acid molecule is conjugated to a label moiety, such that each different affinity molecule is conjugated via different hybridized first and second nucleic acid strands to a different label moiety and members of the plurality of different affinity molecules become bound to members of the plurality of analytes present in the sample, wherein detectable properties of the label moieties are distinguishable; and (b) detecting signal from label moieties associated with the first plurality of affinity molecules bound to the sample, thereby detecting the presence or amount of the plurality of analytes.

In some embodiments, the method further comprises the steps of:

(c) erasing the signal from the label molecules conjugated to the first set of second single strand nucleic acid molecules;

(d) contacting the sample with a second plurality of different affinity molecules under conditions that permit specific analyte binding by the different affinity molecules;

(e) detecting signal from label moieties associated with a second plurality of affinity molecules bound to the sample, thereby detecting the presence or amount of at least a subset of the plurality of analytes; and (f) optionally repeating steps (c)-(e) with a further second set of the affinity molecules.

Conditions that permit specific analyte binding by affinity molecules are well known in the art. A, but one example, conditions that permit specific antibody binding are well known in the art. Exemplary conditions are also described in the examples provided herein below.

Similarly, conditions that permit specific nucleic acid hybridization are also well known in the art. Exemplary conditions are also described in the examples provided herein below.

As used herein, the term "analyte" refers to a molecule, substance or chemical constituent of interest in a sample or a biological cell. Thus, the term "analyte" includes any substance which is desired to be detected in a given sample. The analyte can be attached to or present on a solid support surface. For example, an analyte can be attached to or present on surface of a plate, dish, well, membrane, grating, bead or particle (including, but not limited to an agarose or latex bead or particle, a magnetic particle, etc.). In some embodiments, the solid support can be an ELISA plate or a western blot membrane. In some embodiments, an analyte can be present on surface of a cell or a biological sample. The cell or biological sample can be unfixed or fixed.

In some embodiments, the analyte is biomarker. As used herein, the term "biomarker" refers to any biological feature from tissue sample or a cell to be identified or quantitated. A biomarker can be useful or potentially useful for measuring the initiation, progression, severity, pathology, aggressiveness, grade, activity, disability, mortality, morbidity, disease sub-classification or other underlying feature of one or more biological processes, pathogenic processes, diseases, or responses to a therapeutic intervention. A biomarker is virtually any biological compound, such as a protein and a fragment thereof, a peptide, a polypeptide, a proteoglycan, a glycoprotein, a lipoprotein, a carbohydrate, a lipid, a nucleic acid, an organic on inorganic chemical, a natural polymer, and a small molecule, that is present in the sample to be analyzed and that can be isolated from, or measured in, the sample.

As used therein, the term "contacting" refers to any suitable means for delivering, or exposing, to a sample, the specified composition or molecule. In some embodiments, the term "contacting" refers to adding specific composition or molecules (e.g., suspended in a solution) directly to the sample. In some embodiments, the term "contacting" can further comprise mixing the sample with the specific composition or molecules by any means known in the art (e.g., vortexing, pipetting, and/or agitating). In some embodiments, the term "contacting" can further comprise incubating the sample together with the specific composition or molecules for a sufficient amount of time, e.g., to allow binding of the affinity molecules to the target analytes. The contact time can be of any suitable length, depending on the binding affinities and/or concentrations of the affinity molecules or the analytes, concentrations of the affinity molecules, or incubation condition (e.g., temperature).

In some embodiments, the contact time between the sample and the affinity molecules can be at least about 30 seconds, at least about 1 minute, at least about 5 minutes, at least about 10 minutes, at least about 15 minutes, at least about 30 minutes, at least about 1 hour, at least about 2 hours, at least about 3 hours, at least about 4 hours, at least about 6 hours, at least about 8 hours, at least about 10 hours, at least about 12 hours, at least about 24 hours, at least about 48 hours or longer. One of skill in the art can adjust the contact time and conditions accordingly.

Similarly, contact time between the sample and the second single-strand nucleic acid can be at least can be at least about 30 seconds, at least about 1 minute, at least about 5 minutes, at least about 10 minutes, at least about 15 minutes, at least about 30 minutes, at least about 1 hour, at least about 2 hours, at least about 3 hours, at least about 4 hours, at least about 6 hours, at least about 8 hours, at least about 10 hours, at least about 12 hours, at least about 24 hours, at least about 48 hours or longer. Again, one of skill in the art can adjust the contact time and conditions accordingly.

As used herein, the term "detecting" refers to observing a signal from a label moiety to indicate the presence of an analyte in the sample. Any method known in the art for detecting a particular label moiety can be used for detection. Exemplary detection methods include, but are not limited to, spectroscopic, photochemical, biochemical, immunochemical, electrical, optical or chemical methods.

In some embodiments, detecting the signal comprises imaging spectral emission from the label moiety. Systems and methods for imaging spectral emission from a label moiety are well known in the art and available to an ordinarily skilled artisan.

Systems and methods for multispectral imaging are described, for example, in U.S. application Ser. No. 10/965, 209; Ser. No. 12/092,670; Ser. No. 12/456,022; Ser. No. 12/525,059; and Ser. No. 12/985,161, and U.S. Pat. No. 6,208,749; U.S. Pat. No. 6,480,273; U.S. Pat. No. 6,639,665; U.S. Pat. No. 6,825,930; U.S. Pat. No. 7,019,777; U.S. Pat. No. 7,145,124; U.S. Pat. No. 7,473,334; U.S. Pat. No. 7,786, 440; U.S. Pat. No. 7,589,772; and U.S. Pat. No. 8,027,041, content of all of which is incorporated herein by reference.

Figure 27:
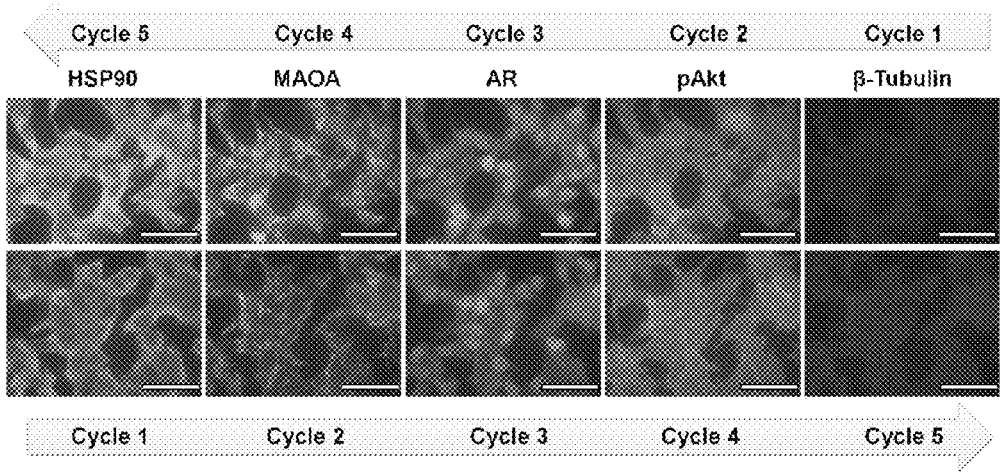
FIG. 27 shows sequential staining of 5 biomarkers performed in different order. To evaluate dependence of sequential staining performance on the order of biomarkers stained, procedure was performed in the order from low-abundance to high-abundance biomarker (top row) and from high-abundance to low-abundance biomarker (bottom row). Independent of order, all biomarkers were reliably stained showing correct staining pattern and relative staining intensity. Also, no carry-over fluorescence, build-up of background fluorescence, or cross-talk between cycles was observed. Scale bar, 50 µm.
Figure 28A:
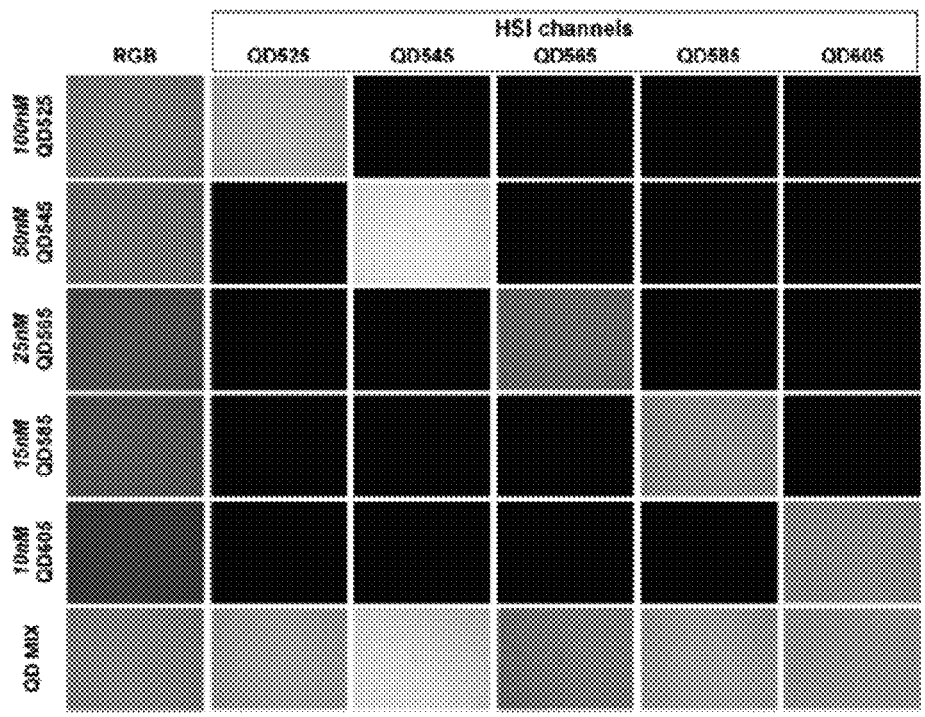
FIG. 28A shows hyperspectral imaging (HSI) can be used to accurately identify a composition comprising a mix of QDs.
Figure 28B:
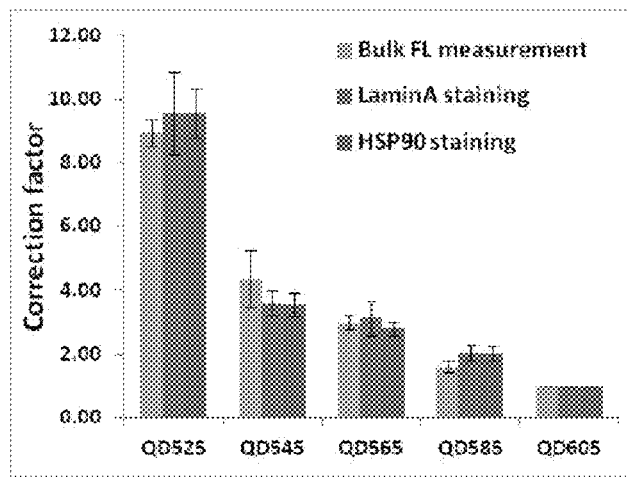
FIG. 28B shows quantitative analysis of biomarker expression (LaminA and HSP90) with QD probes is consistent with differential QD brightness (measured by HSI from bulk QD solution).

In some embodiments, imaging spectral emission comprises hyperspectral imaging. Hyperspectral imaging is an extension of multispectral imaging and is also referred to as imaging spectrometry. Whereas multispectral imaging consists of measurements from two to about ten discrete wavelengths for a given image, hyperspectral imaging measures more than 10 contiguous wavelengths, often many more Like multispectral imaging, hyperspectral imaging is an imaging technique that combines aspects of conventional imaging with spectrometry and radiometry. The result is a technique that is capable of providing an absolute radiometric measurement over a contiguous spectral range for each and every pixel of an image. Thus, data from a hyperspectral image contains two-dimensional spatial information plus spectral information over the spectral image. These data can be considered as a three dimensional hypercube which can provide physical and geometric observations of size dimension, orientation, shape, color, and texture, as well as chemical/molecular information. As shown in FIG. 27, hyperspectral imaging can accurately identify different components of a composition comprising a mix of QDs. Systems and methods for hyperspectral imaging are described, for example, in U.S. application Ser. No. 11/774,704; Ser. No. 11/912,361; Ser. No. 11/933,253; Ser. No. 11/987,574; Ser. No. 12/162,486; Ser. No. 12/284,462; and Ser. No. 12/370,557, and U.S. Pat. No. 6,008,492; U.S. Pat. No. 6,552,788; U.S. Pat. No. 6,831, 688; U.S. Pat. No. 6,998,614; U.S. Pat. No. 7,013,172; U.S. Pat. No. 7,149,366; U.S. Pat. No. 7,420,679; and U.S. Pat. No. 7,835,002, content of all of which is incorporated herein by reference.

In some embodiments, the detecting can further comprise spectral unmixing. Spectral unmixing corresponds to a linear decomposition of an image or other data set into a series of contributions from different spectral contributors. For example, image of a sample can include multiple different contributions from label moieties conjugated with affinity molecules which are bound with the analytes in the sample. Each of these contributions can be unmixed or decomposed into a separate spectral channel, forming an image of the sample that corresponds almost entirely to signal contributions from single spectral sources. When the contributions are unmixed into separate channels or images, signal strengths can be accurately quantified and analyzed. Methods and apparatus for spectral unmixing are known in the art. See for example, U.S. patent application Ser. No. 11/844,920; Ser. No. 12/757,831; Ser. No. 11/649,292; Ser. No. 12/564,857; and Ser. No. 11/999,914, and U.S. Pat. No. 6,665,438; U.S. Pat. No. 6,930,773; U.S. Pat. No. 7,072,770; U.S. Pat. No. 7,471,386; and U.S. Pat. No. 7,555,155, content of all of which is incorporated herein by reference.

As used herein, the term "erasing" a signal means removing the signal or reducing strength of the signal so as not to interfere with signal from another label moiety. A signal can be erased by quenching the signal. Alternatively, or in addition, the signal can be erased by removing the label moiety generating the signal or the affinity molecule conjugated with the label moiety generating the signal from the sample. A signal can be erased by any method known to the artisan including, but not limited to, chemical, physical, or enzymatic means. For example, a signal can be erased by elution, denaturation, washing, displacement, cleavage, photo-bleaching, heating, quenching with a fluorophore acceptor, or a combination thereof. Generally, a suitable method employed for erasing the signal does not affect the sample or its biomarkers.

In some embodiments, the label moiety or the affinity molecule conjugated with the label moiety can be physically removed from the sample. This can be accomplished by inhibiting or reducing or overcoming the binding between the affinity molecule and the analyte or between the affinity molecule and the label moiety. Methods of unbinding an affinity molecule from its target are well known in the art. For example, washing with a low pH buffer can reduce the binding between an affinity molecule and its target. In other examples, changing the salt concentrations can reduce the binding strength between an affinity molecule and its target. Heating can also dissociate an affinity molecule from its target.

In some of the compositions described herein, the affinity molecule is conjugated with the label moiety via a nucleic acid linker, wherein the nucleic acid comprises first and second strands of nucleic acid which are specifically hybridized to each other. When such compositions are used, the signal can be erased by denaturing the double-stranded nucleic acid linker to release or unconjugate the label moiety from the affinity molecule.

As an ordinarily skilled artisan is well aware, a double-stranded nucleic acid can be denatured into single strands by heating. Accordingly, in some embodiments, erasing is by heating the sample to "melt" the double-stranded nucleic acid linker. Thus, unconjugating or removing the label moiety from the affinity molecule which can still be bound to the analyte in the sample. As an example, washing or rinsing with a suitable wash buffer at a temperature greater than the melting temperature of the hybridized nucleic acid strands can permit label removal.

In some embodiments, strand displacement can be used for dissociating the two strands of the nucleic acid linker. As used herein, the term "strand displacement" refers to replacing one of the nucleic acid strands in a double-stranded nucleic acid by third strand. For example, if strands A and B are in the original double-stranded nucleic acid, then strand displacement comprises replacing either strand A or B in the duplex with strand C to obtain either a A:C or B:C duplex.

Accordingly, in some embodiments, erasing the signal comprises adding a nucleic acid to the sample, e.g., a single-stranded nucleic acid. The nucleic acid to be added ("displacement nucleic acid") has a nucleotide sequence which is substantially complementary to one of the strands of the nucleic acid linker. Further, the displacement strand can specifically hybridize with the one of the strands of the nucleic acid linker more strongly relative to the hybridization of the two strands of the linker to each other.

Generally, strand displacement works best when the displacing strand is complementary to a longer stretch of one of the nucleic acid strands than the strand being displaced. Thus, the most readily displaced strand is that which generates a partially double-stranded configuration between the first and second nucleic acid strands linking affinity molecule and label moiety. This can be accomplished by having the nucleic acid linker comprise a single-strand overhang on one of the stands and displacing strand being complementary to said strand over a length that is longer than the other strand of the linker.

In addition, or alternatively, the displacing stand can comprise on or more modifications that promote duplex stability. Exemplary such modifications include, but are not limited to, 2-amino-A; 2-thio U; 5-Me-thio-U; G-clamp (an analog of C having 4 hydrogen bonds); psuedo uridine; 2' modifications, e.g., 2'F; "locked" nucleic acids (LNA) in which the oxygen at the 2' position is connected by $(CH_2)_n$, wherein n=1-4, to the 4' carbon of the same ribose sugar, preferably n is 1 (LNA) or 2 (ENA); inter-sugar modifications, such as phosphorothioates.

After addition of the displacing strand, the sample can be incubated for a sufficient period of time to allow the displacing strand to hybridize with its complementary strand of the nucleic acid linker. For example, the incubation time can be at least about 30 seconds, at least about 1 minute, at least about 5 minutes, at least about 10 minutes, at least about 15 minutes, at least about 30 minutes, at least about 1 hour, at least about 2 hours, at least about 3 hours, at least about 4 hours, at least about 6 hours, at least about 8 hours, at least about 10 hours, at least about 12 hours, at least about 24 hours, at least about 48 hours or longer. One of skill in the art can adjust the contact time accordingly.

In other embodiments, label removal or signal erasure can include treatment with a molecule that cleaves nucleic acids. For example, label removal can include treatment with a nuclease that cleaves double-stranded sequences. Such nucleases can recognize a specific sequence, e.g., as effected by a restriction endonuclease, or, alternatively, can recognize double-stranded sequences in sequence independent manner, e.g., as effected by RNaseH.

When the nucleic acid linker comprises a single-stranded region in the duplex region, a single-stranded nuclease can be used to cleave the single-stranded region. Cleavage at an internal position of one strand can reduce the binding affinity of the two strands of the linker for each other thus "melting" the linker and the affinity molecule and the label molecules can dissociate from each other.

As is well known in the art, methods for staining of biomarkers or analytes in sample can comprise one or more washing or blocking steps. For example, a sample can be subjected to one or more blocking steps before contacting the sample with the affinity molecule to reduce or inhibit non-specific binding of the affinity molecule to the sample. One or more blocking steps can also be used before contacting the sample with the DNA-conjugated label moiety to reduce or inhibit non-specific binding of the label moiety to undesired affinity molecule or the sample. One or more washing steps can be performed after a contacting step to wash away any leftover reagents from the contacting step.

Embodiments of the aspects disclosed herein can be also be described by any of the following numbered paragraphs:

1. A composition comprising an affinity molecule reversibly conjugated to a label moiety, in which the affinity molecule is linked to the label moiety via a linker comprising first and second strands of nucleic acid that specifically hybridize to each other, wherein the first nucleic acid strand is linked to the affinity molecule and the second nucleic acid strand is linked to the nanoparticle, such that the affinity molecule is conjugated to the label moiety under conditions that permit hybridization between the first and second nucleic acid strands, but is not conjugated to the nanoparticle under conditions that do not permit such hybridization.

2. The composition of paragraph 1, wherein the first and second nucleic acid strands hybridize to form a double-stranded region of about 6 base-pairs to about 30 base-pairs.
3. The composition of paragraph 2, wherein the first and second nucleic acid strands hybridize to form a double-stranded region of about 12 to about 16 base-pairs.
4. The composition of any of paragraphs 1-3, wherein the first and second nucleic acid strands hybridize to form a double-stranded region having a melting temperature about 40° C. or above.
5. The composition of any of paragraphs 1-4, wherein the first and second nucleic acid strands hybridize to form a double-stranded region having a 3' or 5' single-stranded overhang of about 6 to about 20 nucleotides.
6. The composition of any of paragraphs 1-5, wherein the affinity molecule and the label moiety are in a 1:1 (affinity molecule: label moiety) ratio.
7. The composition of any of paragraphs 1-6, wherein
   (i) the affinity molecule is conjugated to 3' terminus of the first nucleic acid strand and the label moiety is conjugated to 3' terminus of the second nucleic acid strand; or
   (ii) the affinity molecule is conjugated to 5' terminus of the first nucleic acid strand and the label moiety is conjugated to 5' terminus of the second nucleic acid strand.
8. The composition of any of paragraphs 1-7, wherein at least one of the first or the second strands of nucleic acid comprises a modification selected from the group consisting of nucleobase modifications, sugar modifications, inter-sugar linkage modifications, backbone modifications, and any combinations thereof.
9. The composition of any of paragraphs 1-8, wherein the affinity molecule is an antibody or antigen-binding portion thereof.
10. The composition of any of paragraphs 1-9, wherein the affinity molecule is covalently linked to the first nucleic acid strand through a linker or the affinity molecule is non-covalently linked to the first nucleic acid strand through an adaptor molecule.
11. The composition of paragraph 10, wherein the linker is a bond, succinimidyl-4-(N-maleimidomethyl)cyclohexane-1-carboxylate (SMCC) linker, sulfo-SMCC linker, succin-imidyl-6-hydrazino-nicotinamide (S-HyNic) linker, N-succinimidyl-4-formylbenzamide (S-4FB) linker, bis-aryl hydrazone bond, an amide bond, tow amide bonds on a spacer for cross-linking two —NH2 groups, triazole bond (from "click" reaction), a phosphodiester linkage, a phso-phothioate linkage, or any combination thereof.
12. The composition of paragraph 10, wherein the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.
13. The composition of any of paragraphs 1-12, wherein the label moiety is covalently linked to the second nucleic acid strand through a linker or the label moiety is non-co-valently linked to the second nucleic acid via a coupling pair.
14. The composition of any of paragraphs 1-13, wherein the label moiety is selected from the group consisting of a luminescent nanoparticle, fluorescent molecule, chemilu-miniscent moiety, bioluminescent moiety, luminescent molecule, radioisotope, chromophore, magnetic nanoparticles, plasmonic nanoparticles, upconverting nanopar-ticles, nanoparticles comprising fluorescent molecules, nanoparticles comprising fluorophores, and any combination thereof.
15. The composition paragraph 14, wherein the luminescent nanoparticle is an inorganic semiconductor nanoparticle chosen from group consisting of a Group II, Group III, Group IV, Group V, and Group VI semiconductor nanoparticles.
16. The composition of paragraph 14 or 15, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.
17. The composition of any of paragraphs 14-16, wherein the luminescent nanoparticle is core type or core-shell type.
18. The composition any of paragraphs 14-17, wherein the luminescent nanoparticle comprises a core and a shell forms a colloidal particle.
19. The composition any of paragraphs 14-17, wherein the luminescent nanoparticle core comprises CdSe and the shell comprises ZnS.
20. The composition any of paragraphs 14-19, wherein the luminescent nanoparticle is about 1 nm to about 100 nm in size.
21. The composition any of paragraphs 14-21, wherein the luminescent nanoparticle comprises a polymer coating layer.
22. The composition of paragraph 21, wherein the polymer is polyethylene glycol.
23. The composition any of paragraphs 14-22, wherein the luminescent nanoparticle is a colloidal water-soluble nano-particle comprising a stable non-fouling coating such that non-specific binding of the nanoparticle to a cell or a tissue sample is reduced relative to a nanoparticle lacking a non-fouling coating.
24. A composition comprising an affinity molecule reversibly conjugated to a luminescent nanoparticle, in which the nanoparticle is covalently linked to an adaptor molecule and the adaptor molecule is non-covalently linked to the affinity molecule, wherein the affinity molecule and the adaptor molecule are present in a 1:1 ratio, and wherein the luminescent nanoparticle is a colloidal water-soluble nano-particle comprising a stable non-fouling coating such that non-specific binding of the nanoparticle to a cell or a tissue sample is reduced relative to a nanoparticle lacking a non-fouling coating.
25. The composition of paragraph 24, wherein the affinity molecule is an antibody or antigen-binding portion thereof.
26. The composition any of paragraphs 24-25, wherein the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.
27. The composition any of paragraphs 24-26, wherein the luminescent nanoparticle is an inorganic semiconductor nanoparticle chosen from group consisting of a Group II, Group III, Group IV, Group V, and Group VI semiconductor nanoparticles.
28. The composition any of paragraphs 24-27, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.

29. The composition any of paragraphs 24-28, wherein the luminescent nanoparticle is core type or core-shell type.

30. The composition any of paragraphs 24-29, wherein the luminescent nanoparticle comprises a core and a shell forms a colloidal particle.

31. The composition any of paragraphs 24-30, wherein the luminescent nanoparticle core comprises CdSe and the shell comprises ZnS.

32. The composition any of paragraphs 24-31, wherein the luminescent nanoparticle is about 1 nm to about 100 nm in size.

33. The composition any of paragraphs 24-33, wherein the luminescent nanoparticle comprises a polymer coating layer.

34. The composition any of paragraphs 24-33, wherein the polymer is polyethylene glycol.

35. A composition comprising a plurality of different affinity molecules, wherein:
    (i) each member of the plurality binds a different target, wherein each different affinity molecule is conjugated via different hybridized first and second nucleic acid strands to a different label moiety, wherein detectable properties of the different label moieties are distinguishable; or
    (ii) each member of the plurality binding a different target, wherein each different affinity molecule is conjugated to a different first single strand nucleic acid molecule that is specifically hybridized to a second single strand nucleic acid molecule, wherein the second single strand nucleic acid molecule is conjugated to a label moiety, such that each different affinity molecule is conjugated via different hybridized first and second nucleic acid strands to a different label moiety, wherein detectable properties of the different label moieties are distinguishable.

36. The composition of paragraph 35, wherein the first and second nucleic acid strands hybridize to form a double-stranded region of about 6 base-pairs to about 30 base-pairs.

37. The composition of any of paragraphs 35-36, wherein the first and second nucleic acid strands hybridize to form a double-stranded region of about 12 to 16 base-pairs.

38. The composition of any of paragraphs 35-37, wherein the first and second nucleic acid strands hybridize to form a double-stranded region having a melting temperature about 40° C. or above.

39. The composition of any of paragraphs 35-38, wherein the first and second nucleic acid strands hybridize to form a double-stranded region having a 3' or 5' single-stranded overhang of about 6 to about 20 nucleotides.

40. The composition of any of paragraphs 35-39, wherein the affinity molecule and the label moiety are in a 1:1 (affinity molecule: label moiety) ratio.

41. The composition of any of paragraphs 35-40, wherein
    (i) the affinity molecule is conjugated to 3' terminus of the first nucleic acid strand and the label moiety is conjugated to 3' terminus of the second nucleic acid strand; or
    (ii) the affinity molecule is conjugated to 5' terminus of the first nucleic acid strand and the label moiety is conjugated to 5' terminus of the second nucleic acid strand.

42. The composition of any of paragraphs 35-41, wherein at least one of the first or the second strands of nucleic acid comprises a modification selected from the group consisting of nucleobase modifications, sugar modifications, inter-sugar linkage modifications, backbone modifications, and any combinations thereof.

43. The composition of any of paragraphs 35-42, wherein the affinity molecule is an antibody or antigen-binding portion thereof.

44. The composition of any of paragraphs 35-43, wherein the affinity molecule is covalently linked to the first nucleic acid strand through a linker or the affinity molecule is non-covalently linked to the first nucleic acid strand through an adaptor molecule.

45. The composition of paragraph 44, wherein the linker is a bond, succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bisaryl hydrazone bond, an amide bond, tow amide bonds on a spacer for cross-linking two —NH2 groups, triazole bond (from "click" reaction), a phosphodiester linkage, a phsophothioate linkage, or any combination thereof.

46. The composition of paragraph 44, wherein the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.

47. The composition of any of paragraphs 35-46, wherein the label moiety is covalently linked to the second nucleic acid strand through a linker or wherein the label moiety is non-covalently linked to the second nucleic acid via a coupling pair.

48. The composition of any of paragraphs 35-47, wherein the label moiety is selected from the group consisting of a luminescent nanoparticle, fluorescent molecule, chemiluminescent moiety, bioluminescent moiety, luminescent molecule, radioisotope, chromophore, magnetic nanoparticles, plasmonic nanoparticles, upconverting nanoparticles, nanoparticles comprising fluorescent molecules, nanoparticles comprising fluorophores, and any combination thereof.

49. The composition of paragraph 48, wherein the luminescent nanoparticle is an inorganic semiconductor nanoparticle chosen from group consisting of a Group II, Group III, Group IV, Group V, and Group VI semiconductor nanoparticles.

50. The composition of paragraph 48 or 49, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.

51. The composition of any of paragraphs 48-50, wherein the luminescent nanoparticle is core type or core-shell type.

52. The composition of any of paragraphs 48-51, wherein the luminescent nanoparticle comprises a core and a shell forms a colloidal particle.

53. The composition of any of paragraphs 48-52, wherein the luminescent nanoparticle core comprises CdSe and the shell comprises ZnS.

54. The composition of any of paragraphs 48-53, wherein the luminescent nanoparticle is about 1 nm to about 100 nm in size.
55. The composition of any of paragraphs 48-54, wherein the luminescent nanoparticle comprises a polymer coating layer.
56. The composition of paragraph 55, wherein the polymer is polyethylene glycol.
57. The composition of any of paragraphs 48-56, wherein emission spectra of the different luminescent nanoparticles are distinguishable.
58. The composition of any of paragraphs 48-57, wherein the luminescent nanoparticle is a colloidal water-soluble nanoparticle comprising a stable non-fouling coating such that non-specific binding of the nanoparticle to a cell or a tissue sample is reduced relative to a nanoparticle lacking a non-fouling coating.
59. A composition comprising a plurality of different affinity molecules, each member of the plurality binding a different target, wherein each different affinity molecule is reversibly conjugated to a luminescent nanoparticle, in which the nanoparticle is covalently linked to an adaptor molecule and the adaptor molecule is non-covalently linked to the affinity molecule, wherein the affinity molecule and the adaptor molecule are present in a 1:1 ratio, and wherein the luminescent nanoparticle is a colloidal water-soluble nanoparticle comprising a stable non-fouling coating such that non-specific binding of the nanoparticle to a cell or a tissue sample is reduced relative to a nanoparticle lacking a non-fouling coating, and wherein emission spectra of the different luminescent nanoparticles are distinguishable.
60. The composition of paragraph 59, wherein the affinity molecule is an antibody or antigen-binding portion thereof.
61. The composition of any of paragraphs 59 or 60, the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.
62. The composition of any of paragraphs 59-61, wherein the luminescent nanoparticle is an inorganic semiconductor nanoparticle chosen from group consisting of a Group II, Group III, Group IV, Group V, and Group VI semiconductor nanoparticles.
63. The composition of paragraph 59, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.
64. The composition any of paragraphs 59-63, wherein the luminescent nanoparticle is core type or core-shell type.
65. The composition of any of paragraphs 59-64, wherein the luminescent nanoparticle comprises a core and a shell forms a colloidal particle.
66. The composition any of paragraphs 59-65, wherein the luminescent nanoparticle core comprises CdSe and the shell comprises ZnS.
67. The composition any of paragraphs 59-66, wherein the luminescent nanoparticle is about 1 nm to about 100 nm in size.
68. The composition any of paragraphs 59-67, wherein the luminescent nanoparticle comprises a polymer coating layer.
69. The composition of paragraph 68, wherein the polymer is polyethylene glycol.
70. A composition comprising a solid support comprising a sample for analysis for the presence of analytes, and a plurality of different affinity molecules, each member of the plurality of different affinity molecules conjugated to a first single-strand nucleic acid, wherein each member of the plurality of different affinity molecules is bound to a different analyte in the sample, and wherein each first single-strand nucleic acid has a different nucleotide sequence.
71. The composition of paragraph 70, wherein the composition further comprises a plurality of different second single strand nucleic acid molecules, each conjugated to a different label moiety, wherein each different second single strand nucleic acid molecule specifically hybridizes to a different first single strand nucleic acid molecule conjugated to a member of the plurality of different affinity molecules, such that at least a subset of the plurality of different affinity molecules bound to the analytes in the cell or tissue sample is specifically associated with a plurality of different label moiety, wherein detectable properties of the different label moieties are distinguishable.
72. The composition of paragraph 71, wherein the first and second nucleic acid strands hybridize to form a double-stranded region of about 6 base-pairs to about 30 base-pairs.
73. The composition of paragraph 72, wherein the first and second nucleic acid strands hybridize to form a double-stranded region of about 12 to about 16 base-pairs.
74. The composition of any of paragraphs 71-73, wherein the first and second nucleic acid strands hybridize to form a double-stranded region having a melting temperature about 40° C. or above.
75. The composition of any of paragraphs 71-74, wherein the first and second nucleic acid strands hybridize to form a double-stranded region having a 3' or 5' single-stranded overhang of about 6 to about 20 nucleotides.
76. The composition of any of paragraphs 71-75, wherein the affinity molecule and the label moiety are in a 1:1 (affinity molecule: label moiety) ratio.
77. The composition of any of paragraphs 71-76, wherein
 (i) the affinity molecule is conjugated to 3' terminus of the first nucleic acid strand and the label moiety is conjugated to 3' terminus of the second nucleic acid strand; or
 (ii) the affinity molecule is conjugated to 5' terminus of the first nucleic acid strand and the label moiety is conjugated to 5' terminus of the second nucleic acid strand.
78. The composition of any of paragraphs 71-77, wherein at least one of the first or the second strands of nucleic acid comprises a modification selected from the group consisting of nucleobase modifications, sugar modifications, inter-sugar linkage modifications, backbone modifications, and any combinations thereof.
79. The composition of any of paragraphs 70-78, wherein the affinity molecule is an antibody or antigen-binding portion thereof.
80. The composition of any of paragraphs 70-79, wherein the affinity molecule is covalently linked to the first nucleic acid strand through a linker or the affinity molecule is non-covalently linked to the first nucleic acid strand through an adaptor molecule.
81. The composition of paragraph 80, wherein the linker is a bond, succinimidyl-4-(N-maleimidomethyl)cyclohexane- 1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond, an amide bond, tow amide bonds on a spacer for cross-linking two —NH2 groups, triazole bond (from "click" reaction), a phosphodiester linkage, a phsophothioate linkage, or any combination thereof.

82. The composition of any of paragraphs 70-81, wherein the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.

83. The composition of any of paragraphs 71-82, wherein the label moiety is covalently linked to the second nucleic acid strand through a linker or the label moiety is non-covalently linked to the second nucleic acid via a coupling pair.

84. The composition of any of paragraphs 71-83, wherein the label moiety is selected from the group consisting of a luminescent nanoparticle, fluorescent molecule, chemiluminescent moiety, bioluminescent moiety, luminescent molecule, radioisotope, chromophore, magnetic nanoparticles, plasmonic nanoparticles, upconverting nanoparticles, nanoparticles comprising fluorescent molecules, nanoparticles comprising fluorophores, and any combination thereof.

85. The composition of paragraph 84, wherein the luminescent nanoparticle is an inorganic semiconductor nanoparticle chosen from group consisting of a Group II, Group III, Group IV, Group V, and Group VI semiconductor nanoparticles.

86. The composition of paragraph 84 or 85, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.

87. The composition of any of paragraphs 84-86, wherein the luminescent nanoparticle is core type or core-shell type.

88. The composition of any of paragraphs 84-87, wherein the luminescent nanoparticle comprises a core and a shell forms a colloidal particle.

89. The composition of any of paragraphs 84-88, wherein the luminescent nanoparticle core comprises CdSe and the shell comprises ZnS.

90. The composition of any of paragraphs 84-89, wherein the luminescent nanoparticle is about 1 nm to about 100 nm in size.

91. The composition of any of paragraphs 84-90, wherein the luminescent nanoparticle comprises a polymer coating layer.

92. The composition of paragraph 91, wherein the polymer is polyethylene glycol.

93. The composition of any of paragraphs 84-92, wherein the luminescent nanoparticle is a colloidal water-soluble nanoparticle comprising a stable non-fouling coating such that non-specific binding of the nanoparticle to a cell or a tissue sample is reduced relative to a nanoparticle lacking a non-fouling coating.

94. A kit comprising a composition of paragraph 1, 24, or 35.

95. A method of analyzing a sample for a plurality of analytes, the method comprising, in order:

(h) contacting the sample with a plurality of different affinity molecules under conditions that permit specific analyte binding by the different affinity molecules, wherein each different affinity molecule specifically binds a different member of the plurality of analytes, and wherein each different affinity molecule is conjugated to a different first single strand nucleic acid, such that members of the plurality of different affinity molecules become bound to members of the plurality of analytes present in the sample;

(i) contacting the sample, under conditions that permit specific nucleic acid hybridization, with a first set of different second single strand nucleic acid molecules, each conjugated to a different label moiety, wherein each different second single strand nucleic acid molecule specifically hybridizes to a different first single strand nucleic acid molecule conjugated to a member of the plurality of different affinity molecules, such that at least a subset of the plurality of different affinity molecules bound to members of the plurality of analytes in the sample becomes specifically associated with a plurality of different label moieties, wherein detectable properties of the different label moieties are distinguishable; and (j) detecting signal from label moieties associated with affinity molecules bound to the sample, thereby detecting the presence or amount of at least a subset of the plurality of analytes.

96. The method of paragraph 95, further comprising the steps of:

(k) quenching the signal from the label moieties conjugated to the first set of second single strand nucleic acid molecules;

(l) contacting the sample, under conditions that permit specific nucleic acid hybridization, with a second set of different second single strand nucleic acid molecules, each conjugated to a different label, wherein each different second single strand nucleic acid molecule specifically hybridizes to a different first single strand nucleic acid molecule conjugated to a member of the plurality of different affinity molecules, such that a different subset of the plurality of different affinity molecules bound to members of the plurality of analytes in the sample becomes specifically associated with a different plurality of different label moieties relative to those detected in step (c);

(m) detecting signal from label moieties associated with affinity molecules bound to the sample, thereby detecting the presence or amount of the different subset of the plurality of analytes; and (n) optionally repeating steps (d)-(f) with a further set of second single strand nucleic acid molecules.

97. The method of paragraph 95 or 96, wherein said detecting comprises imaging spectral emissions.

98. The method of paragraph 97, wherein said imaging is hyperspectral imaging or multispectral imaging.

99. The method of any of paragraphs 95-98, wherein said detecting comprises spectral unmixing.

100. The method of any of paragraphs 96-99, wherein said quenching comprises removing the label moieties from the sample or quenching fluorescent signal from the label moieties.

101. The method of any of paragraphs 96-100, wherein said quenching is chemical or physical.

102. The method of any of paragraphs 96-101, wherein said quenching is by elution, denaturation, washing, displacement, cleavage, photo-bleaching, heating, quenching with a fluorophore acceptor, or a combination thereof.

103. The method of any of paragraphs 96-102, wherein said quenching is by washing with a low pH buffer.

104. The method of any of paragraphs 96-103, wherein said quenching is by nucleic acid strand displacement or nucleic acid cleavage.

105. The method of paragraph 104, wherein said strand displacement is by adding an oligonucleotide comprising a nucleic acid sequence complementary to the first or second strands of nucleic acid.

106. The method of any of paragraphs 95-105, further comprising one or more wash steps.

107. The method of any of paragraphs 95-107, further comprising one or more blocking steps.

108. The method of any of paragraphs 95-107, wherein the first and second nucleic acid strands hybridize to form a double-stranded region of about 6 base-pairs to about 30 base-pairs.

109. The method of any of paragraphs 95-108, wherein the first and second nucleic acid strands hybridize to form a double-stranded region of about 12 to about 16 base-pairs.

110. The method of any of paragraphs 95-109, wherein the first and second nucleic acid strands hybridize to form a double-stranded region having a melting temperature about 40° C. or above.

111. The method of any of paragraphs 95-110, wherein the first and second nucleic acid strands hybridize to form a double-stranded region having a 3' or 5' single-stranded overhang of about 6 to about 20 nucleotides.

112. The method of any of paragraphs 95-111, wherein the affinity molecule and the label moiety are in a 1:1 (affinity molecule: label moiety) ratio.

113. The method of any of paragraphs 95-112, wherein
   (i) the affinity molecule is conjugated to 3' terminus of the first nucleic acid strand and the label moiety is conjugated to 3' terminus of the second nucleic acid strand; or
   (ii) the affinity molecule is conjugated to 5' terminus of the first nucleic acid strand and the label moiety is conjugated to 5' terminus of the second nucleic acid strand.

114. The method of any of paragraphs 95-113, wherein at least one of the first or the second strands of nucleic acid comprises a modification selected from the group consisting of nucleobase modifications, sugar modifications, inter-sugar linkage modifications, backbone modifications, and any combinations thereof.

115. The method of any of paragraphs 95-114, wherein the affinity molecule is an antibody or antigen-binding portion thereof.

116. The method of any of paragraphs 95-115, wherein the affinity molecule is covalently linked to the first nucleic acid strand through a linker or the affinity molecule is non-covalently linked to the first nucleic acid strand through an adaptor molecule.

117. The method of paragraph 116, wherein the linker is a bond, succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond, an amide bond, tow amide bonds on a spacer for cross-linking two —NH2 groups, triazole bond (from "click" reaction), a phosphodiester linkage, a phsophothioate linkage, or any combination thereof.

118. The method of any of paragraphs 95-117, wherein the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.

119. The method of any of paragraphs 95-118, wherein the label moiety is covalently linked to the second nucleic acid strand through a linker or the label moiety is non-covalently linked to the second nucleic acid via a coupling pair.

120. The method of any of paragraphs 95-119, wherein the label moiety is selected from the group consisting of a luminescent nanoparticle, fluorescent molecule, chemiluminescent moiety, bioluminescent moiety, luminescent molecule, radioisotope, chromophore, magnetic nanoparticles, plasmonic nanoparticles, upconverting nanoparticles, nanoparticles comprising fluorescent molecules, nanoparticles comprising fluorophores, and any combination thereof.

121. The method of paragraph 120, wherein the luminescent nanoparticle is an inorganic semiconductor nanoparticle chosen from group consisting of a Group II, Group III, Group IV, Group V, and Group VI semiconductor nanoparticles.

122. The method of paragraph 120 or 121, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.

123. The method of any of paragraphs 120-122, wherein the luminescent nanoparticle is core type or core-shell type.

124. The method of any of paragraphs 120-123, wherein the luminescent nanoparticle comprises a core and a shell forms a colloidal particle.

125. The method of any of paragraphs 120-124, wherein the luminescent nanoparticle core comprises CdSe and the shell comprises ZnS.

126. The method of any of paragraphs 120-125, wherein the luminescent nanoparticle is about 1 nm to about 100 nm in size.

127. The method of any of paragraphs 120-126, wherein the luminescent nanoparticle comprises a polymer coating layer.

128. The method of 120-127, wherein the polymer is polyethylene glycol.

129. The method of any of paragraphs 120-128, wherein the luminescent nanoparticle is a colloidal water-soluble nanoparticle comprising a stable non-fouling coating such that non-specific binding of the nanoparticle to a cell or a tissue sample is reduced relative to a nanoparticle lacking a non-fouling coating.

130. The method of any of paragraphs 120-129, wherein emission spectra of the different luminescent nanoparticles are distinguishable.

131. A method of analyzing a sample for a plurality of analytes, the method comprising, in order:
   (g) contacting the sample with a first plurality of different affinity molecules under conditions that permit specific analyte binding by the different affinity molecules, wherein each different affinity molecule specifically binds a different member of the plurality of analytes, wherein each different affinity molecule is conjugated to a different first single strand nucleic acid molecule that is specifically hybridized to a second single strand nucleic acid molecule, wherein the second single strand nucleic acid molecule is conjugated to a label moiety, such that each different affinity molecule is conjugated via different hybridized first and second nucleic acid strands to a different label moiety and members of the plurality of different affinity molecules become bound to members of the plurality of analytes present in the sample, wherein detectable properties of the label moieties are distinguishable; and (h) detecting signal from label moieties associated with first plurality of affinity molecules bound to the sample, thereby detecting the presence or amount of the plurality of analytes.

132. The method of paragraph 131, further comprising the steps of:
(i) quenching the signal from the label molecules conjugated to the first set of second single strand nucleic acid molecules;
(j) contacting the sample with a second plurality of different affinity molecules under conditions that permit specific analyte binding by the different affinity molecules;
(k) detecting signal from label moieties associated with second plurality of affinity molecules bound to the sample, thereby detecting the presence or amount of at least a subset of the plurality of analytes; and
(l) optionally repeating steps (c)-(e) with a further second set of the affinity molecules.

133. The method of paragraph 131 or 132, wherein said detecting comprises imaging spectral emissions.

134. The method of paragraph 133, wherein said imaging is hyperspectral imaging or multispectral imaging.

135. The method of any of paragraphs 131-134, wherein said detecting comprises spectral unmixing.

136. The method of any of paragraphs 132-135, wherein said quenching comprises removing the label moieties from the sample or quenching fluorescent signal from the label moieties.

137. The method of any of paragraphs 132-136, wherein said quenching is chemical or physical.

138. The method of any of paragraphs 132-137, wherein said quenching is by elution, denaturation, washing, displacement, cleavage, photo-bleaching, heating, quenching with a fluorophore acceptor, or a combination thereof.

139. The method of any of paragraphs 132-138, wherein said quenching is by washing with a low pH buffer.

140. The method of any of paragraphs 132-138, wherein said quenching is by nucleic acid strand displacement or nucleic acid cleavage.

141. The method of paragraph 140, wherein said strand displacement is by adding an oligonucleotide comprising a nucleic acid sequence complementary to the first or second strands of nucleic acid.

142. The method of any of paragraphs 131-141, further comprising one or more wash steps.

143. The method of any of paragraphs 131-142, further comprising one or more blocking steps.

144. The method of any of paragraphs 131-143, wherein the first and second nucleic acid strands hybridize to form a double-stranded region of about 6 base-pairs to about 30 base-pairs.

145. The method any of paragraphs 131-144, wherein the first and second nucleic acid strands hybridize to form a double-stranded region of about 12 to about 16 base-pairs.

146. The method any of paragraphs 131-145, wherein the first and second nucleic acid strands hybridize to form a double-stranded region having a melting temperature about 40° C. or above.

147. The method any of paragraphs 131-146, wherein the first and second nucleic acid strands hybridize to form a double-stranded region having a 3' or 5' single-stranded overhang of about 6 to about 20 nucleotides.

148. The method any of paragraphs 131-147, wherein the affinity molecule and the label moiety are in a 1:1 (affinity molecule: label moiety) ratio.

149. The method any of paragraphs 131-148, wherein
(i) the affinity molecule is conjugated to 3' terminus of the first nucleic acid strand and the label moiety is conjugated to 3' terminus of the second nucleic acid strand; or
(ii) the affinity molecule is conjugated to 5' terminus of the first nucleic acid strand and the label moiety is conjugated to 5' terminus of the second nucleic acid strand.

150. The method any of paragraphs 131-149, wherein at least one of the first or the second strands of nucleic acid comprises a modification selected from the group consisting of nucleobase modifications, sugar modifications, inter-sugar linkage modifications, backbone modifications, and any combinations thereof.

151. The method any of paragraphs 131-150, wherein the affinity molecule is an antibody or antigen-binding portion thereof.

152. The method of any of paragraphs 131-151, wherein the affinity molecule is covalently linked to the first nucleic acid strand through a linker or the affinity molecule is non-covalently linked to the first nucleic acid strand through an adaptor molecule.

153. The method of paragraph 152, wherein the linker is a bond, succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond, an amide bond, tow amide bonds on a spacer for cross-linking two —NH2 groups, triazole bond (from "click" reaction), a phosphodiester linkage, a phsophothioate linkage, or any combination thereof.

154. The method of any of paragraphs 131-153, wherein the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.

155. The method of any of paragraphs 131-154, wherein the label moiety is covalently linked to the second nucleic acid strand through a linker or the label moiety is non-covalently linked to the second nucleic acid via a coupling pair.

156. The method of any of paragraphs 131-155, wherein the label moiety is selected from the group consisting of a luminescent nanoparticle, fluorescent molecule, chemiluminescent moiety, bioluminescent moiety, luminescent molecule, radioisotope, chromophore, magnetic nanoparticles, plasmonic nanoparticles, upconverting nanoparticles, nanoparticles comprising fluorescent molecules, nanoparticles comprising fluorophores, and any combination thereof.

157. The method of paragraph 156, wherein the luminescent nanoparticle is an inorganic semiconductor nanoparticle chosen from group consisting of a Group II, Group III, Group IV, Group V, and Group VI semiconductor nanoparticles.

158. The method of any of paragraphs 156-157, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.

159. The method of any of paragraphs 156-158, wherein the luminescent nanoparticle is core type or core-shell type.

160. The method of any of paragraphs 156-159, wherein the luminescent nanoparticle comprises a core and a shell forms a colloidal particle.

161. The method of any of paragraphs 156-160, wherein the luminescent nanoparticle core comprises CdSe and the shell comprises ZnS.

162. The method of any of paragraphs 156-161, wherein the luminescent nanoparticle is about 1 nm to about 100 nm in size.

163. The method of any of paragraphs 156-162, wherein the luminescent nanoparticle comprises a polymer coating layer.

164. The method of paragraph 163, wherein the polymer is polyethylene glycol.

165. The method of any of paragraphs 156-164, wherein the luminescent nanoparticle is a colloidal water-soluble nanoparticle comprising a stable non-fouling coating such that non-specific binding of the nanoparticle to a cell or a tissue sample is reduced relative to a nanoparticle lacking a non-fouling coating.

166. The method of any of paragraphs 156-165, wherein emission spectra of the different luminescent nanoparticles are distinguishable.

167. A method of analyzing a sample for a plurality of analytes, the method comprising, in order:
(a) contacting the sample with a first plurality of different affinity molecules under conditions that permit specific analyte binding by the different affinity molecules, wherein each different affinity molecule specifically binds a different member of the plurality of analytes and members of the plurality of different affinity molecules become bound to members of the plurality of analytes present in the sample, wherein each different affinity molecule is reversibly conjugated to a different luminescent nanoparticle, in which the nanoparticle is covalently linked to an adaptor molecule and the adaptor molecule is non-covalently linked to the affinity molecule, the affinity molecule and the adaptor molecule are present in a 1:1 ratio, and wherein the luminescent nanoparticle is a colloidal water-soluble nanoparticle comprising a stable non-fouling coating such that non-specific binding of the nanoparticle to a cell or a tissue sample is reduced relative to a nanoparticle lacking a non-fouling coating, and detectable properties of the luminescent nanoparticles are distinguishable; and
(b) detecting signal from luminescent nanoparticles associated with the first plurality of affinity molecules bound to the sample, thereby detecting the presence or amount of the plurality of analytes.

168. The method of paragraph 167, further comprising the steps of:
(c) quenching the signal from the luminescent nanoparticles conjugated to the first set of different second single strand nucleic acid molecules;
(d) contacting the sample with a second set of the plurality of different affinity molecules under conditions that permit specific analyte binding by the different affinity molecules;
(e) detecting signal from luminescent molecules associated with second set of affinity molecules bound to the sample, thereby detecting the presence or amount of at least a subset of the plurality of analytes; and
(f) optionally repeating steps (c)-(e) with a further second set of the affinity molecules.

169. The method of paragraph 167 or 168, wherein said detecting comprises imaging spectral emissions.

170. The method of paragraph 169, wherein said imaging is hyperspectral imaging or multispectral imaging.

171. The method of any of paragraphs 167-170, wherein said detecting comprises spectral unmixing.

172. The method of any of paragraphs 167-171, wherein said quenching comprises removing the luminescent nanoparticles from the sample or quenching fluorescent signal from the label moieties.

173. The method of any of paragraphs 167-172, wherein said quenching is chemical or physical.

174. The method of any of paragraphs 167-173, wherein said quenching is by elution, denaturation, washing, displacement, cleavage, photo-bleaching, heating, quenching with a fluorophore acceptor, or a combination thereof.

175. The method of any of paragraphs 167-174, wherein said quenching is by washing with a low pH buffer.

176. The method of any of paragraphs 167-175, further comprising one or more wash steps.

177. The method of any of paragraphs 167-176, further comprising one or more blocking steps.

178. The method of any of paragraphs 167-177, wherein the affinity molecule is an antibody or antigen-binding portion thereof.

179. The method of any of paragraphs 167-178, wherein the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.

180. The method of any of paragraphs 167-179, wherein the luminescent nanoparticle is an inorganic semiconductor nanoparticle chosen from group consisting of a Group II, Group III, Group IV, Group V, and Group VI semiconductor nanoparticles.

181. The method of any of paragraphs 167-180, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.

182. The method of any of paragraphs 167-181, wherein the luminescent nanoparticle is core type or core-shell type.

183. The method of any of paragraphs 167-182, wherein the luminescent nanoparticle comprises a core and a shell forms a colloidal particle.

184. The method of paragraph 183, wherein the luminescent nanoparticle core comprises CdSe and the shell comprises ZnS.

185. The method of any of paragraphs 167-184, wherein the luminescent nanoparticle is about 1 nm to about 100 nm in size.

186. The method of any of paragraphs 167-185, wherein the luminescent nanoparticle comprises a polymer coating layer.

187. The method of paragraph 186, wherein the polymer is polyethylene glycol.

188. The method of any of paragraphs 70-93, wherein the solid support an ELISA plate, a magnetic bead, an agarose bead, a western blot membrane, or a combination thereof.
189. The method of any of paragraphs 70-93 or 188, wherein the sample is a cell or a tissue sample.

To the extent not already indicated, it will be understood by those of ordinary skill in the art that any one of the various embodiments herein described and illustrated can be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Hybrid IF/FISH Procedure for Molecular Profiling of Cells and Tissue Specimens

Conventional 2-step staining procedures utilize links with no (e.g. streptavidin/biotin) or limited (e.g. primary/secondary antibodies) selectivity, thus prohibiting highly multiplexed biomarker detection. Therefore, the inventors designed a hybrid IF/FISH 2-step staining procedure featuring highly selective links for unique assignment of FL probes to corresponding biomarkers. This functionality can be achieved by encoding each biomarker with a unique DNA tag via specific recognition by oligonucleotide-labeled 1'Ab. Conversion of biomarker antigenicity information into a DNA sequence code enables performance of a highly multiplexed FISH-like staining procedure with complementary FL-oligonucleotide probes (FIG. 1). With this method design, simultaneous encoding of a large number of biomarkers is possible, several of which can be labeled with FL probes in parallel and analyzed by spectral imaging. The inventor have optimized this method for QD-DNA probes to gain higher multiplexing potential, while demonstrating applicability of conventional FISH probes based on organic fluorophores for staining with lower parallel multiplexing capability. Furthermore, the utility of cyclic staining is demonstrated herein for expanding the number of biomarkers analyzed on the same specimen. After staining and imaging, specimen is de-stained at gentle conditions via DNA link displacement with longer oligonucleotides (FIG. 1), which achieves complete removal of FL probes, while exhibiting no interference with antigen-antibody binding, thus leaving the first layer of Ab-DNA tags intact. Therefore, de-staining is achieved at physiological conditions, preserving biomarker antigenicity and eliminating the need for antigen re-detection on each cycle. After de-staining, another sub-set of biomarkers can be stained via detection of corresponding DNA tags. The hybrid IF/FISH staining system described in this example generally involves: (i) method for preparation of oligonucleotide-labeled primary antibodies (Ab-DNA); (ii) preparation of oligonucleotide-functionalized QD probes (QD-DNA); and (iii) optimization of multiplexed 2-step staining procedure on formalin-fixed and permeabilized cells. The method provides substantial flexibility in probe design depending on particular application needs. For example, the length and structure of DNA link can be optimized to offer selectivity of bond formation, sufficient stability, and capacity for quick displacement with longer oligonucleotide for de-staining purposes. Labeling of primary antibodies with ssDNA can be achieved using, among others, the following strategies: (i) covalent conjugation with reduced IgG via reaction with sulfhydryl group in Fc region; (ii) covalent conjugation with whole IgG via cross-linking with primary amines; and (iii) non-covalent self-assembly of intact whole IgG with DNA-carrying adaptor protein (on the basis of protein A from *Staphylococcus aureus*, SpA, or Fc-specific Fab antibody fragments). Preparation of QD-DNA probes, in turn, can be done based on 3 different QD platforms: (i) compact zwitterionic QDs can be used for EDC-mediated conjugation; (ii) larger PEG-coated QDs can be used for BS3-mediated cross-linking with amine groups; and (iii) streptavidin-functionalized QDs can be used for non-covalent capture of biotinylated oligonucleotides. Each approach has benefits and drawbacks in terms of complexity and yield of conjugation reaction, control over the final structure of bioconjugates, and stability of probes; yet every combination of probes satisfies basic criteria imposed by the hybrid IF/FISH method, while enabling flexibility in system design for addressing specific needs of a wide range of applications.

DNA Link Design:

DNA-encoded antibodies prepared with a variety of covalent and non-covalent procedures have been used for a number of bio-analytical methods (Bailey, R. C., et al., *DNA-encoded antibody libraries: a unified platform for multiplexed cell sorting and detection of genes and proteins.* Journal of the American Chemical Society, 2007. 129(7): p. 1959-67 and Lind, K. and M. Kubista, *Development and evaluation of three real-time immuno-PCR assemblages for quantification of PSA.* Journal of Immunological Methods, 2005. 304(1-2): p. 107-16). At the same time, QD-oligonucleotide probes have been developed for DNA detection and FISH applications (Chan, P., et al., *Method for multiplex cellular detection of mRNAs using quantum dot fluorescent in situ hybridization.* Nucleic Acids Res, 2005. 33(18): p. e161; Matsuno, A., et al., *Three-dimensional imaging of the intracellular localization of growth hormone and prolactin and their mRNA using nanocrystal (Quantum dot) and confocal laser scanning microscopy techniques.* J Histochem Cytochem, 2005. 53(7): p. 833-8; Tholouli, E., et al., *Imaging of multiple mRNA targets using quantum dot based in situ hybridization and spectral deconvolution in clinical biopsies.* Biochemical and Biophysical Research Communications, 2006. 348(2): p. 628-36; Cady, N. C., A. D. Strickland, and C. A. Batt, *Optimized linkage and quenching strategies for quantum dot molecular beacons.* Molecular and Cellular Probes, 2007. 21(2): p. 116-2; Gueroui, Z. and A. Libchaber, *Single-molecule measurements of gold-quenched quantum dots.* Physical Review Letters, 2004. 93(16): p. 166108; and Lim, S. H., et al., *Specific nucleic acid detection using photophysical properties of quantum dot probes.* Analytical Chemistry, 2010. 82(3): p. 886-91). Among these studies, the length and structure of DNA link varies significantly, as different criteria have to be satisfied. However, 12-16 base-pair overlap appears to be optimal for providing sufficient bond strength, while minimizing formation of unfavorable secondary structures or significant cross-hybridization between non-matching probes. Therefore, to provide a foundation for further application-specific optimization the inventors designed a panel of 10 unique 16 bp oligonucleotide pairs. Each oligonucleotide was functionalized with a primary amine group on a short PEG spacer to enable covalent conjugation to antibodies and QDs. Each probe was designed to have balanced base content, melting temperature above 45° C., no secondary structures at room temperature, and no more than 4 bp homo-dimers or hetero-dimers with non-matching probes. Those parameters ensured the unique match between DNA-encoded biomarker and complementary QD without probe cross-talk even at non-stringent hybridization conditions. For cyclic staining applications, the link length was shortened to 11 bp and additional 10 bp handle for displacement oligonucleotide was incorporated to enable specimen de-staining at physiological conditions via DNA displacement. The 21 bp displacement probe can quickly and efficiently break the 11 bp bridge between Ab and QD, thus releasing QDs into solution. HPLC-purified oligonucleotides were purchased from IDT DNA. All DNA analysis was performed with an IDT DNA Oligo Analyzer.

Labeling of Primary Antibodies with DNA Tags:

Encoding of biomarkers was achieved via specific recognition and binding by primary antibodies labeled with DNA tags. Preparation of a library of DNA-labeled antibodies was done either via covalent conjugation between Ab and amine-functionalized oligonucleotides or non-covalent self-assembly with SpA-DNA. One covalent conjugation approach involved reduction of IgG followed by maleimidemediated reaction between pre-activated oligonucleotide and sulfhydryl group in Fc region of antibody (FIG. 2A). In particular, antibody was incubated with either dithiothreitol (DTT) or 2-mercaptoethylamine (2-MEA) for 1 hour at ambient conditions and desalted twice with Pierce protein desalting spin columns. Concurrently, amine-functionalized oligonucleotides were activated with sulfo-SMCC for 1 hour and desalted. At least 2 consecutive rounds of desalting were required to completely eliminate excess cross-linker. Reduced Ab and activated DNA at 20 times molar excess were reacted for 5 hours, quenched with mercaptoethanol, and buffer-exchanged into 1×PBS. One benefit of this approach is the controlled stoichiometry and structure of Ab-DNA bioconjugate. As reaction is limited to 1-2 sites on Fc region, preparation of antibodies with intact Fab antigen recognition region and single oligonucleotide attached is readily achievable. This can be important for minimizing potential off-target nuclear binding of Ab-DNA probes. The inventors discovered that a large number of oligonucleotides deposited on biomolecule (e.g. IgG or SpA) led to enhanced nuclear binding in fixed cells, which could not be eliminated by DNA blocking or use of stringent hybridization conditions. To test the off-target binding of Ab-DNA probes prepared via amine-sulfhydryl cross-linking, the inventors functionalized secondary rabbit anti-mouse IgG, incubated with fixed and permeabilized cells after DNA blocking, and detected location of those antibodies with anti-rabbit QD-2'Ab conjugates.

Only minimal nuclear staining was observed, indicating good probe specificity. However, this conjugation strategy showed varied efficiency with different antibodies, exhibiting differences in reaction and purification yield and potentially reducing Ab affinity.

To preserve affinity and specificity of antibodies and improve the yield of conjugation reaction, the inventors utilized an amine cross-linking strategy. While direct reaction with homo-bifunctional cross-linker Bis(Sulfosuccinimidyl) suberate (BS3, which involved initial activation of oligonucleotides followed by incubation with Ab, proceeded with low efficiency (likely due to hydrolysis of active NHS groups during activation and purification steps), an alternative conjugation system utilizing reaction between hydrazide residues and aldehydes successfully produced Ab-DNA conjugates with varying degrees of modification (FIG. 2B). In this procedure Ab was activated by SANH cross-linker, which converted primary amines on antibodies into hydrazide residues reactive towards aldehydes. Excess cross-linker was removed by protein desalting spin column with exchange of buffer to pH5 MES. Amine-modified oligonucleotides were, in turn, reacted with SFB, which converted primary amines into aldehydes, and buffer-exchanged into pH5 MES. Activated antibodies were mixed with modified oligonucleotides at 10-20 DNA molar excess and incubated at room temperature for 5 hours. High stability of reactive intermediates and prolonged reaction time ensured efficient conjugation. The degree of DNA modification could be controlled by the amount of SANH moieties introduced to the antibody; however, the location of oligonucleotide attachment was random. It should be noted that over-modification with DNA led to significant off-target nuclear binding in cells. Therefore, conjugation procedure was optimized to minimize the number of DNA tags on each Ab. Generally, the optimal number of DNA tags provides: unaffected Ab specificity/affinity; very little or no non-specific binding; maximum number of binding sites for labels. Accordingly, in some embodiments, the affinity molecule can comprise from 1 to about 7, e.g., one, two, three, four, five, six or seven, DNA tags. In one embodiment, the affinity molecule can comprise from 2 to 5 DNA tags.

Figure 3:
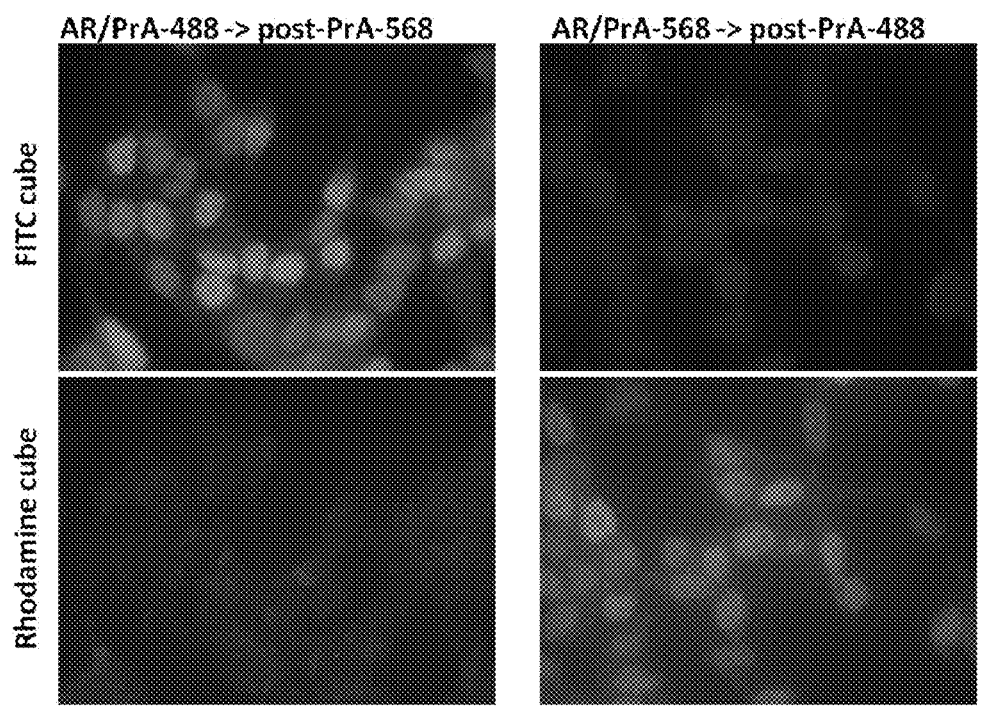
FIG. 3 shows lack of cross-talk between free dye-labeled SpA. Only free SpA pre-assembled with anti-androgen receptor (anti-AR) antibody produced characteristic nuclear staining, while competing SpA failed to stain the target. SpA labeled with Alexa Fluor 488 was imaged with FITC filter, while SpA labeled with Alexa Fluor 568 was imaged with a Rhodamine filter.

Both covalent conjugation procedures tried produced stable and functional Ab-DNA probes. However, the complexity, high cost, and low yield of such custom probe synthesis hampers preparation of a large library of DNA-encoded antibodies. To resolve this issue the inventors have also utilized a universal adaptor protein (SpA) as well as species-matched Fc-specific Fab antibody fragments modified with different DNA strands for on-demand preparation of non-covalent Ab/DNA probes (FIG. 2C). Covalent modification of SpA with oligonucleotides using SANH/SFB procedure is required. However, since SpA is significantly less expensive and more stable compared to primary antibodies, a library of SpA-DNA adaptors can be prepared in large quantities and stored for a long time. Essential to the success of this approach is the lack of SpA-Ab cross-talk and Ab exchange. To demonstrate that SpA-Ab complex exhibit sufficient stability and does not allow Ab exchange, the inventors labeled SpA with organic dyes (either Alexa Fluor 488 or Alexa Fluor 568) and performed cross-talk studies. In particular, the inventors pre-assembled SpA-dye universal probes with 1'Ab raised against androgen receptor (AR, a biomarker with characteristic nuclear localization), then mixed in free SpA labeled with a different dye as a competitor probe and performed staining on fixed cancer cells. Only SpA pre-assembled with anti-AR antibody produced characteristic nuclear staining, while competing SpA failed to capture Ab and showed only minor non-specific staining (FIG. 3). Similarly, the inventors have replicated these studies with oligonucleotide-labeled SpA, demonstrating absolutely no cross-talk between Ab/SpA-DNA probes (data not shown). Therefore, SpA-DNA adaptors can be used for preparation of Ab-DNA libraries for multiplexed 2-step staining.

Figure 4:
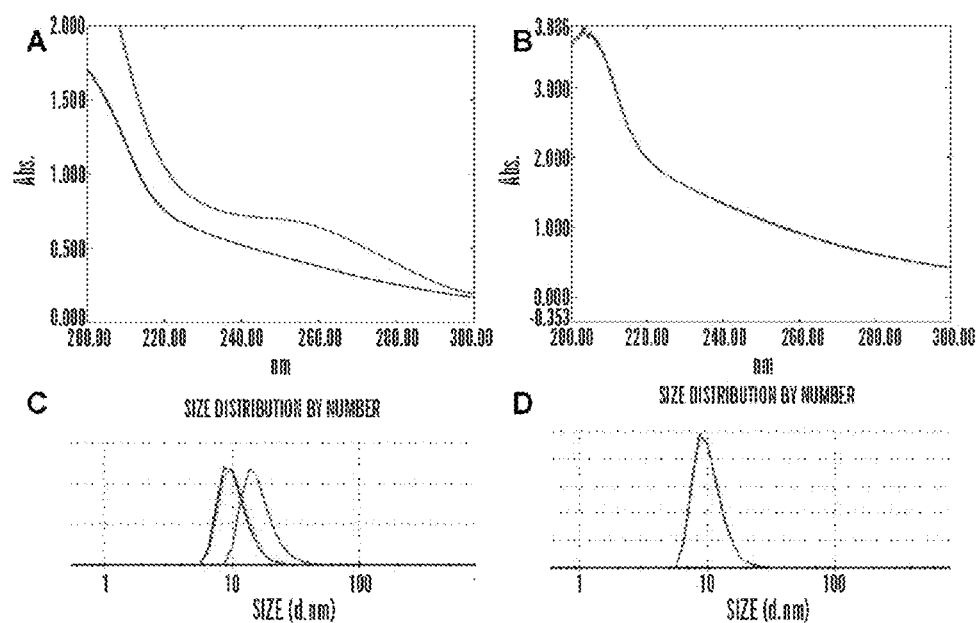
FIGS. 4A-4D show covalent conjugation of amine-modified oligonucleotides to PMAL-coated QDs. QD-oligo conjugates prepared in ~100% DMF showed distinct DNA absorption peak after purification (FIG. 4A) and increase in hydrodynamic size corresponding to deposition of oligonucleotide-PEG on the QD surface (FIG. 4C). Reaction performed under identical conditions in aqueous Bicarbonate buffer failed to produce any QD-oligo conjugates showing no changes in light absorption (FIG. 4B) and particle size (FIG. 4D) in purified samples vs. control.

QD-Oligonucleotide Conjugation:

A complementary library of QD-oligonucleotide probes was prepared using covalent conjugation between amine-modified ssDNA and either carboxy-functionalized or amine-functionalized QDs. At the same time use of streptavidin-coated QDs was validated for flexible on-demand preparation of QD-oligonucleotide probes. Conjugation to carboxylic acid groups of compact zwitterionic QDs was achieved via EDC-mediated coupling. In one experiment, negatively-charged QD-PMAT particles featuring readily-accessible carboxylic acid groups on the surface were incubated with a large excess of EDC and 10-20 molar excess of oligonucleotides overnight. Following the conjugation reaction, the QD surface was back-filled with tertiary amines to yield a zwitterionic coating. In another experiment, QDs pre-coated with zwitterionic polymer PMAL were used. However, unlike PMAT-coated QDs, access to carboxylic acid groups on PMAL is sterically hindered by an abundance of bulky tertiary amines spaced away from the QD surface by C3 linkers. Therefore, while providing a very good barrier to non-specific interaction with biomolecules, chemical modification of such surface can be challenging. Furthermore, an oligonucleotide amine group placed at the end of a PEG spacer on a hydrophobic C6 linker exhibited poor accessibility in aqueous buffers. For example, colorimetric TNBS testing for primary amines detected a significantly higher number of accessible amines on oligonucleotides dissolved in DMSO compared to bicarbonate buffer. Therefore, to resolve accessibility issues, EDC-mediated conjugation between PMAL-coated QDs and amine-modified oligonucleotides was performed in 100% DMSO or DMF solution. Unlike PMAT-coated QDs that showed severe aggregation in DMSO/DMF, QD-PMAL remained single even after addition of small amount of EDC. Some aggregation could happen upon addition of larger amounts of EDC; however, upon resuspension in Borate buffer aggregates broke back into single QDs. QD-oligonucleotide probes were extensively purified with ultrafiltration. Successful conjugation was confirmed by detection of DNA absorption peak at 260 nm in QD-oligo solution and increase in hydrodynamice size from 10 to 11-13 nm (depending on number of DNA tags conjugated) (FIGS. 4A&C). Interestingly, a conjugation reaction with identical conditions performed in Bicarbonate buffer did not produce any QD-oligo conjugates (FIGS. 4B&D). Based on the oligonucleotide and QD absorption it was calculated that 3-4 oligonucleotides were conjugated to each QD.

PEG-coated QDs can represent a more flexible and stable platform for preparation of QD probes, despite larger size and lower accessibility of surface functional groups. Prolonged reaction time necessary for efficiently reaching primary amine groups on the PEG shell can necessitate the use of stable reactive intermediates or repeated re-activation throughout the conjugation procedure. To implement the first approach, the inventors utilized the SANH/SFB system used previously for Ab-DNA conjugation. Similarly, QDs were activated with SANH, while oligonucleotides were modified with SFB. Reaction under mild acidic conditions yielded QD-DNA conjugates. However, modification of PEG shell with SANH moieties caused some increase in non-specific QD cell staining, while a lower degree of activation yielded poor conjugation efficiency. Therefore, the inventors used a second strategy to avoid significant alterations of the QD coating. The second approach consisted of oligonucleotide activation with BS3 followed by quick purification and reaction with PEG-coated QDs. To reverse the effect of hydrolysis of reactive NHS groups, EDC was repeatedly added to reaction mixture in 1-hour intervals, resulting in efficient conjugation. However, modification yield was not as significant as with zwitterionic particles, resulting in no changes in absorption properties and particle size. Surprisingly, besides promoting the conjugation reaction EDC also interacted with carboxylic acid groups buried underneath PEG shell, causing irreversible reduction of QD negative charge and producing nearly neutral particles. Such a side reaction was found to be quite favorable, as the increase in QD negative charge associated with DNA conjugation could induce undesirable electrostatic interactions with fixed cells.

Figure 5:
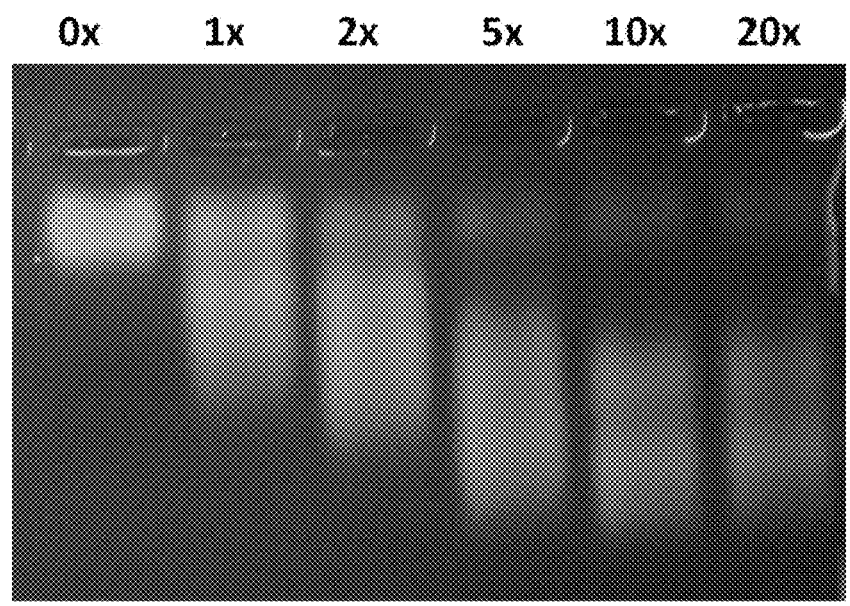
FIG. 5 shows preparation of QD-DNA probes on QD-Streptavidin platform. QD-Str efficiently capture biotinylated ssDNA even at slight DNA excess, as indicated by formation of QD-DNA bands on agarose gel. QD-Str show minimal gel motility (Ox line); however, upon DNA binding, particles become more negatively charged, thus moving faster.

Both covalent conjugation strategies permitted efficient production of stable QD-oligonucleotide probes. Use of those approaches can be suitable for preparation of large quantities of QD-DNA for longterm storage and use with established staining protocols. Streptavidin-coated QDs, on the other hand, offer more flexibility in preparing on-demand probes immediately prior to staining, thus enabling quick testing of new DNA sequences and staining modalities. Straightforward probe self-assembly with relatively controlled stoichiometry can be achieved by simply mixing biotinylated oligonucleotides in slight excess to QD-streptavidin particles and incubating for 30-60 minutes. The inventors discovered that even a small excess of ssDNA (e.g. 2DNA: 1QD) resulted in efficient formation of QD-DNA conjugates (FIG. 5). Depending on the application, larger numbers of DNA can be deposited on QDs. However, purification away from unbound oligonucleotides might be difficult (primarily due to small scale of on-demand probe preparation). Therefore, the inventors also designed a small-scale purification method with streptavidin-coated magnetic beads (MB-Str). Upon mixing with QD-DNA, MB-Str depleted all free ssDNA, thus leaving pure QD-DNA probes. Furthermore, to prevent probe binding to endogenous biotin, the inventors blocked pre-formed and purified QD-DNA probes with excess biotin for 10 minutes prior to staining.

Multiplexed 2-Step Staining of Fixed Cells:

Embodiments of the Hybrid IF/FISH methods described herein involve recognition and DNA encoding of biomarkers in a first step by appropriate Ab-DNA probes and labeling of DNA tags with complementary QD-DNA probes (or FL-DNA probes) in a second step. Since the link between first and second step is established by DNA hybridization, sequence-specific recognition of multiple targets without cross-talk between probes is possible, thus limiting the maximum number of biomarkers detected in parallel only by the current capabilities of spectral imaging and unmixing of different fluorescent probes.

Figure 6:
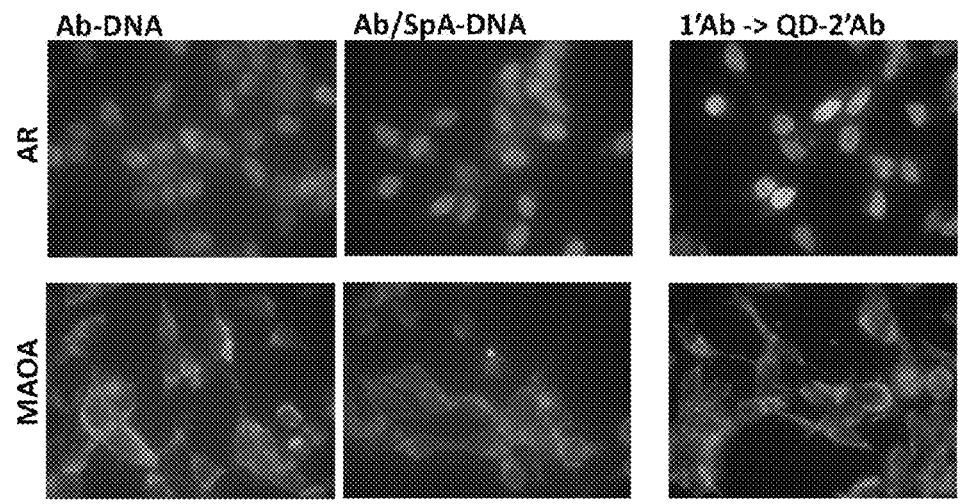
FIG. 6 shows 1-color staining with covalently linked Ab-DNA and self-assembled Ab/SpA-DNA probes. Androgen receptor (AR) and monoamine oxidase A (MAOA) staining patterns obtained with both types of probes were consistent with conventional 2-step staining with QD-2'Ab.
Figure 7:
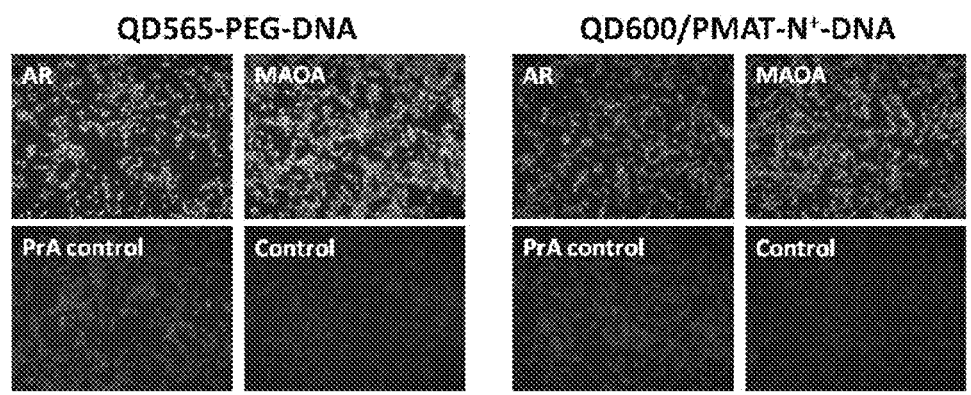
FIG. 7 shows 1-color staining with QD-DNA probes on PEG-coated (left) and zwitterionic (right) particle platform. Clear AR and MAOA staining patterns are produced, while only minimal non-specific binding is observed in controls.
Figure 8:
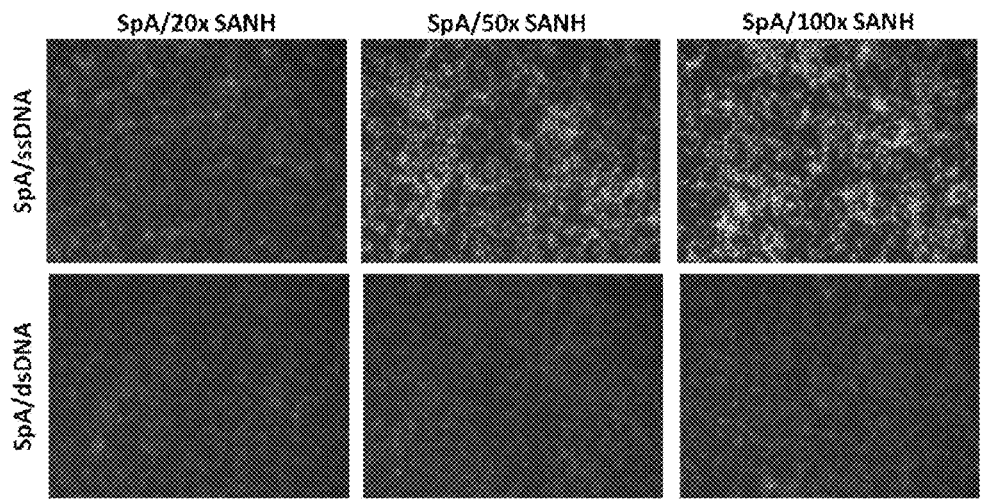
FIG. 8 shows off-target nuclear biding of SpA-DNA probes due to high DNA load. Increasing activation of SpA with succinimidyl 4-hydrazinonicotinate acetone hydrazine (SANH) leads to increased loading of ssDNA per protein, which, in turn, results in enhanced nuclear binding (top row). Partial blocking of ssDNA tag with short oligonucleotide completely eliminates this effect (bottom row).
Figure 9:
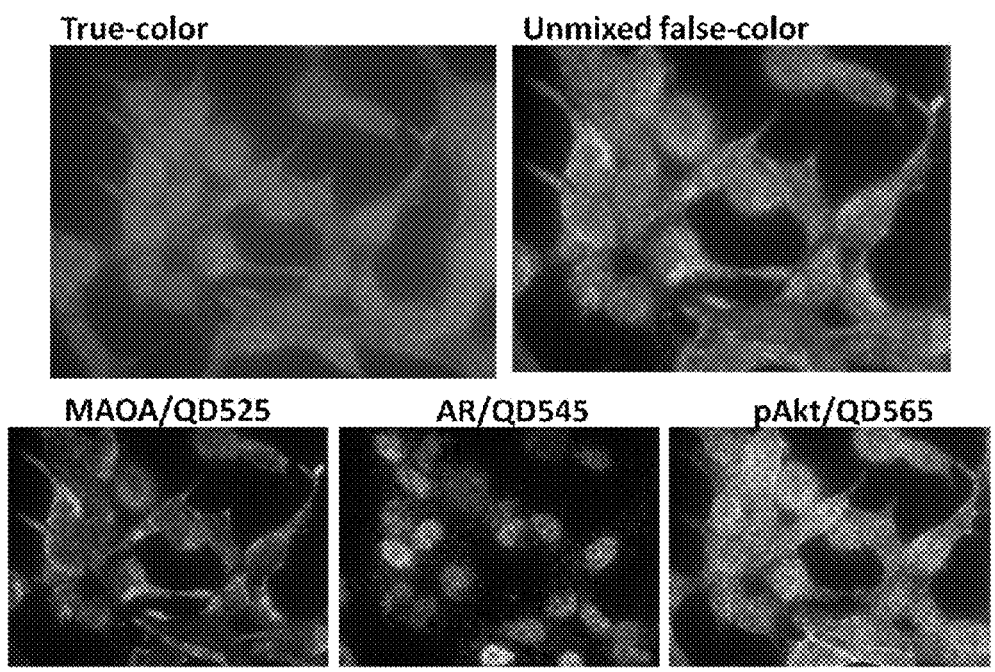
FIG. 9 shows 3-color staining with covalently conjugated Ab-DNA probes. Spectral imaging clearly separated signals from individual QD probes (bottom row), demonstrating consistent staining patterns for MAOA, AR, and pAkt.
Figure 10:
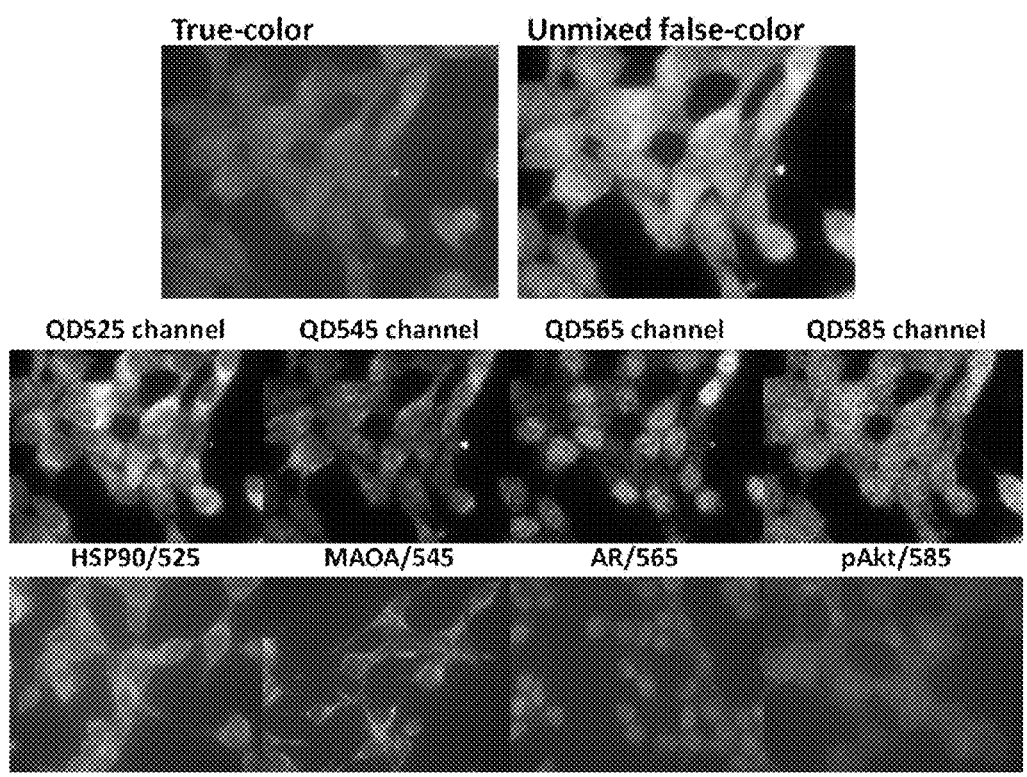
FIG. 10 shows 4-color staining with self-assembled Ab/SpADNA probes. Featuring good Ab/SpA bond stability, these probes exhibited no cross-talk. As a result, multiplexed 2-step staining (middle row) produced biomarker expression patterns consistent with those obtained with single-biomarker staining (bottom row).

In most generic staining of fixed cells any Ab-DNA and QD-DNA probe can be successfully used. To demonstrate this, the inventors prepared formalin-fixed and permeabilized prostate cancer LNCaP cells. Prior to staining, cells were blocked with 6% BSA/TBS buffer with 0.1 mg/mL of sheared salmon sperm DNA to prevent off-target binding of oligonucleotide-functionalized probes. Then cells were contacted with Ab-DNA probes for 1 hour at room temperature, washed, and stained with QD-DNA probes for another hour. Single-color patterns obtained with both types of probes were consistent. Staining of AR and MAOA achieved with either directly conjugated Ab-DNA or self-assembled Ab/SpA-DNA probes showed biomarker staining patterns consistent with those obtained in a 2-step staining procedure with QD-2'Ab conjugates (FIG. 6). Similarly, QD-DNA probes based on both zwitterionic and PEG-coated platforms produced clear staining with minimal nonspecific background (FIG. 7). It should be noted that SpA-DNA probes exhibited slightly enhanced off-target nuclear binding when carrying a large number of oligonucleotides per SpA (FIG. 8, top row). The inventors have developed two solutions to this problem. First, as discussed above, DNA loading of SpA should be minimized, as only a few QDs can sterically fit on SpA regardless of the DNA density. Second, in cases when high DNA loading is required (e.g. when detection is done by organic dyes instead of QDs), SpA-DNA can be hybridized to a short blocking ssDNA sequence, thus forming partial dsDNA tag. Such a construct efficiently eliminated nuclear binding (FIG. 8, bottom row), while being easily removable by a longer complementary ssDNA on QD probe. In multiplexed staining experiments, the hybrid IF/FISH method described herein proved to be robust and specific, exhibiting sufficient DNA link stability and no cross-talk between probes. For example, the inventors have achieved 3-color staining of AR, MAOA, and pAkt with covalently conjugated Ab-DNA probes and QD-PEG-DNA labels (FIG. 9). Spectral imaging clearly extracted signals of green QDs spectrally separated by only 20 nm, yielding consistent biomarker staining patterns in respective QD channels. Similarly, the inventors utilized Ab/SpA-DNA probes for 4-color staining (FIG. 10). Ab/SpA-DNA probes demonstrated good stability and specificity of staining, exhibiting absolutely no cross-talk.

Specimen De-Staining Via DNA Link Displacement:

Hybrid IF/FISH methods described herein are amenable for highly multiplexed parallel biomarker staining. However, to overcome the limitation imposed by the maximum number of probes that can be unambiguously distinguished and further enhance the multiplexing capability of QD-based or FL-based molecular profiling, multiple QD or fluorophore staining cycles can be implemented. Specimen de-staining by low-pH treatment, heat degradation, and washing with alcohol and detergents utilized in previous studies often causes specimen degradation. Therefore, DNA link displacement via hybridization with a longer oligonucleotide can provide faster de-staining under non-degrading conditions, as it can efficiently proceed at room temperature in standard neutral buffers. Moreover, as antibody-antigen bond is not broken with this approach (in contrast to other methods), time-consuming re-detection of biomarkers on each cycle is unnecessary.

Figure 11:
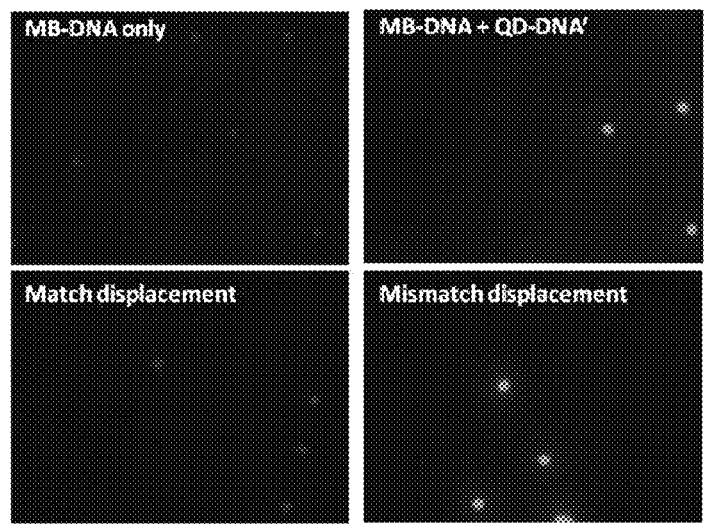
FIG. 11 shows specimen de-staining according to an embodiment of the method. MB-Str (top left) were decorated with ssDNA, which was labeled with complementary QD probes (top right). Incubation with matching displacement probe yielded complete de-staining (bottom left), while mismatch probe had no effect (bottom right).

To test whether QD-DNA probe can be displaced with a longer oligonucleotide, the inventors constructed a model system consisting of streptavidin-coated magnetic beads (MB-Str), to which biotinylated ssDNA was bound. MB-DNA particles were then labeled with complementary QD-DNA probes. While magnetic beads did not show any endogenous fluorescence, QD labeling turned MBs bright red (FIG. 11, top row). Brief incubation with matching displacement probe eliminated QD signal nearly completely, whereas mismatch probe had no effect on MB-QD complex (FIG. 11, bottom row). This shows that de-staining with DNA link displacement works well in the model system and can be used on fixed cells.

Figure 12:
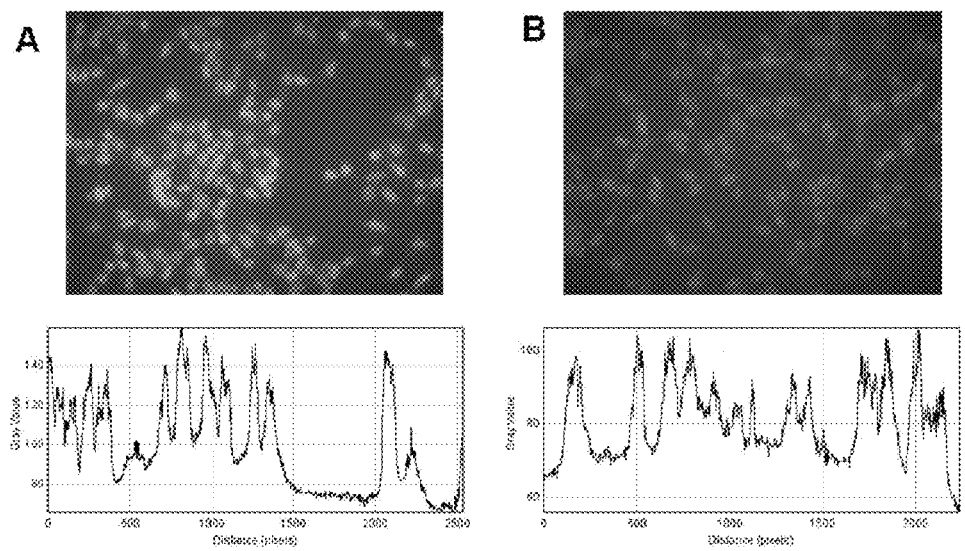
FIGS. 12A and 12B show QD-based staining and de-staining on fixed cells.
Figure 13:
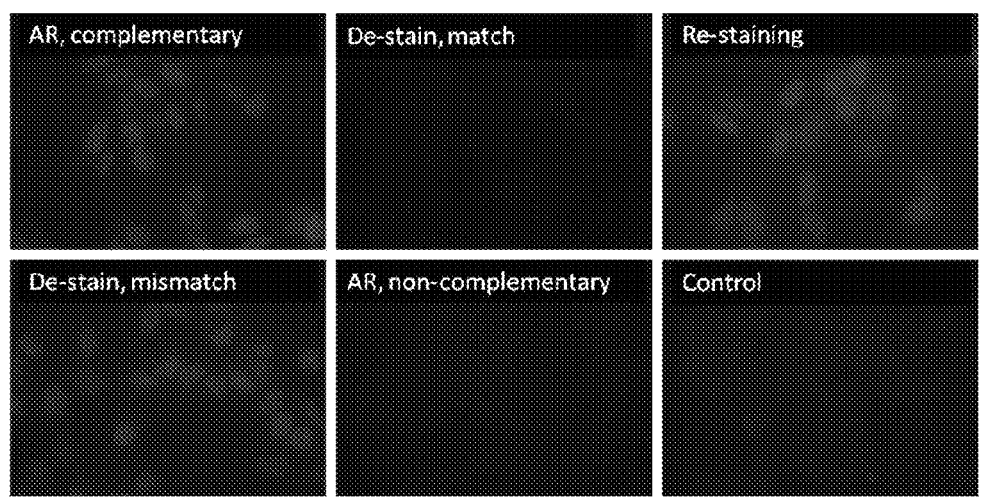
FIG. 13 shows AR staining and de-staining with dye-labeled ssDNA probes. Only complementary probe produced staining, whereas matching displacement probe yielded complete de-staining. Notably, re-staining of AR could be achieved during the second cycle, indicating that Ab/SpA-DNA probes remained intact throughout staining/de-staining procedure.

De-staining of fixed cells proved to be more challenging, as a number of additional interactions could influence dissociation of QD-DNA probe and access to the DNA link for displacement probe could be sterically hindered. Still, the inventors were able to achieve up to 80% reduction in staining intensity during de-staining (FIG. 12). This is in contrast to the quick, specific, and complete de-staining achieved with ssDNA probes labeled with Alexa Fluor dye (FIG. 13). Notably, complete re-staining was also achieved, indicating that Ab/SpA-DNA tag remained intact throughout 2 staining cycles. The data demonstrates the feasibility of using cyclic staining with QD-DNA and dye-labeled DNA probes via DNA link displacement.

Improvements in such method can be achieved by further optimization of QD surface coating and staining conditions to minimize potential non-specific interactions between cells and QDs. While zwitterionic and PEG-coated QDs do not show significant non-specific staining, prolonged residence near cell surface due to formation of DNA link might promote binding to cell components. Further, steric access to the DNA linker for displacement can also be improved. For example, DNA tags can be placed on longer PEG spacers and the length of displacement handle can be increased to promote hybridization of displacement oligonucleotide. Finally, residual non-specifically bound QDs can also be quenched. To avoid dissociation of Ab-DNA from biomarkers, DNA-tagged specimen can be cross-linked with BS3, thus converting cells into stable spatially-encoded DNA arrays.

The highly flexible hybrid IF/FISH 2-step staining platform described herein permits optimization for application-specific criteria due to availability of a number of strategies for preparation of Ab-DNA and QD-DNA probes. Among these, covalent modifications are suitable for preparation of large quantities of probe stocks that can be routinely used for established molecular profiling studies. At the same time, more flexible non-covalent probe self-assembly offers on-demand synthesis of custom probes for validation tests and small studies. Regardless of the probe preparation method, multiplexed parallel staining is readily achievable, thus providing a powerful and yet simple tool for molecular profiling of fixed cells and tissue specimens.

Utilization of unique DNA sequences for linking 1'Ab with fluorescent probe permits further sequence-specific signal amplification via successive deposition of another layer of FL probes. In most one of the most straightforward implementations with QD-based probes, second staining with QD-DNA probes complementary to first layer of QD-DNA can be performed. Since each QD carries multiple oligonucleotides, original Ab-DNA sequences linked with QD-DNA will be converted into a yet larger number of DNA tags present on QDs. Detection of those tags with same-color QDs can provide a signal amplification mechanism. As second layer of staining is also driven by specific DNA hybridization, it is completely compatible with multiplexed staining modalities. In another implementation with organic dye-labeled ssDNA probes, additional amplifier molecule carrying a high number of scarcely distributed DNA tags is added during the second step, thus converting single Ab-DNA into a large DNA array, labeling of which during the $3^{rd}$ step should yield much enhanced signal. We have implemented this approach, for example, on the basis of SpA for labeling of each biomarker with multiple dye molecules, thus achieving good signal-to-noise ratio of staining.

Additionally, ability to significantly expand multiplexing capability of hybrid IF/FISH method with incorporation of cyclic staining approach has been demonstrated. Complete or nearly complete specimen de-staining can be achieved solely by introduction of displacement DNA probes under physiological conditions, thus preserving specimen antigenicity and permitting reliable cyclic staining. This technique can be especially powerful with utilization of flow-chambers for semi-automated cyclic staining and real-time monitoring of staining and de-staining. We have already tested the performance of glass-bottom channel slides and flow-chambers for cell staining with QDs and cyclic staining with dye-labeled ssDNA probes and demonstrated feasibility of real-time staining monitoring.

Comprehensive molecular diagnostics and targeted therapy are essential for making progress towards combating such complex diseases as cancer, immune system disorders, and neurological disorders. Incorporation of novel QD-based tools will undoubtedly play a major role in this process. Unique photo-physical properties and versatile bio-functionalization capabilities make QDs well suited for sensitive quantitative molecular profiling of cells and tissue specimens. Unfortunately, current limitations imposed by either multi-step staining modalities or complex QD-antibody bioconjugation procedures hamper wide adaptation of QD technology for fundamental research and clinical diagnostics. The highly multiplexed staining method described here overcomes such limitations by providing straightforward routes for unique matching of biomarkers and QD probes, thus opening access to single-cell molecular profiling within the context of preserved tissue or cell culture morphology.

Example 2

Quantum-Dot Based Cyclic Multiplexed Staining for Comprehensive Molecular Profiling of Individual Cells and Cellular Populations In-depth understanding of the nature of cell physiology and ability to diagnose and control the progression of pathological processes heavily rely on untangling the complexity of intracellular molecular mechanisms and pathways. To achieve this goal, comprehensive molecular profiling of individual cells within the context of their natural tissue or cell culture microenvironment is required. Neither widely used conventional techniques nor more advanced nanoparticle-based methods have been able to address this task up to date. We have developed a highly multiplexed imaging method, potentially capable of creating single-cell molecular profiles consisting of over 100 biomarkers, and engineered complementary universal quantum dot-based platforms for quick and easy preparation of an extensive library of biomarker-specific fluorescent probes. As our method consists of simple steps requiring no advanced technical skills, it can be directly applied for a wide range of molecular profiling studies, enabling direct analysis of low-abundance events, heterogeneity within cell populations, and interplay between different molecular pathways on a single-cell level.

Conventional biomedical techniques suffer from a limitation in the number of biomarkers that can be analyzed simultaneously (e.g. immunohistochemistry, or IHC), provide limited single-cell information resulting from the need to analyze signals averaged over many cells (e.g. gene chips, protein chips, biomolecular mass spectrometry, etc.), and often utilize qualitative rather than quantitative analysis. Consequently, fundamental understanding of pathological processes as well as clinical diagnostics are limited by the lack of knowledge about the predictive biomarkers that would unambiguously discriminate between disease and normal function, distinguish different disease types, and provide information about possible progression of the pathological process.

Realizing the importance of examining biomarker expression patterns within the context of preserved specimen morphology, a variety of multiplexed imaging techniques have been proposed. Building upon conventional IHC (a mostly single-biomarker imaging method), parallel and sequential staining techniques have been utilized to determine not only expression levels of multiple biomarkers, but also their distribution within individual cells or tissues. See, for example, Englert, C. R., Baibakov, G. V. & Emmert-Buck, M. R. Layered expression scanning: rapid molecular profiling of tumor samples. *Cancer Res* 60, 1526-1530 (2000); Furuya, T. et al. A novel technology allowing immunohistochemical staining of a tissue section with 50 different antibodies in a single experiment. *J Histochem Cytochem* 52, 205-210 (2004); Pirici, D. et al. Antibody elution method for multiple immunohistochemistry on primary antibodies raised in the same species and of the same subtype. *J Histochem Cytochem* 57, 567575 (2009); Toth, Z. E. & Mezey, E. Simultaneous visualization of multiple antigens with tyramide signal amplification using antibodies from the same species. *J Histochem Cytochem* 55, 545-554 (2007); Glass, G., Papin, J. A. & Mandell, J. W. SIMPLE: a sequential immunoperoxidase labeling and erasing method. *J Histochem Cytochem* 57, 899-905 (2009); Wahlby, C., Erlandsson, F., Bengtsson, E. & Zetterberg, A. Sequential immunofluorescence staining and image analysis for detection of large numbers of antigens in individual cell nuclei. *Cytometry* 47, 32-41 (2002); Micheva K D, Busse B, Weiler N C, O'Rourke N, Smith S J: Single-synapse analysis of a diverse synapse population: proteomic imaging methods and markers. *Neuron* 2010, 68:639-653; and Schubert W, Bonnekoh B, Pommel A J, Philipsen L, Bockelmann R, Malykh Y, Gollnick H, Friedenberger M, Bode M, Dress A W M: Analyzing proteome topology and function by automated multidimensional fluorescence microscopy. *Nat Biotechnol* 2006, 24:1270-1278. However, while being highly laborious and time-consuming, these methods still hold a limited multiplexing capability. Recently developed imaging with Raman probes offers more flexibility in obtaining multiplexed data (Liu, Z. et al. Multiplexed Five-Color Molecular Imaging of Cancer Cells and Tumor Tissues with Carbon Nanotube Raman Tags in the Near-Infrared. *Nano Research* 3, 222-233 (2010) and Zavaleta, C. L. et al. Multiplexed imaging of surface enhanced Raman scattering nanotags in living mice using noninvasive Raman spectroscopy. *Proc Natl Acad Sci USA* 106, 13511-13516 (2009)); yet, the large size often significantly hampers probe diffusion within the cross-linked cells and tissues, compromising detection of biomarkers located deep within the specimen. Imaging mass spectrometry offers the greatest multiplexing capability and has a potential for quantitative analysis (Schwamborn, K. & Caprioli, R. M. Molecular imaging by mass spectrometry—looking beyond classical histology. *Nat Rev Cancer* 10, 639-646 (2010) and Wollscheid, B. et al. Mass-spectrometric identification and relative quantification of N-linked cell surface glycoproteins. *Nat Biotechnol* 27, 378-386 (2009)), but it comes at a price of low lateral resolution, high equipment costs, and requirement of correlating obtained biomolecule composition data with optical imaging.

Fluorescent probes based on semiconductor nanoparticles (quantum dots, or QDs) offer advantages for multiplexing over chemical fluorophore probes. Having size of only 2 to 10 nm in diameter, QDs possess unique photo-physical properties, such as size-tunable and spectrally narrow light emission, simultaneous excitation of multiple colors, improved brightness, resistance to photobleaching, and large Stokes shift. Due to these properties, simultaneous parallel detection of up to 10 spectrally distinct QD probes is possible. However, utilization of such multiplexing capability has been hampered by the inability to uniquely match each QD probe with the corresponding biomarker.

To fully utilize extensive multiplexing potential of QD fluorescent tags and exploit wide selection of validated primary antibodies for molecular profiling with IF, the inventors have developed a universal QD/adaptor protein platform for flexible and fast preparation of a library of functional QD-Ab probes. These probes have been used in a multi-cycle 1-step staining procedure described herein below. In a method described herein, QD-Ab probes are prepared prior to staining in a straightforward 1-step procedure via self-assembly between universal QD/adaptor protein platform and virtually any Ab of choice, thus requiring no chemical modification of antibodies and eliminating the need for costly and time-consuming QD-Ab probe purification. Direct 1-step parallel multiplexed staining performed with such probes can utilize a full range of spectrally distinguishable probes without Ab species or buffer composition limitations. Furthermore, multiplexing capability is dramatically expanded by performing staining/imaging/de-staining procedure on the same specimen in several cycles. Capability of the QD-Ab probe to disassemble under low-pH conditions enables complete removal of the QD signal after imaging, thus restoring the specimen to its original state and keeping it unperturbed for the next round of staining. The inventors have used this new multiplexed imaging technique for molecular profiling of fixed cancer cells, showing that at least 50 biomarkers can be reliably imaged at sub-cellular resolution, with potential of expanding this method to imaging of over 100 biomarkers.

Materials and Methods

Synthesis of QD/SpA Probes:

Amine-functionalized PEG-coated QDs (Qdot ITK amino (PEG) quantum dots, Invitrogen) with emission peaks centered at 525, 545, 565, 585, and 605 nm were used for preparation of universal fluorescent probes. First, QDs were activated with bi-functional cross-linker BS3 (Bis[sulfosuccinimidyl] suberate, Thermo Scientific), followed by covalent conjugation with SpA (Protein A from *Staphylococcus aureus*, Sigma-Aldrich). 100 uL 1 uM QD solution in PBS was mixed with 500-1000 molar excess of BS3 and incubated for 30 minutes at RT. Free cross-linker was removed by passing QD/BS3 mixture through a NAP-5 column (GE Healthcare) pre-equilibrated with PBS. Handheld UV lamp was used to aid in collection of QD-containing elution fraction. Eluted QDs were concentrated down to 70 uL with a 100 KDa MWCO concentrator (GE Healthcare), and 30 uL of 100 uM SpA solution in PBS was added. Reaction was incubated overnight at room temperature, quenched for 30 minutes with ethanolamine (Sigma-Aldrich), and purified by ultrafiltration for at least 7 times with a 100 KDa MWCO concentrator. Purified QD-SpA probes were stored in PBS solution at 4° C.

Cell Culture and Processing:

Human prostate cancer cell line LNCaP (ATCC) was used as a model for optimization of a multiplexed IF protocol. Cells were grown in glass-bottom 24-well plates (Greiner Bio-One) for 2-3 days to a density of ~60%. Humidified atmosphere at 37° C. with 5% $CO_2$ was maintained. RPMI-1640 culture medium with L-Glutamine and 25 mM HEPES (Lonza) supplemented with 10% Fetal Bovine Serum (PAA Laboratories) and antibiotics (60 µg/mL streptomycin and 60 U/mL penicillin) was used. For IF staining procedure, cells were fixed with formaldehyde and permeabilized with detergents. First, cells were washed twice with pre-warmed TBS (1 mL per well). Solution was added carefully to the wall of each well to avoid cell detachment from the glass coverslip. Next, 400 uL of 4% formaldehyde in TBS (prepared from methanol-free 16% stock, Thermo Scientific) was added to each well, incubated for 20 min at room temperature, and rinsed with TBS. Finally, cells were permeabilized with 2% DTAC/TBS (Dodecyltrimethylammonium chloride, Sigma-Aldrich) for 20 min and 0.25% TritonX-100/TBS (prepared from 10% stock, Thermo Scientific) for 5 min and washed 5 times with TBS. Fixed cells were stored in TBS at 4° C.

Imaging:

An IX-71 inverted fluorescence microscope (Olympus) equipped with true-color camera (QColor S, Olympus) and spectral imaging camera (Nuance, CRI) was used for cell imaging. Low-magnification images were obtained with 10× and 20× dry objectives (NA 0.40 and 0.75 respectively, Olympus) and high-magnification with 100× oil-immersion objective (NA 1.40, Olympus). Wide UV filter cube (330-385 nm band-pass excitation, 420 nm long-pass emission, Olympus) was used for imaging of all QD probes, while Rhodamine LP cube (530-560 nm band-pass excitation, 572 nm long-pass emission, Chroma) was used for Alexa Fluor 568 detection. All images were acquired with cells attached to the coverslip bottom of the well and immersed in TBS. No anti-fading reagents were used. For parallel multiplexed staining, images were obtained with the spectral imaging camera scanning through the full 420-720 nm spectral range. NUANCE™ image analysis software was used to unmix obtained images based on the reference spectra of each QD component along with an extra channel for background fluorescence. In a false-color composite image, brightness and contrast of each channel was adjusted for best visual representation and clear depiction of relative biomarker distribution. For sequential staining a permanent reference point was marked on the bottom of the well to aid in finding the same cell subset for each imaging cycle. Minor misalignment between different frames was adjusted manually, and frames were merged into a false-color composite image in Photoshop (Adobe Systems). Each frame was imaged using the same parameters for direct comparison of signal intensity and biomarker expression levels. However, for false-color composite image, brightness and contrast of each frame was again adjusted to achieve the best clarity in relative biomarker distribution.

2-Step Single-Color Immunofluorescence:

Polyclonal rabbit antibodies raised against AR, MAOA, pAkt, and P-tubulin were purchased from Santa Cruz Biotechnology. Monoclonal mouse anti-HSP90 Ab was from Thermo Scientific. All buffers were prepared with deionized water (>18 MO-cm). Blocking buffer composition was 2% BSA (from Bovine Serum Albumin powder, Sigma-Aldrich), 0.1% casein (from 5% solution, Novagen), and 1×TBS (from 10× solution, Fisher Scientific). Staining buffer composition was 6% BSA in 1×TBS. Staining was performed with either dye-labeled secondary antibodies (rabbit-anti-mouse and goat-anti-rabbit IgG, Sigma-Aldrich, labeled with Alexa Fluor 568 carboxylic acid succinimidyl ester, Invitrogen), QDs functionalized with secondary Ab fragments (Qdot goat F(ab')2 anti-mouse or anti-rabbit IgG conjugates (H+L), Invitrogen), or QD/SpA probes prepared as described above. All staining steps were performed directly inside the wells of glass-bottom 24-well plates at ambient conditions.

For a 2-step 1F, cells were blocked with blocking buffer for 30 minutes and incubated with 3000 µl 1 µg/mL primary antibodies (diluted 1:200 from 0.2 mg/mL stock in staining buffer) for 1 hour. Then, cells were washed 3 times with TBS and incubated with either 3000 µl 4 µg/mL dye-labeled 2'Ab, 4 nM QD-2'Ab, or 10 nM QD/SpA in staining buffer for 1 hour in the dark. Extra fluorescent labels were removed by rinsing cells with 1% BSA/0.1% casein/TBS twice and washing with TBS 3 times. Fluorescence imaging was done immediately following staining, unless stated otherwise.

Multiplexed 1-step Immunofluorescence:

Multiplexed IF studies were performed in parallel, sequential, or combined parallel/sequential manner. Regardless of the staining type, cells were blocked with blocking buffer for 30 minutes as described for 2-step IF. Concurrently, QD-Ab probes were prepared by incubating 5 µl 500 nM QD/SpA with 1.5 µl 0.2 mg/mL primary Ab for 1 hour at room temperature. Each QD-Ab probe was prepared in a separate microcentrifuge tube. For parallel multiplexed staining all probes were combined in a single tube, diluted to 300 µl with staining buffer, and immediately applied to pre-blocked cells. After 1-2 hour staining, cells were rinsed with 1% BSA/0.1% casein/TBS twice and washed with TBS 3 times. Imaging was done immediately following staining. For single-color sequential staining, QD-Ab probes were prepared using the same QD/SpA incubated with different antibodies in separate microcentrifuge tubes. Then each probe was used for a 1-step single-color staining and imaging. Each staining cycle consisted of (i) pre-blocking, (ii) staining, (iii) imaging, and (iv) de-staining. The first three steps were identical to those for parallel staining. De-staining was performed by incubating stained cells in 400 µl pH2 Glycine-HCl buffer with 0.1% casein for 15 minutes. Following de-staining the pH was gradually brought back to neutral by rinsing with pH3, 4, and 5 Glycine-HCl buffers and washing 5 times with TBS. Combined parallel/sequential staining utilized multiple QD-Ab probes and spectral imaging on each cycle.

QD-Ab Probe Cross-Talk and Stability Studies:

Probe cross-talk studies were performed in a same manner as parallel 2-color staining described above, except that one QD/SpA conjugate was incubated with primary Ab, while the other one was not. Following QD-Ab probe assembly, QD1-Ab and $QD_2$/SpA were combined in the same microcentrifuge tube, diluted to 300 µL in staining buffer, and added to pre-blocked cells. After 1-hour staining, cells were washed and imaged. Spectral imaging was used to unmix and quantitatively compare individual QD signals. QD525 and QD565 were used for this study. Intensity of the dimmer QD525 channel was scaled up 4 times compared to brighter QD565 channel to correct for differential brightness of QD probes.

For examination of long-term staining stability with QD-Ab probes, single-color 1-step staining was performed as described above. AR was selected as a target biomarker due to its clearly defined nuclear localization. Permanent reference point was marked on the bottom of the well, and cell subset in the vicinity of reference point was imaged. Stained cells were then left in TBS at 4° C. Images of the same subset of cells were taken at 0, 4, 24, and 48 hours post-staining, keeping camera exposure time and other imaging parameters the same for all time points.

Biomarker Degradation Studies:

To study biomarker degradation (i.e. loss of antigenicity) due to cyclic washing/blocking/de-staining treatment and prolonged exposure to ambient conditions, staining of AR was performed with QD-Ab probes immediately after treating cells with 1 to 10 degradation cycles. Each treatment condition was tested on cells in different wells of the same 24-well plate. Degradation cycle consisted of the following steps: washing cells with TBS for 10 minutes, de-staining at pH2 for 15 minutes, rinsing with pH3,4,5 buffers, washing with TBS, and blocking for 30 minutes with 2% BSA/0.1% casein/TBS. To avoid inconsistency in staining and imaging conditions, all cells were stained and imaged at the same time (as a result, exposure to 1 degradation cycle implied incubation in TBS for 9 cycles, then treatment with degradation conditions, and then staining and imaging). All cells were imaged at low and high magnification using true-color and spectral imaging cameras. Exposure time and other imaging conditions were kept the same for all images taken, thus enabling direct quantitative comparison of signal intensity. NUANCE™ image analysis software was used to identify regions of interest (ROIs) that included nuclear AR staining and excluded background fluorescence. Average signal from multiple ROIs in low-magnification images was recorded.

SPR Analysis of SpA/IgG Bond Stability:

SPR measurements of SpA/IgG bond stability were done on a Biacore T100 instrument (GE Healthcare). SpA or rabbit-anti-mouse IgG were immobilized on CM5 sensor chip via covalent conjugation between primary amines on SpA or IgG and carboxylic acid groups on the dextran coating of the chip. All studies were done in 150 mM NaCl, 10 mM HEPES pH7.4 buffer under continuous flow at 104/min. Surface regeneration was performed with 10 mM Glycine-HCl pH2 buffer. For binding/dissociation studies SpA was injected over IgG-modified surface and control unmodified surface, whereas IgG was injected over SpA-modified and control surfaces. Interaction between ligand and analyte at high (100 nM) and low (10 nM) analyte concentrations were monitored. For high analyte concentration, binding was monitored for 10 minutes and dissociation for 30 minutes, while for low analyte concentration, times were 30 and 60 minutes respectively. During the dissociation step, the surface was continuously washed with running buffer. The data analysis was carried out using the BlAevaluation 2.0 software.

Results

Molecular profiling of individual cells involves detection and quantification of multiple relevant biomarkers, which in principle can be achieved with IF imaging by tagging each biomarker with unique fluorescent probe and detecting its localization with high sensitivity at sub-cellular resolution. Utilization of QD probes featuring narrow symmetrical emission profiles permits simultaneous detection of up to 10 different probes within the visible spectral range. However, multiplexing capacity of QD-based IF can be further expanded to over 100 biomarkers by performing multiple staining/imaging cycles on the same specimen. In order to achieve this: (i) each QD probe should be uniquely matched to corresponding biomarker, exhibiting no cross-talk between different probes in a staining cocktail; (ii) QD signal should be completely removed after imaging, providing no interference with the next staining cycle; (iii) biomarker antigenicity and specimen integrity should be retained throughout multiple staining/imaging/de-staining cycles. Practical considerations associated with these conditions should also be addressed. In particular, molecular profiling requires preparation of a large library of unique QD-Ab probes. Therefore, preparation of such probes should be easy, flexible, and relatively inexpensive.

Figure 14:
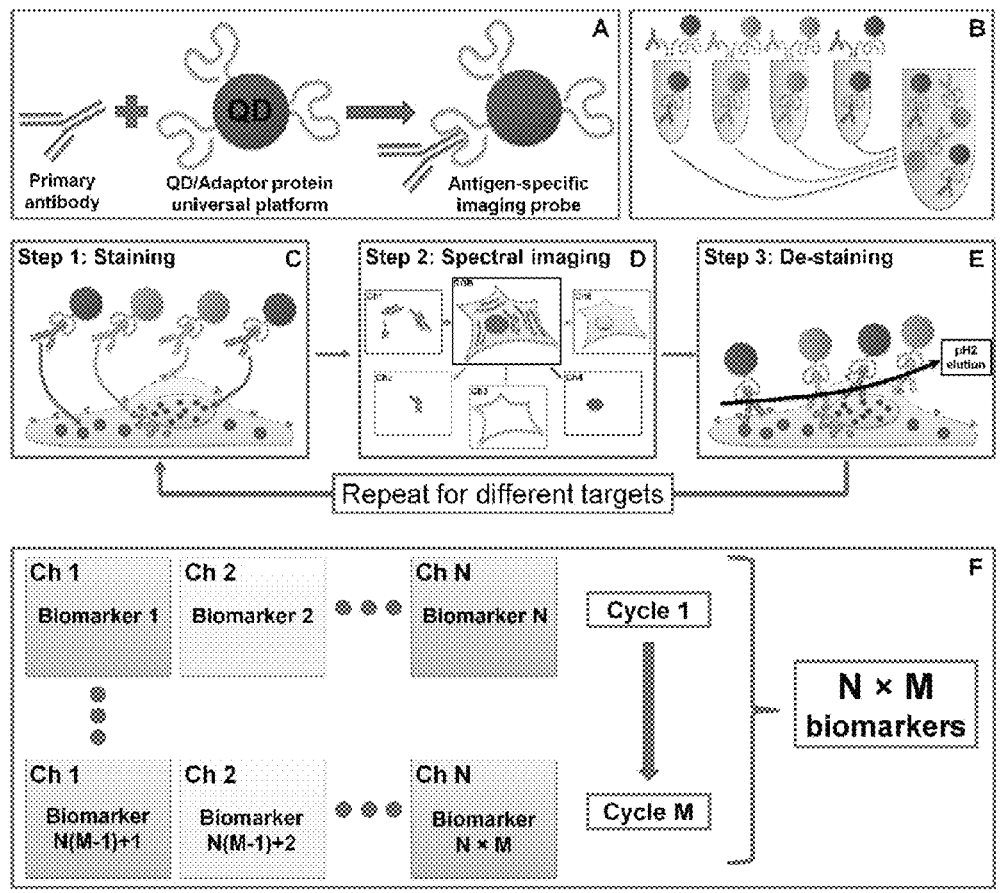
FIGS. 14A-14F shows a schematic representation of an embodiment of the QD-based cyclic multiplexed staining method for comprehensive single-cell molecular profiling.

In a new cyclic multiplexed imaging approach described herein, the inventors addressed these conditions by engineering a universal QD/adaptor protein platform for 1-step, purification-free preparation of QD-Ab probes via self-assembly, utilizing QD-Ab probes for direct biomarker labeling in parallel multiplexed staining, and performing multiple cycles of staining for obtaining a comprehensive molecular profiles of individual cancer cells at sub-cellular resolution. The method can be described as follows. First, universal QD/adaptor protein platform is used to capture intact Ab from solution during a pre-staining step to form a functional QD-Ab fluorescent probe (FIG. 14A). Once formed, all different probes are mixed in a single cocktail (FIG. 14B) and incubated with cells for parallel multiplexed staining (FIG. 14C). Second, following staining, fluorescence microscopy with spectral imaging is utilized to acquire and unmix signal from each QD probe, generate quantitative biomarker expression profiles, and depict relative biomarker distribution (FIG. 14D). Third, complete de-staining of the specimen is done by brief washing with low-pH buffer, permitting the next full cycle of IF staining for a different subset of biomarkers (FIG. 14E). With each staining cycle N biomarkers can be analyzed, where N depends on the number of spectrally distinct fluorescent probes that can be detected simultaneously. Performing IF staining for M sequential cycles generates M subsets of data for the same specimen, thus yielding an overall molecular profile consisting of N×M biomarkers (FIG. 14F). Therefore, the method permits extensive molecular profiling of specimens with preserved morphology at multiplexing levels far exceeding even the most advanced imaging techniques.

Multiplexed Biomarker Imaging:

To demonstrate the utility of the method for molecular profiling, the inventors imaged 4 cancer biomarkers (heat shock protein 90, HSP-90; androgen receptor, AR; monoamine oxidase A, MAOA; and phosphorAKT, pAkt) and a housekeeping biomarker β-tubulinin formalin-fixed prostate cancer cells (LNCaP). Parallel staining of these biomarkers with 5 different QD-Ab probes (FIG. 15, top panel) as well as sequential staining with same-color QD-Ab probes (FIG. 15, bottom panel) yielded consistent molecular profiles with subcellular resolution.

Figure 15:
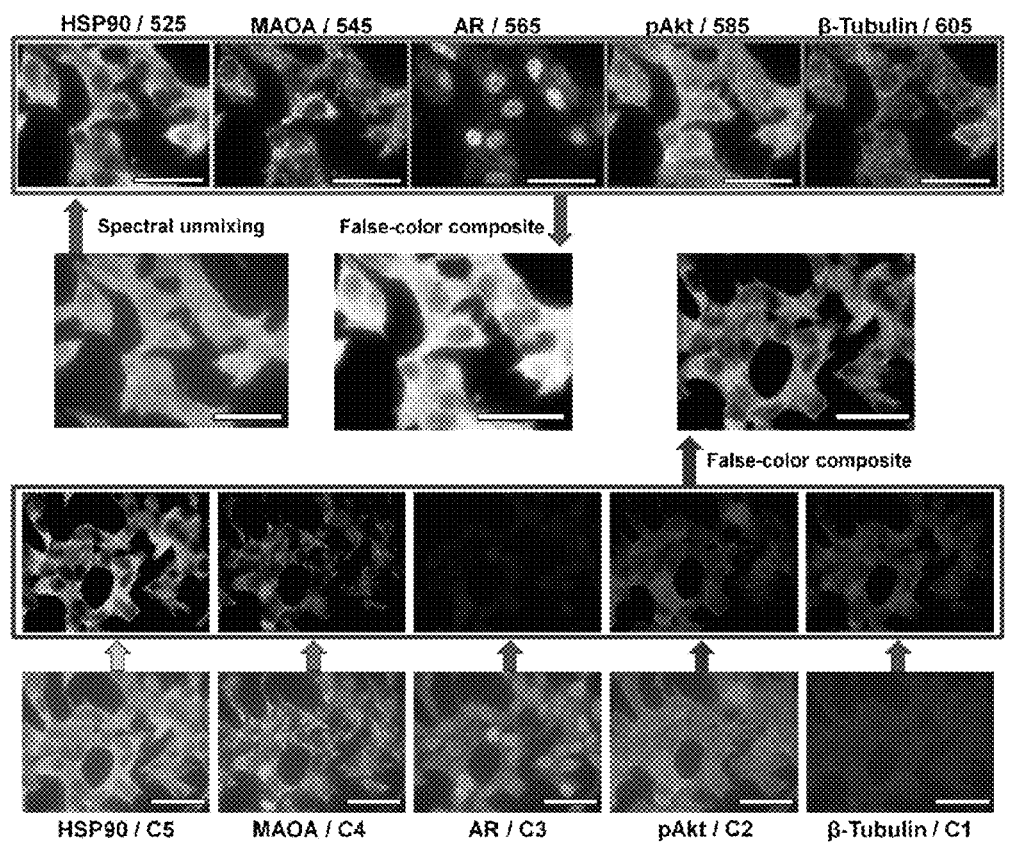
FIG. 15 shows multiplexed staining of 4 cancer biomarkers (HSP90, MAOA, AR, and pAkt) and housekeeping biomarker B-tubulin. Both parallel (top panel) and sequential (bottom panel) staining yielded consistent molecular profiles with sub-cellular resolution. Sequential images were taken on the same cell sub-population with identical imaging parameters, thus allowing direct comparison of biomarker relative expression levels and intracellular distribution. However, intensity of individual channels (for parallel staining) or frames (for sequential staining) was adjusted to achieve clear biomarker representation in false-color images. Scale bar, 50 μm.

For parallel multiplexing, the inventors utilized QDs emitting in a visible spectral range (at 525, 545, 565, 585, and 605 nm). 20 nm separation between emission peaks ensured reliable spectral unmixing of individual QDs, while permitting imaging of multiple probes within a narrow spectral window. QD-Ab probe assembly was done in separate tubes for 1 Hr immediately prior to staining. At the same time, cells were blocked with BSA (bovine serum albumin)/casein blocking buffer to eliminate QD-Ab probe non-specific binding. Parallel multiplexing involved spectral imaging and unmixing of QD signals, which produced most accurate results when all signals were of similar intensity. Therefore, brighter red QD probes were used for less abundant (or more diffusely distributed) biomarkers, while dimmer green QDs were reserved for more abundant (or more densely packed) biomarkers. In a case when differences in biomarker expression could not be compensated by brighter probes, less abundant biomarkers were imaged in a separate cycle. For example, staining intensity of β-tubulin was significantly dimmer compared to cancer biomarkers. Therefore, for parallel imaging this biomarker was labeled with brightest QD605 probes (FIG. 15, top panel). Yet, its contribution to an unmixed image was less reliable, while expression and distribution of B-tubulin was clearly visualized when imaged on a separate cycle (FIG. 15, bottom panel). Nonetheless, spectral imaging provides sufficient flexibility for simultaneous imaging and unmixing of high- and low-abundance biomarkers, and re-staining on a separate cycle can be performed when the quality of low-intensity signal is significantly compromised.

Sequential multiplexing involved imaging of the same area of the specimen and matching biomarker distribution patterns obtained at different imaging cycles. This was particularly challenging to achieve when high-magnification imaging was performed. To aid in finding the same subset of cell for each imaging cycle, the inventors placed a reference mark on the bottom of each well and stepped a set distance from the mark for imaging. Minor mismatch in frame alignment was manually corrected with image-processing software. After alignment each frame was false-colored, and all frames were overlaid to yield a composite 5-color image for the study of relative biomarker distribution. It should be noted, that sequential imaging provided direct quantitative comparison of biomarker expression levels, as identical QD probes and imaging conditions were used for all biomarkers. In contrast, quantitative analysis of spectrally unmixed parallel staining was not as straightforward as each QD probe exhibited different relative brightness (due to differences in absorption cross-section, quantum yield, and camera sensitivity to different wavelengths of light). Therefore, signal intensity of each QD channel in composite image should be scaled appropriately when quantitative analysis is necessary.

QD-Ab Probe Preparation:

Multiplexed IF necessarily requires preparation of a large library of QD-labeled antibodies. Common 2-step staining procedure utilizes QD-labeled secondary antibodies for detection of intact primary antibodies. However, multiplexing capability of this approach is limited by the number of suitable primary/secondary antibody combinations. To overcome this limitation, several direct covalent and non-covalent QD-Ab conjugation methods have been developed, yet all methods suffer from serious limitations that hamper wide use of QD-based multiplexed imaging techniques for biomedical research and clinical diagnostics. For example, covalent QD-Ab conjugation yields stable and unique fluorescent probes, though chemical modification of antibodies is not only highly complex and prohibitively expensive, but also often results in reduction in antibody affinity and/or specificity. Widely used streptavidin-biotin pairing creates a strong link in a straightforward procedure, but it requires the preparation of biotinilated antibodies and often leads to cross-linking of QD/Streptavidin due to binding to multiple biotins on a single Ab. Functionalization of QDs with intact antibodies can be achieved via self-assembly with adaptor protein. Yet, preparation of QD/adaptor protein nanoparticles was done either via strong electrostatic interactions (Goldman, E. R. et al. Conjugation of luminescent quantum dots with antibodies using an engineered adaptor protein to provide new reagents for fluoroimmunoassays. *Anal Chem* 74, 841-847 (2002); Goldman, E. R. et al. Avidin: a natural bridge for quantum dot-antibody conjugates. *J Am Chem Soc* 124, 6378-6382 (2002); and Jaiswal, J. K., Mattoussi, H., Mauro, J. M. & Simon, S. M. Long-term multiple color imaging of live cells using quantum dot bioconjugates. *Nat Biotechnol* 21, 47-51 (2003)), HIS-tag-mediated binding (Lim, Y. T., Cho, M. Y., Lee, J. M., Chung, S. J. & Chung, B. H. Simultaneous intracellular delivery of targeting antibodies and functional nanoparticles with engineered protein G system. *Biomaterials* 30, 1197-1204 (2009)), or covalent conjugation to carboxylic acid groups on the QD surface (Jin, T. et al. Antibody-protein A conjugated quantum dots for multiplexed imaging of surface receptors in living cells. *Mol Biosyst* 6, 2325-2331 (2010)), all of which utilized negatively-charged QDs that often exhibit extremely high non-specific binding to fixed cells and tissue specimens. Therefore, such probes were successfully used for immunoassays and live-cell imaging, but not for multiplexed IF. Moreover, potential for Ab exchange between QDs and probe cross-talk due to relatively low stability of non-covalent interactions have not been carefully evaluated. Despite these concerns, we regarded adaptor protein as the most flexible and promising linker for engineering of universal QD-based imaging probes for multiplexed IF applications.

Shielding of the QD core with PEG shell and neutralization of the QD charge are critical for eliminating non-specific staining during IF. Therefore, as a platform for our method we used highly stable, bright, and water-soluble PEG-coated QDs. With proper specimen blocking, those particles produced no detectable non-specific staining. It should be noted that strong non-specific QD binding represents a serious and persistent problem for QD-based staining of fixed cells and tissue specimens, often hampering utilization of QD probes for IF applications. In our experience careful shielding of the QD core by poly(ethylene glycol) (PEG) shell or complete neutralization of the QD surface charge by functionalization with zwitterionic groups efficiently eliminated non-specific interactions (Zrazhevskiy, P., Sena, M. & Gao, X. H. Designing multifunctional quantum dots for bioimaging, detection, and drug delivery. *Chemical Society Reviews* 39, 4326-4354 (2010)). As it is hard to achieve precise control over the QD surface properties, variations in composition of different PEG-coated QD lots led to variations in non-specific staining observed with those probes. To compensate for this effect, in addition to commonly used BSA the inventors included 0.1% casein in a blocking step. While not wishing to be bound by a theory, being more negatively charged and hydrophobic than BSA, casein serves as a more stable blocking reagent for QDs, which also carry a net negative charge. However, since use of higher casein content during the blocking step or incorporation of casein in staining buffer often resulted in decreased staining intensity, utilization of this blocking reagent was kept to a minimum.

At the same time, the PEG shell featured primary amine groups for covalent conjugation with adaptor protein. A wide range of native and engineered adaptor proteins capable of binding intact antibodies is available. The inventors chose the most widely used and well-characterized adaptor protein— Protein A from *Staphylococcus aureus* (SpA)—for demonstration of multiplexed imaging technology, while other adaptor proteins (e.g. Protein G, Protein A/G, etc.) can also be used in a similar fashion. In some embodiments, the number of sterically accessible binding points between adaptor protein and Ab can be limited to one, as to prevent cross-linking of different QD/SpA probes via single Ab. In this regard, SpA possesses five IgG binding sites (Moks, T. et al. Staphylococcal protein A consists of five IgG-binding domains. *Eur. J Biochem* 156, 637-643 (1986)), two of which are accessible simultaneously, while IgG has two SpA binding sites on its Fc region. In solution, formation of polymeric SpA/IgG complexes is possible (Mota, G., Ghetie, V. & Sjoquist, J. Characterization of the soluble complex formed by reacting rabbit IgG with protein A of *S. aureus*. *Immunochemistry* 15, 639-642 (1978)). However, when SpA/IgG is located on the QD surface, binding of additional SpA molecules is likely to be sterically hindered, thus eliminating the possibility of QD cross-linking.

Sufficiently high excess of cross-linker was added to prevent cross-linking of primary amines on different QDs or on the surface of the same QD. Extra cross-linker was removed with a NAP-5 desalting column. Since purification with the desalting column led to significant dilution of the QD sample, activated QDs were concentrated to 1 µM and allowed to react with SpA at ambient conditions overnight. While the reaction could be performed at lower QD concentrations (e.g. 100-200 nM), the conjugation yield was noticeably higher when at least 1 µM QD solution was used (especially for lower-quality QD lots). Vortexing or other mechanical agitation was avoided on all steps, as it led to QD aggregation. Finally, QD/SpA conjugates were purified from excess SpA by repeated ultrafiltration in 100 kDa MWCO concentrators. Six-seven rounds of ultrafiltration (with 10× sample dilution each) completely eliminated SpA (as tested with Alexa Fluor 647-labeled SpA, data not shown).

Figure 16:
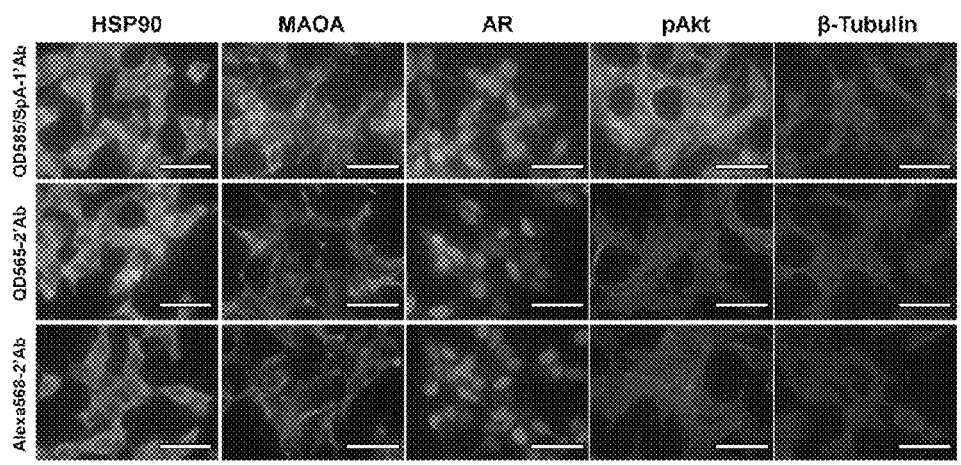
FIG. 16 shows comparison of QD/SpA-1'Ab staining with conventional IF. For all 5 biomarkers, individual staining patterns and relative expression levels detected with QD/SpA-1'Ab probes in a 1-step staining procedure (top row) were consistent with those obtained with either QD-2'Ab probes (middle row) or Alexa Fluor568-labeled 2'Ab (bottom row) in a 2-step staining, confirming robustness and specificity of QD/SpA-Ab probes. Scale bar, 50 μm.

Performance of QD/SpA-Ab probes was assessed by staining 5 different biomarkers individually (FIG. 16, top row) and comparing the relative staining intensity and biomarker distribution patterns with those obtained with conventional 2-step 1F using QD-2'Ab (FIG. 6, middle row) or Alexa Fluor 568-labeled 2'Ab (FIG. 16, bottom row). As expected, overall signal intensity obtained with QD/SpA-Ab probes was lower than that of QD-2'Ab due to the absence of amplification mechanism in 1-step staining. Therefore, 1-step staining procedure was most suitable for characterization of high-abundance biomarkers, while staining of low-abundance biomarkers (e.g. β-tubulin) was less reliable. Nonetheless, staining patterns and relative biomarker expression were consistent throughout all three procedures, indicating preserved specificity and affinity of antibodies in a QD/SpA-Ab complex. No aggregation of QD probes was observed throughout pre-staining and staining steps, confirming that binding of more than one QD/SpA per Ab was sterically hindered.

Figure 17:
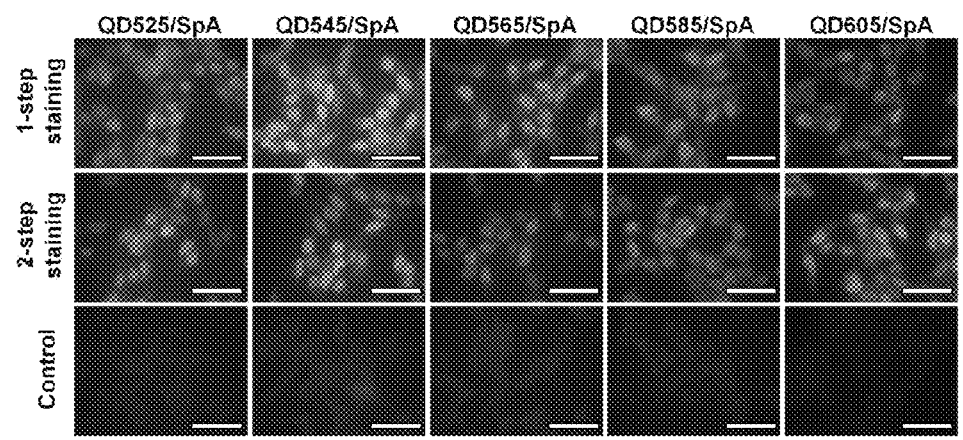
FIG. 17 shows AR staining with QD/SpA-Ab probes. Androgen receptor was stained with 5 different QD/SpA probes in either 1-step (top row) or 2-step (middle row) staining procedure. Both procedures revealed characteristic nuclear localization of this biomarker and yielded similar staining intensity, confirming QD/SpA-Ab binding exclusively via SpA-Ab bond. At the same time, no significant non-specific staining with non-functionalized QD/SpA probes was observed (bottom row). Scale bar, 50 μm.

According to the method design, all QD-Ab probes were formed via non-covalent binding between SpA and Ab. However, direct QD-Ab self-assembly via other routes (e.g. electrostatic or hydrophobic interactions) could be possible. To confirm that assembly happened indeed due to SpA-Ab binding, we performed several control staining experiments. First, all 5 different QD/SpA probes were used in 1-step staining of androgen receptor, showing consistent predominantly nuclear localization of this biomarker (FIG. 17, top row) and indicating that QD-Ab complex successfully formed. Second, 2-step AR staining was done. On the first step cells were incubated with 1'Ab, then excess Ab was washed away, and cells were stained with QD/SpA probes. Consistent nuclear staining with similar signal intensity was obtained in this case as well (FIG. 17, middle row), confirming that QD/SpA probes successfully recognized target-bound antibodies inside cells. Finally, control staining with QD/SpA probes alone showed only minimal diffuse non-specific binding (FIG. 17, bottom row). Same 1-step and 2-step staining experiments performed with non-modified PEG-coated QDs produced only minimal non-specific staining and failed to bind to Ab in either procedure (data not shown). Therefore, we confirmed with certainty that QD-Ab complex formation was mediated exclusively by SpA-Ab binding. Moreover, QD/SpA exhibited high specificity in Ab binding, showing no enhanced off-target binding beyond that observed for unmodified PEG-coated QDs.

QD-Ab Probe Stability and Cross-Talk:

Assembly of the QD/SpA-Ab probe was done in a microcentrifuge tube by simple mixing of QD/SpA and 1'Ab raised against a biomarker of interest. SpA binds a wide range of antibodies with a reasonably high affinity (Kd on the order of $10^{-8}$ M). Therefore, by adding QD/SpA in a slight excess to antibodies and performing incubation in concentrated solution prior to staining, complete capture of antibodies by QD/SpA can be achieved, thus, uniquely matching each QD-biomarker pair and preventing binding of free IgG to vacant SpA sites on different QD/SpA probes. However, considering that all QD-Ab probes were formed via the same non-selective and non-covalent SpA-Ab bond, we were concerned that spontaneous QD-Ab dissociation, Ab exchange, and cross-talk between different probes could occur. In fact, probability of such cross-talk could be high if free antibodies were present in solution, as we observed that QD/SpA could bind Ab and produce nearly identical staining even when mixed in dilute concentrations and immediately applied to cells. To address this concern the inventors monitored SpA-Ab dissociation kinetics using SPR (surface plasmon resonance) measurements on a Biacore T100 instrument and assessed QD-Ab probe stability and potential for cross-talk experimentally with cell staining.

Figure 18A:
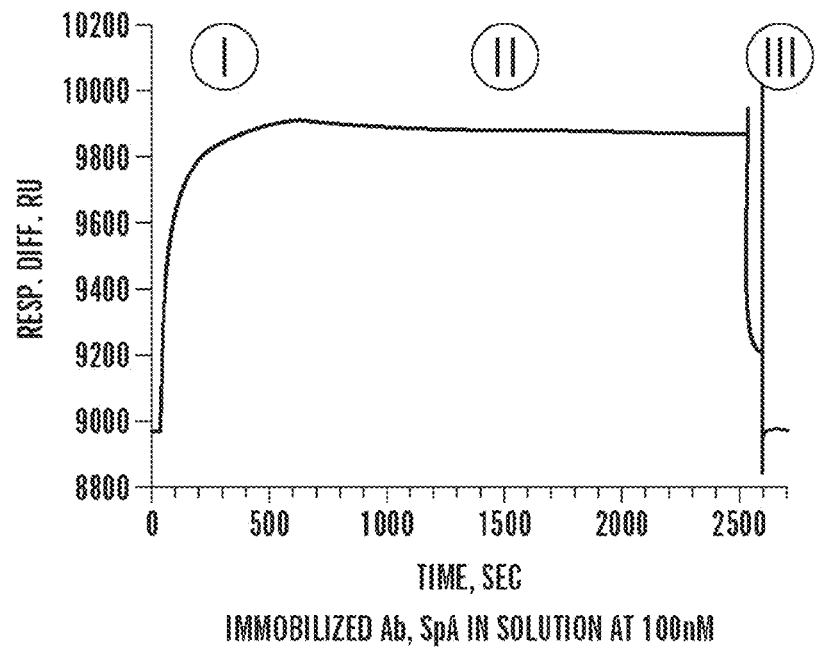
FIGS. 18A-18C shows SPR analysis of SpA-Ab bond stability. Either rabbit anti-mouse antibody or SpA was immobilized on the surface of C5 chip. Then binding and dissociation of free SpA to immobilized Ab (FIG. 8A) or free Ab to immobilized SpA (FIGS. 18B and 18C) were monitored.
Figure 18B:
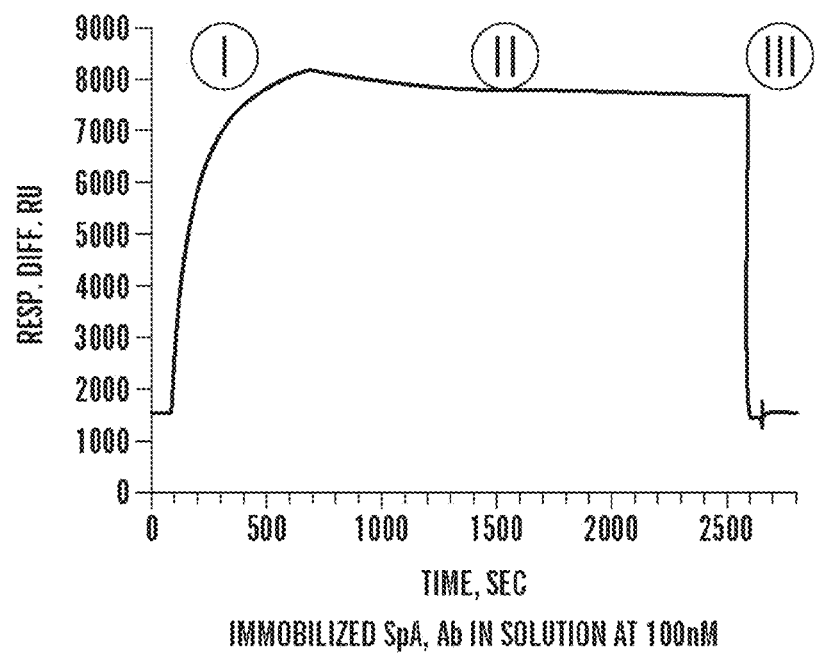
Figure 18C:
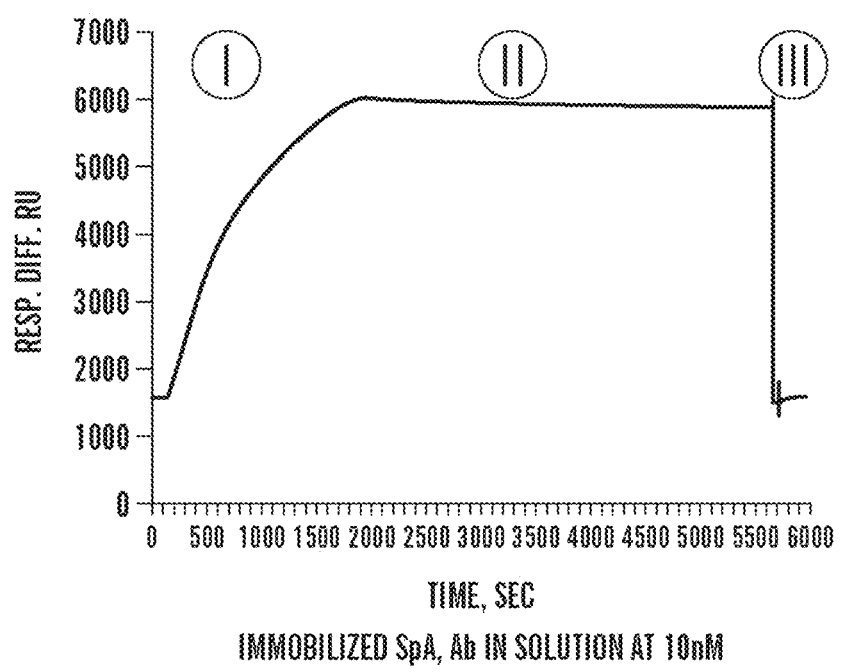

For SPR studies, either SpA or rabbit anti-mouse 2'Ab were immobilized on the dextran-coated surface of C5 chip. Binding of excess 2'Ab to immobilized SpA and excess SpA to immobilized 2'Ab in reference to control unmodified surface was recorded. The invetors observed overall lower binding affinity when analyte was injected at high concentration (250 nM-4 µM) with Kd 5-10 times higher than that for low-concentration analyte (10 nM-250 nM). Measurements of binding/dissociation kinetics showed nonlinear behavior which was especially pronounced for high-concentration analyte. This observation was consistent with previous reports suggesting that slow binding/dissociation by strong binding sites was accompanied with fast binding/dissociation via weak sites, especially when strong sites were saturated (Myhre, E. B. & Kronvall, G. Immunochemical aspects of Fc-mediated binding of human IgG subclasses to group A, C and G streptococci. *Mol Immunol* 17, 1563-1573 (1980)). As a result, dissociation curves (recorded for 30 minutes) for high-concentration analyte (either SpA or 2'Ab at 100 nM) showed an initial fast drop in signal accounting for up to 5% loss of bound analyte, followed by a very slow dissociation (FIGS. 18A and 18B). Same measurements performed with low-concentration analyte (2'Ab at 10 nM, which is consistent with final Ab concentration in staining buffer) showed nearly no SpA-Ab dissociation for 60 minutes, retaining over 97% of bound Ab (FIG. 18C). These results indicated that SpA-Ab dissociation kinetics is sufficiently slow at the concentration range and time-frame of the cell staining procedure to prevent QD-Ab complex disassembly and release of free antibodies in solution.

Figure 19:
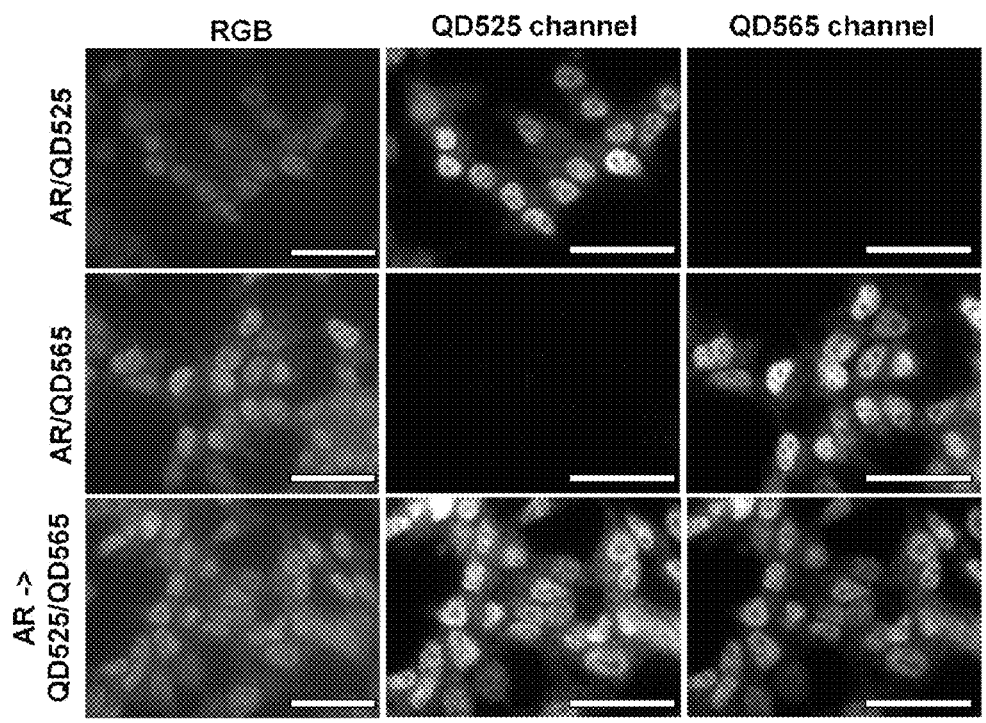
FIG. 19 shows lack of cross-talk between QD/SpA-Ab probes in parallel staining. To determine the possibility of the Ab exchange between probes and examine the extent of cross-talk staining, the inventors pre-assembled anti-AR IgG with either QD525/SpA (top row) or QD565/SpA (middle row). Then the competing QD/SpA probe of opposite color was added, and QD mixtures were incubated with cells. In both cases only pre-assembled probe showed specific nuclear staining, while the competing probe failed to capture Ab and produce any detectable staining. At the same time, when IgG, QD525/SpA, and QD565/SpA were mixed simultaneously and immediately applied to cells, both probes successfully captured Ab and produced AR staining with nearly 50% contribution each (bottom row). Spectral imaging and unmixing was used to extract individual QD signals and remove background. Intensity of QD525 channel was increased 4 times relative to QD565 channel to compensate for differential brightness of QD probes. Scale bar, 50 μm.
Figure 20A:
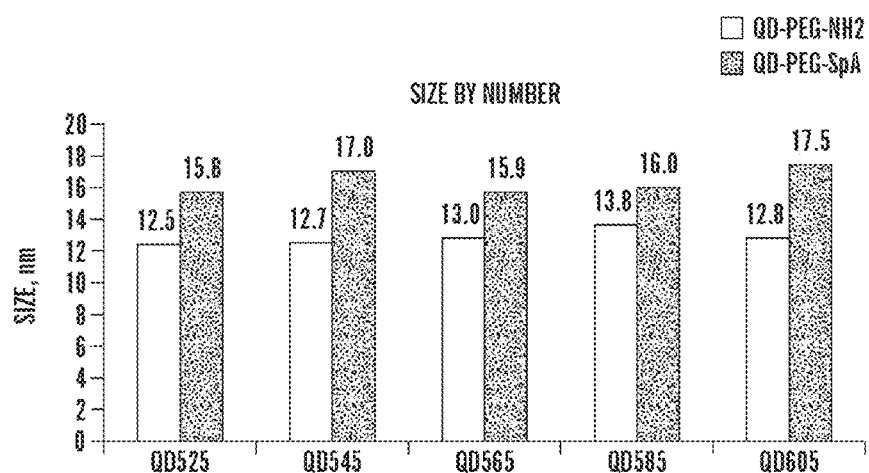
FIG. 20 show consistent size (FIG. 20A) and biomarker staining kinetics (FIG. 20B) with 5 different QD-SpA probes.
FIG. 20C shows consistency of staining kinetics of HSP90 biomarker (HeLa cells) with small (QD525) and large (QD605) QD/SpA/Ab.
Figure 20B:
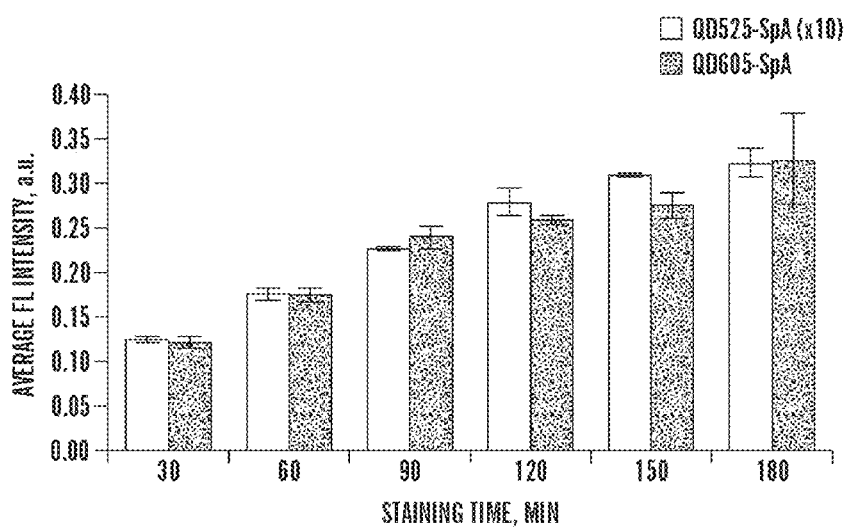
Figure 20C:
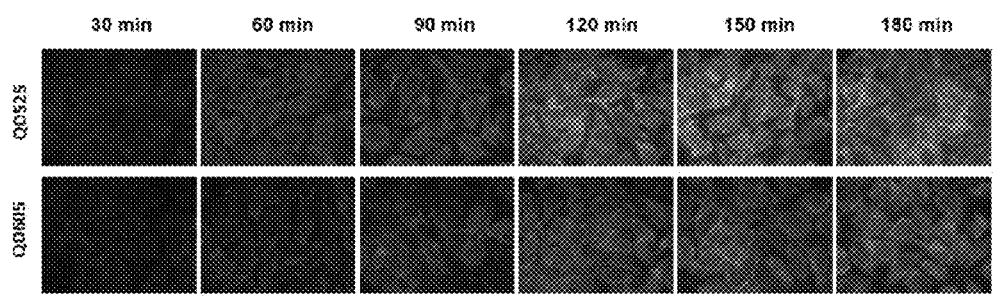

To test QD/SpA-Ab probe stability and examine cross-talk experimentally with cell staining, the inventors prepared QD525-Ab and QD565-Ab probes in a pre-staining step. The inventors chose androgen receptor as staining target for its high expression in LNCaP cells and distinct nuclear localization. Immediately before staining, invnetors mixed QD-Ab probes with counterpart non-complexed QD/SpA (i.e. QD525-Ab were mixed with QD565/SpA, while QD565-Ab were mixed with QD525/SpA) in staining buffer and incubated with cells. With this setup, a large excess of vacant counterpart QD/SpA probes can bind any free Ab released from QD-Ab probes and compete for biomarker binding, producing cross-talk. However, the inventors did not observe any cross-talk staining with either QD525-Ab or QD565-Ab (FIG. 19, top and middle rows). At the same time, QD525/SpA and QD565/SpA probes mixed together with Ab and incubated with cells efficiently captured free Ab from solution and produced mixed-color AR staining with nearly 50% contribution by each (FIG. 19, bottom row). Therefore, SPR data analysis and staining results show that pre-formed QD/SpA-Ab complex, featuring very slow dissociation kinetics and sterically blocking access to bound Ab, could not release free Ab into solution or exchange bound Ab with other vacant QD/SpA probes within the concentration range and time-frame of a cell staining experiment, thus producing no detectable cross-talk between different probes and permitting reliable and specific parallel multiplexed staining. Further, as seen in FIG. 20, QD-SpA probes provided consistent size and biomarker staining kinetics on HeLa cells.

It should be noted that the success of 1-step purification-free preparation of QD/SpA-Ab probes depended on the optimal combination of QD/SpA and Ab parts. Having QD/SpA in slight excess over Ab ensured complete capture of antibodies, which was essential for eliminating probe cross-talk. Even though QD/SpA (likely featuring multiple SpA per QD) could accommodate a range of Ab concentrations in preparation of functional QD-Ab probes, large excess of antibodies saturated all SpA binding sites, thus leaving free Ab in solution. In cases when Ab concentration or QD/SpA Ab binding capacity were not known, each Ab/QD combination was optimized and checked using cross-talk staining experiments as described above. However, such an approach might not be practical for highly multiplexed staining experiments. Therefore, in an alternative approach, QD/SpA and antibodies were mixed in roughly 1:1 ratio during the pre-staining procedure. Then, SpA-functionalized magnetic beads (MB/SpA) were added and briefly incubated QD-Ab mixture to capture free antibodies. As QD-bound antibodies were not accessible to MB/SpA, no QD-Ab probes were consumed by this step, while all unbound antibodies were efficiently removed from staining solution, completely eliminating probe cross-talk (data not shown).

Sequential Cyclic Staining with QD/SpA-Ab Probes:

Cyclic staining involves multiple rounds of complete IF staining on the same specimen. Therefore, complete de-staining after each IF cycle is can provide for accurate biomarker detection. Generally, the de-staining step should remove the fluorescence signal. It can also be useful to remove all the probe components, including 1'Ab, to ensure no carry-over fluorescence signal and preclude binding of vacant QD/SpA probes to left-over 1'Ab. At the same time, de-staining procedure should be gentle enough to preserve specimen morphology and biomarker antigenicity. Microwave treatment[5], strong acidic conditions[4,6,7], and specimen dehydration[6] have been used with some success for sequential staining procedures based on conventional IF and IHC. See, for example, Pirici, D. et al. Antibody elution method for multiple immunohistochemistry on primary antibodies raised in the same species and of the same subtype. *J Histochem Cytochem* 57, 567575 (2009); Toth, Z. E. & Mezey, E. Simultaneous visualization of multiple antigens with tyramide signal amplification using antibodies from the same species. *J Histochem Cytochem* 55, 545-554 (2007); Glass, G., Papin, J. A. & Mandell, J. W. SIMPLE: a sequential immunoperoxidase labeling and erasing method. *J Histochem Cytochem* 57, 899-905 (2009); and Wahlby, C., Erlandsson, F., Bengtsson, E. & Zetterberg, A. Sequential immunofluorescence staining and image analysis for detection of large numbers of antigens in individual cell nuclei. *Cytometry* 47, 32-41 (2002). However, elimination of large staining complexes (often consisting of cross-linked primary and secondary antibodies conjugated with an enzyme or streptavidin and surrounded by precipitated dye) can be challenging and can require extensive chemical or thermal treatment, which can led to biomarker degradation.

Figure 21:
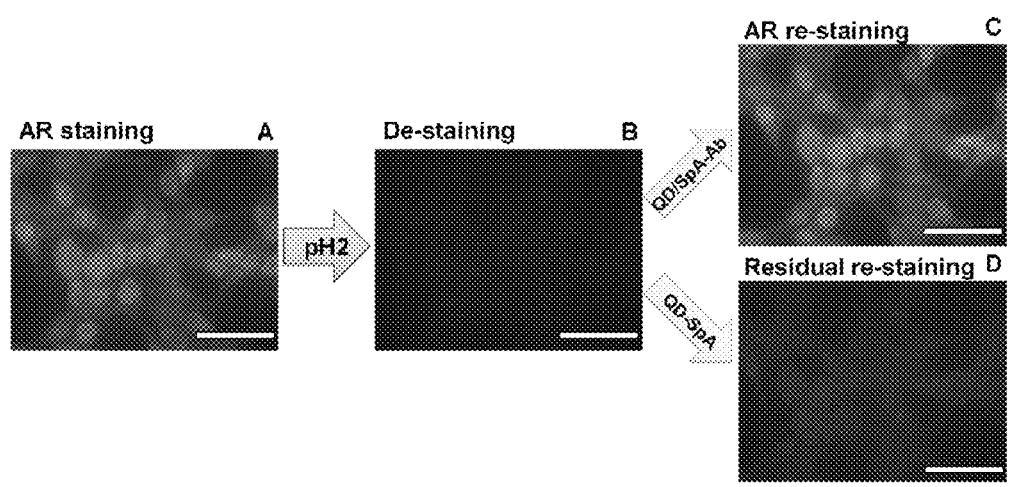
FIGS. 21A-21D show efficiency of QD/SpA-Ab elution for specimen de-staining.
Figure 22:
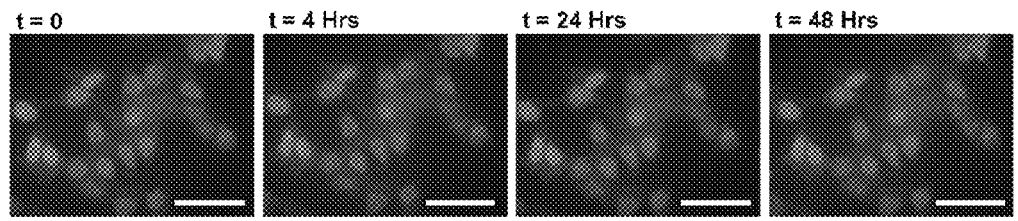
FIG. 22 shows long-term stability of staining with QD/SpA-Ab probes. Androgen receptor was stained with QD/SpA probes pre-assembled with anti-AR Ab using a 1-step procedure. Then true-color images of the same sub-population of cells were taken immediately after staining (at t=0), and after 4, 24, and 48 hours of incubation in TBS buffer at 4° C. Nearly complete retention of QD probes even after 48 hours showed high durability of staining. Scale bar, 50 μm.

With QD/SpA-Ab probes, quick and efficient de-staining can be achieved by brief exposure to low-pH buffer since the staining procedure does not involve formation of large precipitates. The SpA-Ab bond can be easily broken by exposure to low pH and biomarker-bound antibodies are free to dissociate from the specimen. Thus, any residual QD fluorescence could be completely quenched. The inventors stained AR with QD545/SpA (FIG. 21A) and de-stained by incubation with pH2 Glycine-HCl/0.1% casein buffer for 15 minutes. Imaging of the same sub-population of cells revealed no residual staining (FIG. 21B). To test whether the original biomarker was de-occupied, the inventors re-stained AR with the same QD545/SpA-Ab probes during the second cycle, achieving nearly complete restoration of fluorescence signal (FIG. 21C), whereas re-staining with QD545/SpA alone during the third cycle produced only minor background staining (FIG. 21D). At the same time, without de-staining procedure QD staining persisted with nearly no signal loss for at least 48 hours when cells were incubated in TBS at 4° C. (FIG. 22). These results show that low-pH de-staining can be achieved by dissociation of QD/SpA-Ab probe, either as separate components or as a whole complex, from the biomarker, thus leaving behind unoccupied biomarkers.

Figure 23:
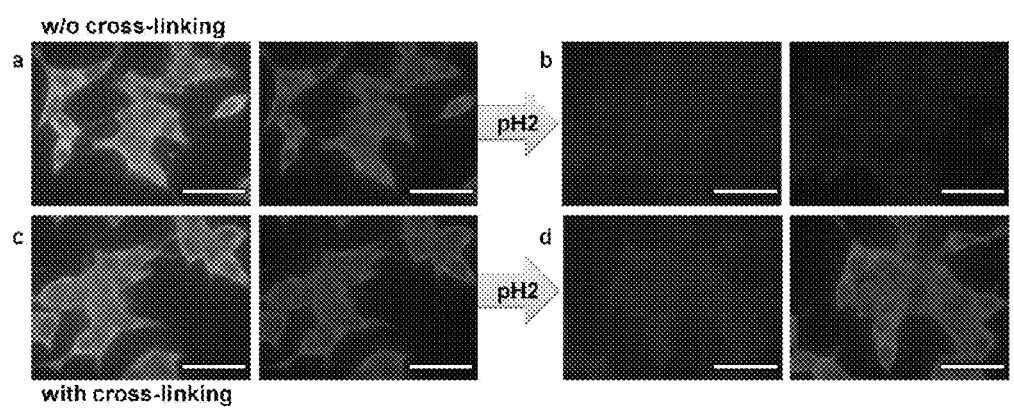
FIGS. 23A-23D show QD quenching vs. elution during low-pH-mediated de-staining.

To test whether QD-SpA probe was washed away from the specimen following dissociation from the biomarker, the inventors labeled QD/SpA with pH-stable Alexa Fluor 568 dye (as QD fluorescence could not be used for imaging of QD/SpA probes after de-staining due to QD quenching). QD525/SpA probes were used for this study to achieve clear spectral separation between the QD and dye fluorescence. AR staining with dye-labeled QD/SpA-Ab probes produced characteristic nuclear staining pattern detectable in both QD and dye channels (FIG. 23A). Following de-staining QD signal was completely eliminated, as expected, while barely detectable nuclear signal in dye channel suggested that minor amount of QD/SpA was left in the specimen (FIG. 23B). At the same time, QD/SpA-Ab probes cross-linked to the specimen with BS3 showed similar dye signal before (FIG. 23C) and after (FIG. 23D) de-staining, confirming that localization of QD/SpA probe can be reliably detected with organic dye. Therefore, complete de-staining was achieved primarily by dissociation of QD/SpA-Ab probe from the biomarker and washing away from the specimen, while low-pH mediated QD quenching eliminated minor fluorescence of residual QD probes retained within the specimen due to non-specific interactions.

Figure 24:
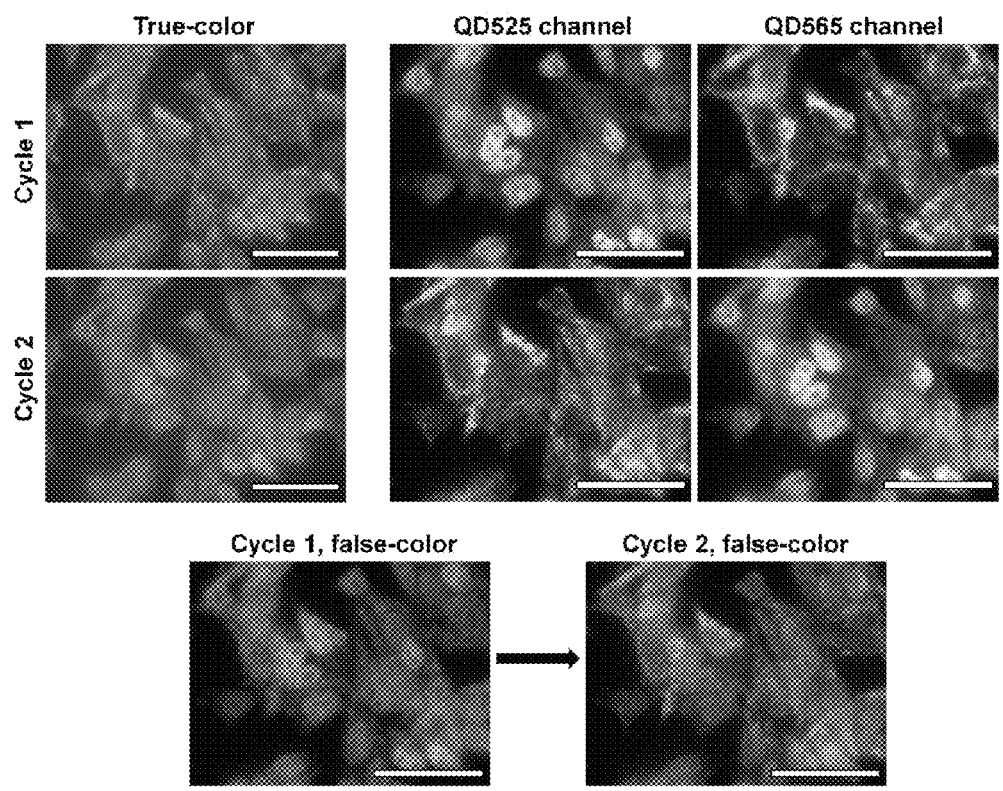
FIG. 24 shows biomarker re-staining and target exchange with cyclic parallel staining. During the first cycle (top row) parallel staining of AR with QD525 and MAOA with QD565 was achieved. Spectral imaging and unmixing revealed distinct AR staining pattern in QD525 channel (middle panel) and MAOA pattern in QD565 channel (right panel). Following de-staining, during the second cycle (middle row) same biomarkers were stained with counterpart QD probes. In this case, clear MAOA pattern was detected in QD525 channel (middle panel) and AR—in QD565 channel (right panel). Therefore, complete target re-staining with a different probe was achieved (bottom row), while no cross-talk between probes within the same cycle or between cycles was observed. Intensity of QD525 channel was increased 4 times relative to QD565 channel to compensate for differential brightness of QD probes. Scale bar, 50 μm.

The results demonstrate robustness of multiplexed cyclic staining procedure by performing 2-color AR/MAOA staining on the first cycle and achieving complete target exchange on the second cycle. In particular, during the first cycle AR was stained with QD525/SpA-Ab probes and MAOA was stained with QD565/SpA-Ab. Spectral imaging and signal unmixing produced characteristic AR and MAOA staining patterns in QD525 and QD565 channels respectively (FIG. 24, top row). Then the specimen was de-stained, and biomarker/QD pairs were switched (i.e. AR was stained with QD565, while MAOA—with QD525). Imaging of the same sub-population of cells revealed re-staining of each biomarker with a counterpart probe (FIG. 24, middle row), thus achieving complete target exchange with no probe cross-talk within one cycle or between different cycles (FIG. 24, bottom row).

Figure 25:
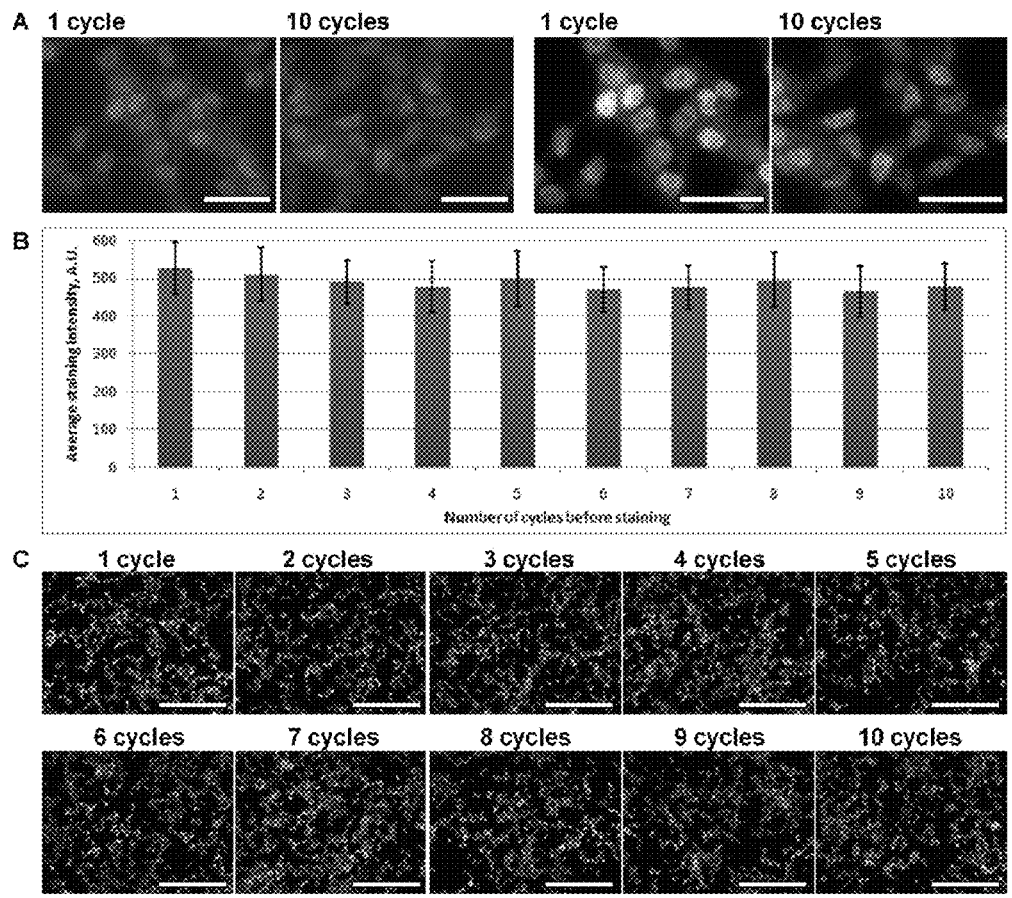
FIGS. 25A-25C show biomarker stability during cyclic exposure to low-pH degradation conditions.
Figure 26A:
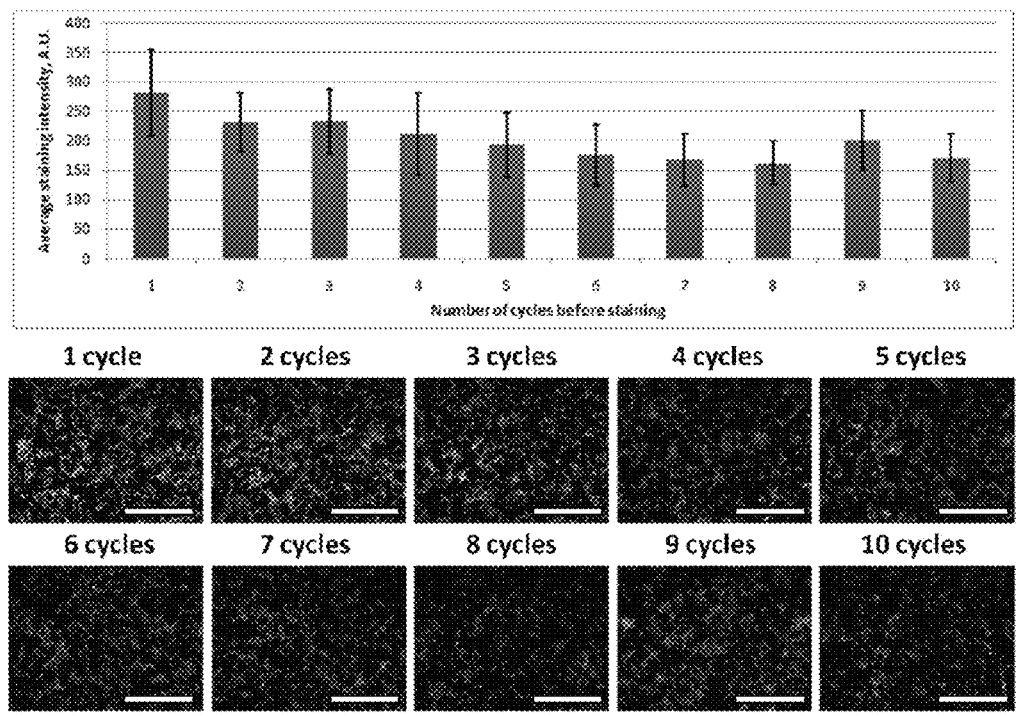
FIGS. 26A and 26B show effect of pre-staining cell processing on biomarker preservation during sequential staining. Cells were fixed with 4% formaldehyde/TBS for 10 minutes (FIG. 26A) or 20 minutes (FIG. 26B) at room temperature, followed by permeabilization with 2% DTAC and 0.5% Triton X-100. Insufficient cell fixation in (FIG. 26A) resulted in significant loss of biomarker antigenicity after only a few low-pH degradation cycles, while properly processed cells showed high biomarker stability throughout at least 10 cycles. Low-magnification microscopy with spectral imaging was done after each degradation cycle. Signal unmixing, background removal, and average AR staining intensity measurements were done to quantitatively examine biomarker stability. Scale bar, 500 μm.
Figure 26B:
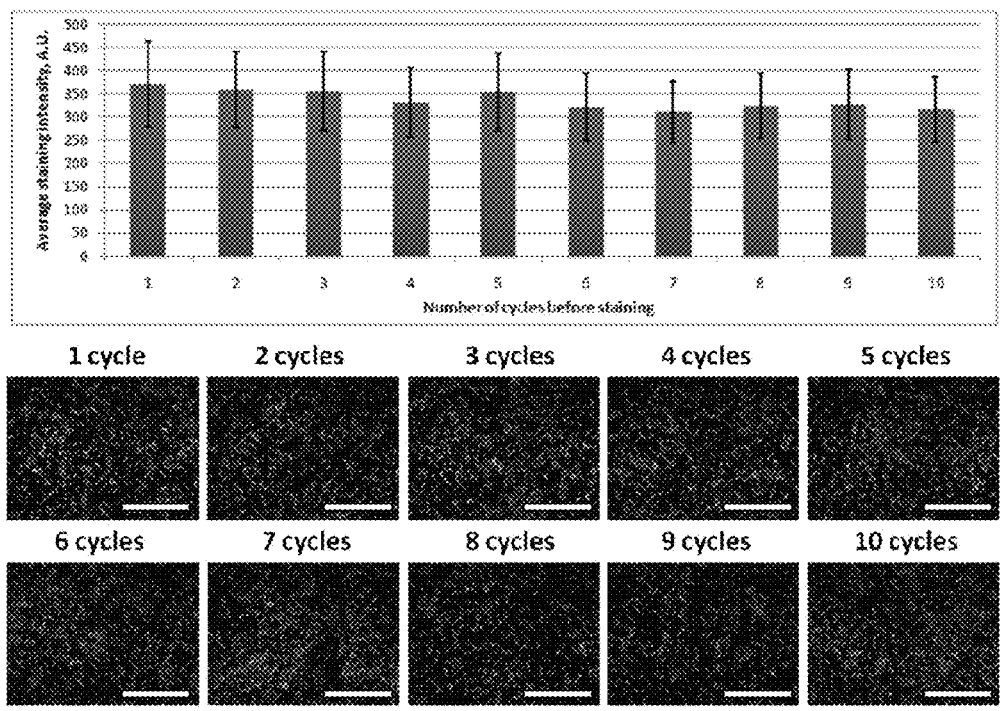

Finally, the inventors assessed the effect of cyclic treatment on specimen morphology and biomarker antigenicity. The inventors performed this experiment on cells located in 10 separate wells of the same 24-well glass-bottom plate, thus ensuring that all cells were prepared in identical conditions. Then cells were exposed to M degradation cycles (where M ranged from 1 to 10). Each cycle consisted of washing, de-staining, and blocking, thus imitating full IF staining cycle, but skipping the staining step. Treatment was performed in 5-cycle portions over 2 days, with overnight incubation in TBS at 4° C. Cells treated for less than 10 cycles were kept in TBS for (10-M) cycles and then were exposed to degradation conditions. Following cyclic treatment, AR staining was performed simultaneously on all cells using identical QD545/SpA-Ab probes. Low- and high-magnification microscopy and image acquisition was done with the same camera exposure time and other imaging parameters to enable consistent signal quantification and comparison of staining intensity between cycles. High-magnification true-color and unmixed spectral images revealed just minor loss of staining intensity after 10 degradation cycles (FIG. 25A). To quantify biomarker degradation, the inventors measured average nuclear staining intensity throughout a large number of cells imaged at low magnification. Spectral imaging and deconvolution were used to remove cell autofluorescence and measure only QD fluorescence signal. Quantitative analysis revealed no more than 10% signal loss during 10 degradation cycles (FIG. 25B), which was consistent with qualitative evaluation of low-magnification unmixed images (FIG. 25C). Some variability in nuclear staining observed here could be assigned to natural variability in AR expression. It should be noted that successful preservation of biomarker antigenicity relied on appropriate pre-staining cell preparation. In particular, the inventors found that optimized cell fixation and permeabilization were critical. Incomplete cell fixation with formaldehyde/TBS yielded over 40% signal drop after 10 degradation cycles (FIG. 26), while fixation with formaldehyde/PBS and Triton X-100 permeabilization failed to preserve biomarker antigenicity even after one de-staining (data not shown). At the same time, over-fixation often led to hampered QD intracellular access, reduced staining efficiency, and enhanced non-specific nuclear binding.

In order to confirm that complete staining/imaging/de-staining cycles did not lead to alterations in biomarker antigenicity and staining efficiency, the inventors repeated the same 1-color 5-cycle sequential staining described above in an opposite biomarker order, i.e. instead of staining from low-abundance to high abundance biomarker (FIG. 27, top row), the inventors performed staining from high-abundance to low-abundance biomarker (FIG. 27, bottom row). Not only absence of carry-over or crosstalk signal was observed throughout the 5 cycles, but also consistent biomarker distribution and staining intensity was demonstrated independent of the staining sequence. This confirmed the robustness and reliability of the multiplexed cyclic staining method described here.

The highly multiplexed cyclic staining methods described herein provides access to single-cell molecular profiling within the context of preserved tissue or cell culture morphology. Even within the same cell culture each cell may exhibit its own unique features, unique molecular portrait (at least due to variations in cell state and cycle). Batch analysis of large cell populations erases such variations, providing simplistic and often deceptive averaged information. This issue is more pronounced when analysis of tissue specimens, consisting of multiple cell types, is attempted, or when the discovery of scarce cells with distinct molecular profiles is desired (e.g. identification of cancer progenitor cells). Throughout the studies on LNCaP cell cultures described herein, the inventors routinely observed variations in biomarker expression levels between different cells.

Accordingly, disclosed herein is a method for single-cell molecular profiling. In one aspect, single-cell molecular profiling can be achieved by (i) parallel multiplexed staining method capable of utilizing full range of spectrally distinguishable QD probes simultaneously in a simple 1-step procedure; (ii) sequential multiplexed staining method permitting performance of multiple parallel staining procedures on the same specimen, thus dramatically increasing the number of biomarkers that could be analyzed; and (iii) a universal QD/SpA platform featuring quick and simple preparation of an extensive library of functional QD-Ab probes while exhibiting no cross-talk between different probes either within a staining cocktail or between different staining cycles. The utility of the method was demonstrated by performing 5-biomarker staining either in parallel or sequential format, confirming potential for obtaining at least 25-biomarker profiles. The number of biomarkers imaged simultaneously was limited by the current availability of suitable QD probes. While QDs in 500-600 nm range featured narrow fluorescence emission profiles, thus permitting reliable signal unmixing, the quality of QDs in 600-700 nm range was lower. With synthesis of higher-quality QDs covering full visible spectral range and advances in spectral imaging, simultaneous imaging of over 10 biomarkers can be achieved. At the same time, the inventors also demonstrated that up to 10 staining cycles could be performed without significant loss of biomarker antigenicity and cell morphology. Therefore, comprehensive single-cell molecular profiles consisting of over 100 biomarkers can be performed using the methods described herein.

The universal QD/SpA platform, as described herein, provides flexibility to the method. Preparation of unique biomarker-specific fluorescent probes represents a significant hurdle for highly multiplexed detection methods, as direct QD-Ab assembly (either via non-covalent or covalent bonds) is technically complex, time-consuming, and prohibitively expensive, while providing limited flexibility in matching QD-biomarker pairs and requiring long-term storage of QD-Ab probes. In contrast, QD/SpA featured on-demand 1-step purification-free QD-Ab assembly along with high probe stability and specificity. Notably, the SpA-Ab bond proved to be sufficiently stable to avoid QD-Ab probe cross-talk, while easily breakable for de-staining purposes. Overall, PEG-coated QDs combined with SpA exhibited several features useful for an IF imaging probe: (i) QD-Ab preparation was fast, inexpensive, and suitable for a wide range of users without specialized technical skills; (ii) direct biomarker labeling ensured 1:1 correlation between biomarker expression and fluorescence signal, while high brightness of QD probes made imaging without a signal amplification step possible; (iii) the SpA-Ab bond could be easily broken at low-pH conditions, thus providing a suitable route for QD-Ab probe disassembly during de-staining step; and (iv) QD fluorescence could be efficiently quenched by low-pH conditions, eliminating even minor non-specific staining after each cycle and preventing build-up of background signal. With such design flexibility, newly developed QDs and biomarker-specific antibodies can be easily incorporated within the methods described herein. A wide range of laboratories can use the cyclic multiplexed staining method described herein for addressing their specific research goals.

Utilization of a reliable comprehensive single-cell molecular profiling technique based on cyclic multiplexed staining with QD-Ab probes can provide a great benefit for both biomedical research and clinical diagnostics by providing a tool for addressing phenotypic heterogeneity within large cell populations, opening access to studying low-abundance events often masked or completely erased by batch processing, and elucidating biomarker signatures of diseases critical for accurate diagnosis and targeted therapy.

To the extent not already indicated, it will be understood by those of ordinary skill in the art that any one of the various embodiments herein described and illustrated can be further modified to incorporate features shown in any of the other embodiments disclosed herein.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A composition comprising an affinity molecule reversibly conjugated to a label moiety, in which the affinity molecule is linked to the label moiety via a linker comprising first and second strands of nucleic acid that specifically hybridize to each other,
wherein the first nucleic acid strand is linked to the affinity molecule via an adaptor molecule or via a linker selected from the group consisting of succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond, an amide bond, two amide bonds on a spacer for cross-linking two —NH$_2$ groups triazole (from "click" reaction), a phosphodiester linkage, a phosphorothioate linkage, or a combination thereof,
and wherein the second nucleic acid strand is linked to the label via an adaptor molecule or via a linker selected from the group consisting of succinimidyl-4-(N-maleimidomethyl)cyclohexane-1-carboxylate (SMCC) linker, sulfo-SMCC linker, succinimidyl-6-hydrazino-nicotinamide (S-HyNic) linker, N-succinimidyl-4-formylbenzamide (S-4FB) linker, bis-aryl hydrazone bond, an amide bond, two amide bonds on a spacer for cross-linking two —NH$_2$ groups, triazole bond (from "click" reaction), a phosphodiester linkage, a phosphorothioate linkage, or a combination thereof,
such that the affinity molecule is conjugated to the label moiety under conditions that permit hybridization between the first and second nucleic acid strands, but is not conjugated to the label under conditions that do not permit such hybridization.

2. The composition of claim 1, wherein the first and second nucleic acid strands hybridize to form a double-stranded region of about 6 base-pairs to about 30 base-pairs.

3. The composition of claim 1, wherein the first and second nucleic acid strands hybridize to form a double-stranded region having a melting temperature about 40° C. or above.

4. The composition of claim 1, wherein the first and second nucleic acid strands hybridize to form a double-stranded region having a 3' or 5' single-stranded overhang of about 6 to about 20 nucleotides.

5. The composition of claim 1, wherein the affinity molecule and the label moiety are in a 1:1 (affinity molecule: label moiety) ratio.

6. The composition of claim 1, wherein
(i) the affinity molecule is conjugated to 3' terminus of the first nucleic acid strand and the label moiety is conjugated to 3' terminus of the second nucleic acid strand; or
(ii) the affinity molecule is conjugated to 5' terminus of the first nucleic acid strand and the label moiety is conjugated to 5' terminus of the second nucleic acid strand.

7. The composition of claim 1, wherein at least one of the first or the second strands of nucleic acid comprises a modification selected from the group consisting of nucleobase modifications, sugar modifications, inter-sugar linkage modifications, backbone modifications, and any combinations thereof.

8. The composition of claim 1, wherein the affinity molecule is an antibody or antigen-binding portion thereof.

9. The composition of claim 1, wherein the adaptor molecule is selected from the group consisting of protein A, protein G, antibody, antibody fragment, antigen, receptor ligand, receptor, ligand binding fragment of a receptor, member of a coupling pair, aptamer, biotin-streptavidin pair, and combinations thereof.

10. The composition of claim 1, wherein the label moiety is covalently linked to the second nucleic acid strand through a linker.

11. The composition of claim 1, wherein the label moiety is non-covalently linked to the second nucleic acid via a coupling pair.

12. The composition of claim 1, wherein the label moiety is selected from the group consisting of a luminescent nanoparticle, fluorescent molecule, chemiluminescent moiety, bioluminescent moiety, luminescent molecule, radioisotope, chromophore, magnetic nanoparticles, plasmonic nanoparticles, upconverting nanoparticles, nanoparticles comprising fluorescent molecules, nanoparticles comprising fluorophores, and any combination thereof.

13. The composition of claim 12, wherein the luminescent nanoparticle is an inorganic semiconductor nanoparticle chosen from group consisting of Group II, Group III, Group IV, Group V, and Group VI semiconductor nanoparticles.

14. The composition of claim 12, wherein the luminescent nanoparticle is selected from the group consisting of cadmium selenide (CdSe), cadmium sulfide (CdS), cadmium telluride (CdTe), cadmium zinc sulfide (CdZnS), cadmium telluride silicone (CdTeSi), cadmium mercury telluride (CdHgTe), zinc selenide (ZnSe), zinc sulfide (ZnS), zinc oxide (ZnO), lead sulfide (PbS), lead selenide (PbSe), gallium arsenide (GaAs), indium phosphide (InP), indium arsenide (InAs), silicon (Si), Ge, SiGe, and a combination thereof.

15. The composition of claim 12, wherein the luminescent nanoparticle comprises a core and a shell forms a colloidal particle.

16. The composition of claim 12, wherein the luminescent nanoparticle core comprises CdSe and the shell comprises ZnS.

17. The composition of claim 12, wherein the luminescent nanoparticle is about 1 nm to about 100 nm in size.

18. The composition of claim 12, wherein the luminescent nanoparticle comprises a polymer coating layer.

19. The composition of claim 18, wherein the polymer is polyethylene glycol.

20. The composition of claim 12, wherein the luminescent nanoparticle is a colloidal water-soluble nanoparticle comprising a stable non-fouling coating wherein non-specific binding of the nanoparticle to a cell or a tissue sample is 5% or less relative to a nanoparticle lacking a non-fouling coating.

21. A kit comprising a composition of claim 1.

22. A composition comprising an affinity molecule reversibly conjugated to a luminescent nanoparticle, in which the nanoparticle is covalently linked to an adaptor molecule and the adaptor molecule is non-covalently linked to the affinity molecule, wherein the affinity molecule and the adaptor molecule are present in a 1:1 ratio, and wherein the luminescent nanoparticle is a colloidal water-soluble nanoparticle comprising a stable non-fouling coating wherein non-specific binding of the nanoparticle to a cell or a tissue sample is 5% or less relative to a nanoparticle lacking a non-fouling coating.

23. A composition comprising a plurality of different affinity molecules, each member of the plurality binding a different target, wherein each different affinity molecule is reversibly conjugated to a luminescent nanoparticle, in which the nanoparticle is covalently linked to an adaptor molecule and the adaptor molecule is non-covalently linked to the affinity molecule, wherein the affinity molecule and the adaptor molecule are present in a 1:1 ratio, and wherein the luminescent nanoparticle is a colloidal water-soluble nanoparticle comprising a stable non-fouling coating wherein non-specific binding of the nanoparticle to a cell or a tissue sample is 5% or less relative to a nanoparticle lacking a non-fouling coating, and wherein emission spectra of the different luminescent nanoparticles are distinguishable from one another.

24. A method of analyzing a sample for a plurality of analytes, the method comprising, in order:
(a) contacting the sample with a first plurality of different affinity molecules under conditions that permit specific analyte binding by the different affinity molecules, wherein each different affinity molecule specifically binds a different member of the plurality of analytes and members of the plurality of different affinity molecules become bound to members of the plurality of analytes present in the sample, wherein each different affinity molecule is reversibly conjugated to a different luminescent nanoparticle, in which the nanoparticle is covalently linked to an adaptor molecule and the adaptor molecule is non-covalently linked to the affinity molecule, the affinity molecule and the adaptor molecule are present in a 1:1 ratio, and wherein the luminescent nanoparticle is a colloidal water-soluble nanoparticle comprising a stable non-fouling coating wherein non-specific binding of the nanoparticle to a cell or a tissue sample is 5% or less relative to a nanoparticle lacking a non-fouling coating, and detectable properties of the luminescent nanoparticles are distinguishable from one another; and
(b) detecting signal from luminescent nanoparticles associated with the first plurality of affinity molecules bound to the sample, thereby detecting the presence or amount of the plurality of analytes.

25. The method of claim 24, further comprising the steps of:
(c) erasing the signal from the luminescent nanoparticles conjugated to the first set of different affinity molecules;
(d) contacting the sample with a second set of the plurality of different affinity molecules under conditions that permit specific analyte binding by the different affinity molecules;
(e) detecting signal from luminescent molecules associated with the second set of affinity molecules bound to the sample, thereby detecting the presence or amount of at least a subset of the plurality of analytes; and
(f) optionally repeating steps (c)-(e) with a further second set of the affinity molecules.

26. A composition comprising an affinity molecule reversibly conjugated to a luminescent nanoparticle label, in which the affinity molecule is linked to the label via a linker comprising first and second strands of nucleic acid that specifically hybridize to each other,
wherein the first nucleic acid strand is linked to the affinity molecule, and wherein the second nucleic acid strand is linked to the luminescent nanoparticle label,
such that the affinity molecule is conjugated to the nanoparticle label under conditions that permit hybridization between the first and second nucleic acid strands, but is not conjugated to the nanoparticle label under conditions that do not permit such hybridization, and
wherein the luminescent nanoparticle is a colloidal water-soluble nanoparticle comprising a stable non-fouling coating wherein non-specific binding of the nanoparticle to a cell or a tissue sample is 5% or less relative to a nanoparticle lacking a non-fouling coating.

* * * * *